United States Patent
Sabina et al.

(10) Patent No.: US 11,759,295 B2
(45) Date of Patent: *Sep. 19, 2023

(54) DIAGNOSTIC INTRAORAL METHODS AND APPARATUSES

(71) Applicant: Align Technology, Inc., San Jose, CA (US)

(72) Inventors: Michael Sabina, Campbell, CA (US); Avi Kopelman, Palo Alto, CA (US); Eric Kuo, San Jose, CA (US); Gilad Elbaz, Tel Aviv (IL); Assaf Weiss, Yavne (IL); Doron Malka, Tel Aviv (IL); Ofer Saphier, Rehovot (IL); Eliahou Franklin Nizard, Jerusalem (IL); Ido Tishel, Kfar Bilu (IL); Shai Ayal, Shoham (IL); Maayan Moshe, Ra'anana (IL)

(73) Assignee: Align Technology, Inc., San Jose, CA (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/209,166

(22) Filed: Mar. 22, 2021

(65) Prior Publication Data

US 2021/0205054 A1 Jul. 8, 2021

Related U.S. Application Data

(63) Continuation of application No. 16/258,527, filed on Jan. 25, 2019, now Pat. No. 11,013,581.
(Continued)

(51) Int. Cl.
*A61C 9/00* (2006.01)
*A61B 1/00* (2006.01)
(Continued)

(52) U.S. Cl.
CPC ...... *A61C 9/0053* (2013.01); *A61B 1/000094* (2022.02); *A61B 1/000096* (2022.02);
(Continued)

(58) Field of Classification Search
CPC ... A61C 9/0053; A61C 7/002; A61C 13/0004; A61C 13/0019; A61C 13/34;
(Continued)

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |

(Continued)

FOREIGN PATENT DOCUMENTS

| | | |
|---|---|---|
| CN | 104349710 A | 2/2015 |
| JP | 2012147908 A | 8/2012 |
| WO | 2016029383 A1 | 3/2016 |

OTHER PUBLICATIONS

Szymczak A., et al., "3D Shape from Silhouette Points in Registered 2D Images Using Conjugate Gradient Method", Proceedings of SPIE, Mar. 2010, 8 pages.
(Continued)

*Primary Examiner* — Jayanti K Patel
*Assistant Examiner* — Richard B Carter
(74) *Attorney, Agent, or Firm* — Shay Glenn LLP

(57) ABSTRACT

Methods and apparatuses for taking, using and displaying three-dimensional (3D) volumetric models of a patient's dental arch. A 3D volumetric model may include surface (e.g., color) information as well as information on internal structure, such as near-infrared (near-IR) transparency values for internal structures including enamel and dentin.

20 Claims, 23 Drawing Sheets

Related U.S. Application Data

(60) Provisional application No. 62/758,503, filed on Nov. 9, 2018, provisional application No. 62/622,798, filed on Jan. 26, 2018.

(51) Int. Cl.

| | | |
|---|---|---|
| *A61B 1/06* | (2006.01) | |
| *A61B 1/24* | (2006.01) | |
| *G06T 19/00* | (2011.01) | |
| *A61B 5/00* | (2006.01) | |
| *A61B 6/14* | (2006.01) | |
| *A61C 7/00* | (2006.01) | |
| *A61C 13/00* | (2006.01) | |
| *A61C 13/34* | (2006.01) | |

(52) U.S. Cl.
CPC ...... *A61B 1/00172* (2013.01); *A61B 1/00186* (2013.01); *A61B 1/00194* (2022.02); *A61B 1/0638* (2013.01); *A61B 1/0646* (2013.01); *A61B 1/24* (2013.01); *A61B 5/0086* (2013.01); *A61B 5/0088* (2013.01); *A61B 6/145* (2013.01); *A61C 7/002* (2013.01); *A61C 13/0004* (2013.01); *G06T 19/00* (2013.01); *A61B 5/0062* (2013.01); *A61B 5/0066* (2013.01); *A61B 5/4547* (2013.01); *A61C 13/0019* (2013.01); *A61C 13/34* (2013.01); *G06T 2200/24* (2013.01); *G06T 2207/30036* (2013.01); *G06T 2210/41* (2013.01)

(58) Field of Classification Search
CPC ........ A61B 1/000094; A61B 1/000096; A61B 1/00194; A61B 1/00172; A61B 1/00186; A61B 1/0638; A61B 1/0646; A61B 1/24; A61B 5/0086; A61B 5/0088; A61B 6/145; A61B 5/0062; A61B 5/0066; A61B 5/4547; G06T 19/00; G06T 2200/24; G06T 2207/30036; G06T 2210/41
USPC ............................................. 348/66; 356/402
See application file for complete search history.

(56) References Cited

U.S. PATENT DOCUMENTS

| | | | |
|---|---|---|---|
| 6,334,853 | B1 | 1/2002 | Kopelman et al. |
| 6,463,344 | B1 | 10/2002 | Pavloskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |
| 7,373,286 | B2 | 5/2008 | Nikolskiy et al. |
| 7,507,088 | B2 | 3/2009 | Taub et al. |
| 7,545,372 | B2 | 6/2009 | Kopelman et al. |
| 7,698,068 | B2 | 4/2010 | Babayoff |
| 7,916,911 | B2 | 3/2011 | Kaza et al. |
| 8,108,189 | B2 | 1/2012 | Chelnokov et al. |
| 8,244,028 | B2 | 8/2012 | Kuo et al. |
| 8,587,582 | B2 | 11/2013 | Matov et al. |
| 8,948,482 | B2 | 2/2015 | Levin |
| D742,518 | S | 11/2015 | Barak et al. |
| 9,192,305 | B2 | 11/2015 | Levin |
| 9,261,356 | B2 | 2/2016 | Lampert et al. |
| 9,261,358 | B2 | 2/2016 | Atiya et al. |
| 9,299,192 | B2 | 3/2016 | Kopelman |
| D760,901 | S | 7/2016 | Barak et al. |
| 9,393,087 | B2 | 7/2016 | Moalem |
| 9,408,679 | B2 | 8/2016 | Kopelman |
| 9,431,887 | B2 | 8/2016 | Boltanski |
| 9,439,568 | B2 | 9/2016 | Atiya et al. |
| 9,451,873 | B1 | 9/2016 | Kopelman et al. |
| D768,861 | S | 10/2016 | Barak et al. |
| D771,817 | S | 11/2016 | Barak et al. |
| 9,491,863 | B2 | 11/2016 | Boltanski |
| D774,193 | S | 12/2016 | Makmel et al. |
| 9,510,757 | B2 | 12/2016 | Kopelman et al. |
| 9,660,418 | B2 | 5/2017 | Atiya et al. |
| 9,668,829 | B2 | 6/2017 | Kopelman |
| 9,675,430 | B2 | 6/2017 | Verker et al. |
| 9,693,839 | B2 | 7/2017 | Atiya et al. |
| 9,717,402 | B2 | 8/2017 | Lampert et al. |
| 9,724,177 | B2 | 8/2017 | Levin |
| 9,844,426 | B2 | 12/2017 | Atiya et al. |
| 10,076,389 | B2 | 9/2018 | Wu et al. |
| 10,098,714 | B2 | 10/2018 | Kuo |
| 10,108,269 | B2 | 10/2018 | Sabina et al. |
| 10,111,581 | B2 | 10/2018 | Makmel |
| 10,111,714 | B2 | 10/2018 | Kopelman et al. |
| 10,123,706 | B2 | 11/2018 | Elbaz et al. |
| 10,136,972 | B2 | 11/2018 | Sabina et al. |
| 10,380,212 | B2 | 8/2019 | Elbaz et al. |
| 10,390,913 | B2 | 8/2019 | Sabina et al. |
| 10,453,269 | B2 | 10/2019 | Furst |
| 10,456,043 | B2 | 10/2019 | Atiya et al. |
| 10,499,793 | B2 | 12/2019 | Ozerov et al. |
| 10,504,386 | B2 | 12/2019 | Levin et al. |
| 10,507,087 | B2 | 12/2019 | Elbaz et al. |
| 10,517,482 | B2 | 12/2019 | Sato et al. |
| 10,695,150 | B2 | 6/2020 | Kopelman et al. |
| 10,708,574 | B2 | 7/2020 | Furst et al. |
| 10,772,506 | B2 | 9/2020 | Atiya et al. |
| 10,813,727 | B2 | 10/2020 | Sabina et al. |
| 10,888,399 | B2 | 1/2021 | Kopelman et al. |
| 10,952,816 | B2 | 3/2021 | Kopelman |
| 10,980,613 | B2 | 4/2021 | Shanjani et al. |
| 11,013,581 | B2 * | 5/2021 | Sabina ................. A61C 7/002 |
| 11,096,765 | B2 | 8/2021 | Atiya et al. |
| 2006/0239526 | A1* | 10/2006 | Jonusauskas ........ A61B 5/682 |
| | | | 348/66 |
| 2010/0141931 | A1* | 6/2010 | Ramirez Mancilla .... G01J 3/50 |
| | | | 356/402 |
| 2012/0015316 | A1 | 1/2012 | Sachdeva et al. |
| 2014/0051040 | A1 | 2/2014 | Kilcher et al. |
| 2014/0314291 | A1 | 10/2014 | Souza et al. |
| 2016/0331465 | A1 | 11/2016 | Kim et al. |
| 2019/0029784 | A1 | 1/2019 | Moalem et al. |
| 2019/0105842 | A1* | 4/2019 | Dau ..................... B33Y 80/00 |
| 2019/0175314 | A1* | 6/2019 | Lagardere ........... A61C 9/0053 |
| 2019/0388193 | A1 | 12/2019 | Saphier et al. |
| 2020/0281700 | A1 | 9/2020 | Kopelman et al. |
| 2020/0281702 | A1 | 9/2020 | Kopelman et al. |
| 2020/0315434 | A1 | 10/2020 | Kopelman et al. |
| 2020/0349698 | A1 | 11/2020 | Minchenkov et al. |
| 2020/0349705 | A1 | 11/2020 | Minchenkov et al. |
| 2020/0404243 | A1 | 12/2020 | Saphier et al. |
| 2021/0030503 | A1 | 2/2021 | Shalev et al. |
| 2021/0059796 | A1 | 3/2021 | Weiss et al. |
| 2021/0068773 | A1 | 3/2021 | Moshe et al. |

OTHER PUBLICATIONS

Taneva E., et al.,"3D Scanning, Imaging, and Printing in Orthodontics", Computer Science, 2015, Chapter 9, pp. 147-188.

* cited by examiner

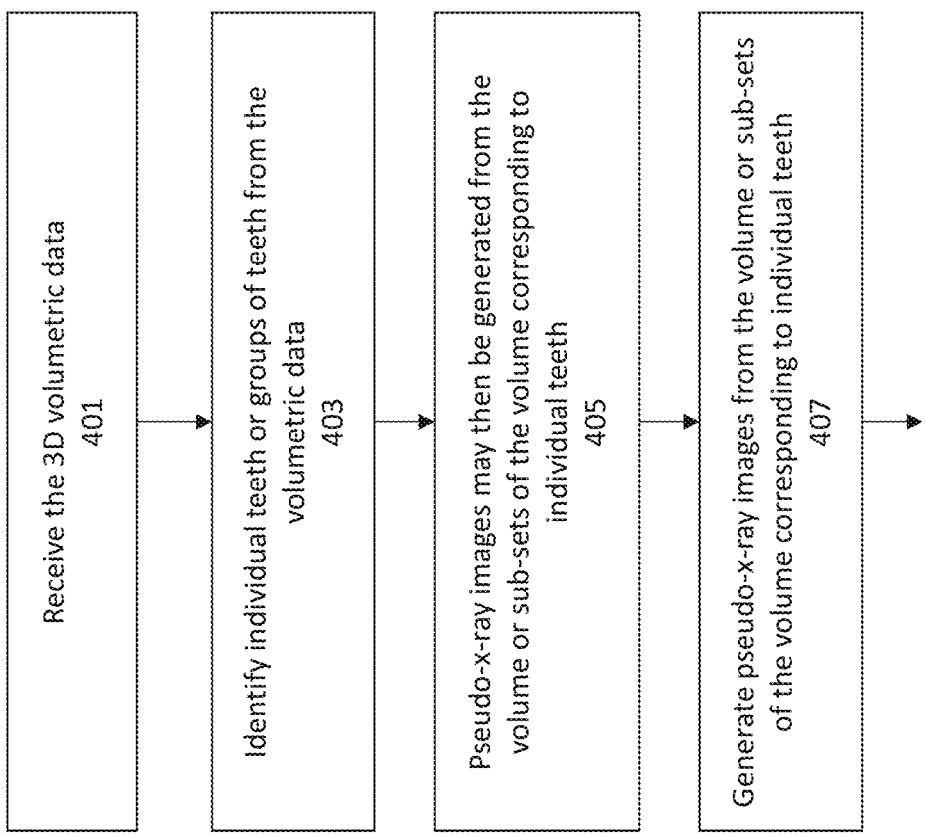

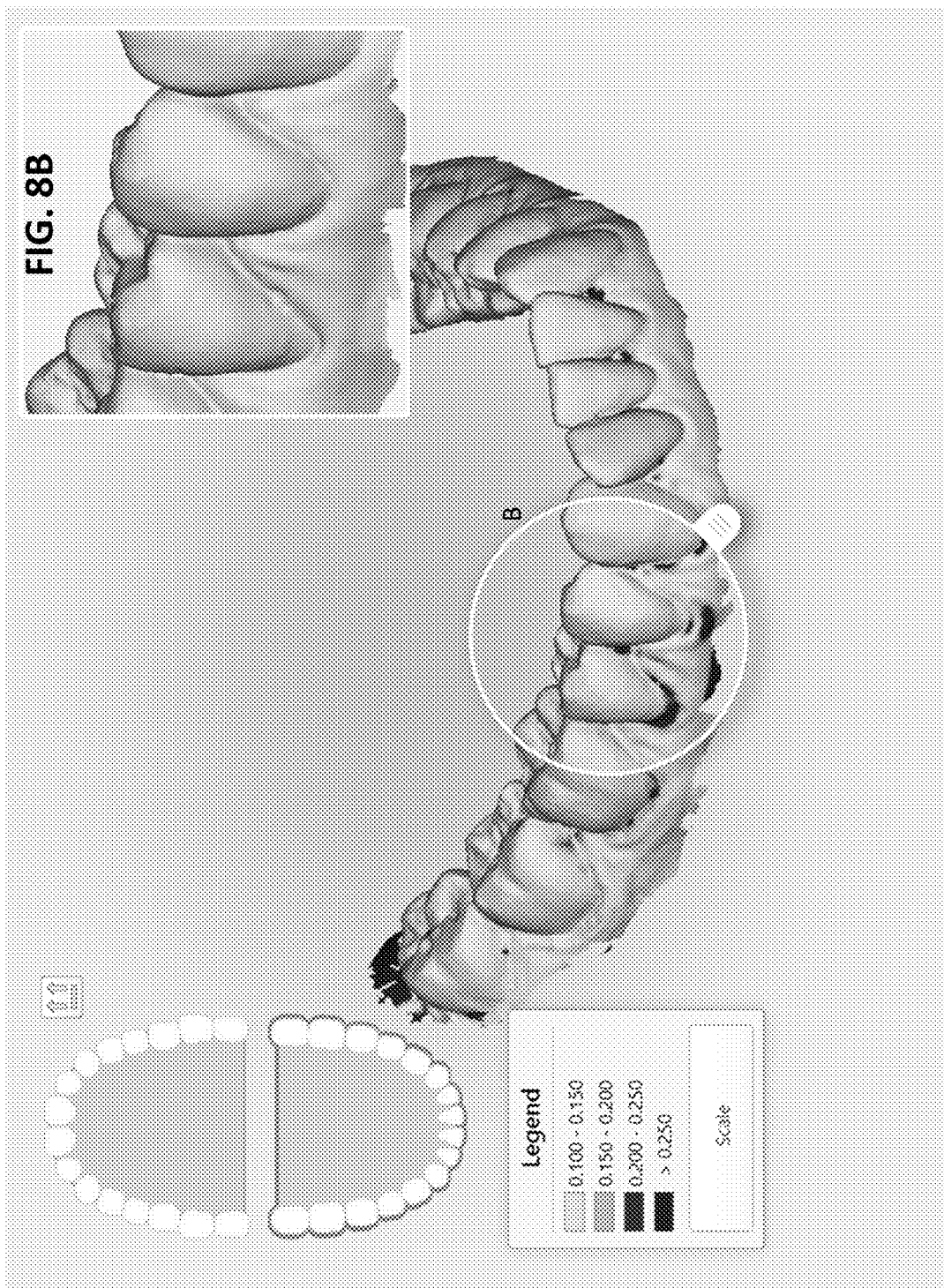

903

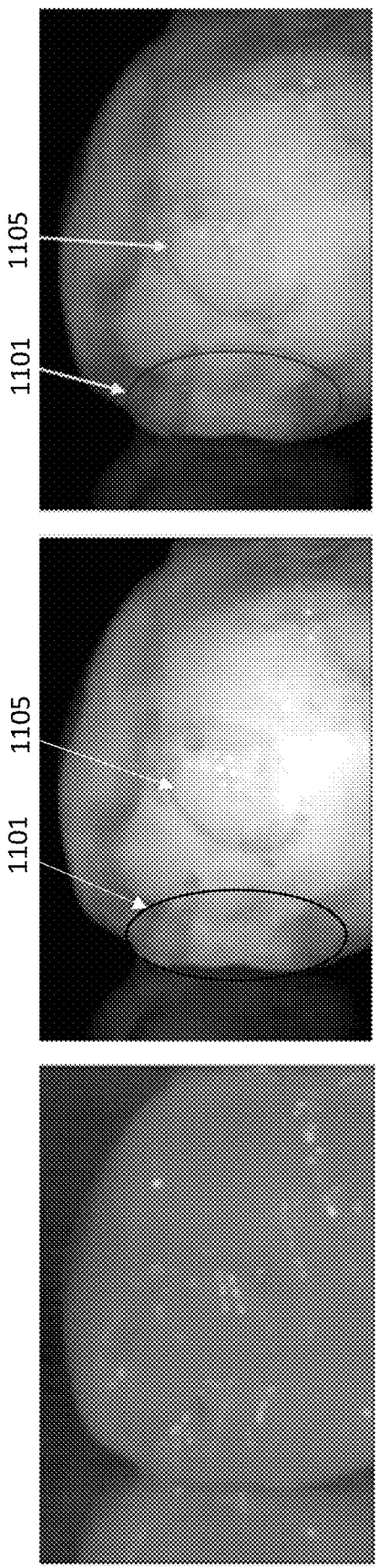

DIAGNOSTIC INTRAORAL METHODS AND APPARATUSES

CROSS REFERENCE TO RELATED APPLICATIONS

This patent application is a continuation of U.S. patent application Ser. No. 16/258,527, filed Jan. 25, 2019, titled "DIAGNOSTIC INTRAORAL METHODS AND APPARATUSES," now U.S. Patent Application Publication No. 2019/0231492, claims priority to U.S. Provisional Patent Application No. 62/622,798, titled "DIAGNOSTIC INTRAORAL SCANNERS," filed on Jan. 26, 2018, and U.S. Provisional Patent Application No. 62/758,503, titled "DIAGNOSTIC INTRAORAL SCANNERS," and filed Nov. 9, 2018, each of which is herein incorporated by reference in its entirety.

This patent application may be related to one or more of: U.S. patent application Ser. No. 15/662,234, filed Jul. 27, 2017, titled "INTRAORAL SCANNER WITH DENTAL DIAGNOSTICS CAPABILITIES", which claimed priority to U.S. Provisional patent applications No. 62/367,607 (filed Jul. 27, 2016) and 62/477,387 (filed Mar. 27, 2017); U.S. patent application Ser. No. 15/662,250, filed on Jul. 27, 2017, titled "METHODS AND APPARATUSES FOR FORMING A THREE-DIMENSIONAL VOLUMETRIC MODEL OF A SUBJECT'S TEETH", which claimed priority to U.S. Provisional patent applications No. 62/367,607 (filed Jul. 27, 2016) and 62/477,387 (filed Mar. 27, 2017); and U.S. patent application Ser. No. 15/672,248, Filed on Aug. 8, 2017, and titled "METHODS FOR DENTAL DIAGNOSTICS", which claimed priority to U.S. Provisional patent applications No. 62/367,607 (filed Jul. 27, 2016) and 62/477,387 (filed Mar. 27, 2017). Each of these application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Many dental and orthodontic procedures can benefit from accurate three-dimensional (3D) descriptions of a patient's dentition and intraoral cavity. In particular, it would be helpful to provide a three-dimensional description of both the surface, and internal structures of the teeth, including the enamel and dentin, as well as caries and the general internal composition of the tooth volume. Although purely surface representations of the 3D surfaces of teeth have proven extremely useful in the design and fabrication of dental prostheses (e.g., crowns or bridges), and treatment plans, the ability to image internal structures, including the development of caries and cracks in the enamel and underlying dentin, would be tremendously useful, particularly in conjunction with a surface topographical mapping.

Historically, ionizing radiation (e.g., X-rays) have been used to image into the teeth. For example, X-Ray bitewing radiograms are often used to provide non-quantitative images into the teeth. However, in addition to the risk of ionizing radiation, such images are typically limited in their ability to show features and may involve a lengthy and expensive procedure to take. Some intraoral features such as soft tissues, plaque and soft calculus may not be easily visualized via x-ray because of their low density. Other techniques, such as cone beam computed tomography (CBCT) may provide tomographic images, but still require ionizing radiation.

Thus, it would be beneficial to provide methods and apparatuses, including devices and systems, such as intraoral scanning systems, that may be used to model a subject's tooth or teeth and include both external (surface) and internal (within the enamel and dentin) structures and composition using non-ionizing radiation. The model of the subject's teeth may be a 3D volumetric model or a panoramic image. In particular, it would be helpful to provide methods and apparatuses that may use a single apparatus to provide this capability.

SUMMARY OF THE DISCLOSURE

Described herein are methods and apparatuses for taking, using and displaying dental information including information extracted from three-dimensional (3D) volumetric models of a patient's dental arch. A 3D volumetric model may include surface (e.g., color) information as well as information on internal structure, such as near-infrared (near-IR) transparency values for internal structures including enamel and dentin. In some variations, the 3D volumetric scan may include or be derived from one or more other scanning modalities, including, but not limited to: optical coherence tomography (OCT), ultrasound (US), magnetic resonance imaging (MRI), X-ray, etc.

In particular, described herein are methods and user interfaces for displaying and manipulating (e.g., sectioning, marking, selecting sub-regions, etc.) 3D volumetric models. For example, methods and apparatuses for displaying images from 3D volumetric models are provided, including methods for generating sections though the 3D volumetric model, methods for showing both surface and internal structures, and methods for generating easy to interpret images from the 3D volumetric models, such as pseudo-x-ray images.

Also described herein are methods and apparatuses for marking and tracking regions of interest from a 3D volumetric model of a patient's dental arch. These methods may include automatically, manually or semi-automatically (e.g., with user approval or input) identifying one or more regions from within the 3D volumetric model to mark (including surface features and/or internal features of the dental arch); these regions may be regions in which a caries, crack or other irregularity has developed or may develop. Marked regions may be analyzed in greater detail, and may be tracked over time. Further, marked regions may modify the manner in which subsequent scanning is performed, e.g., by scanning marked regions at higher resolution. The regions of the volumetric model may correspond to one or more voxels, including contiguous voxel regions. These regions may be referred to herein as volumetric regions.

Also described herein are methods and apparatuses for using 3D volumetric models to improve or modify a dental procedure, including modifying treatment planning and/or modifying one or more dental device. For example, described herein are dental tools that include 3D volumetric scanning, or that may be operated in conjunction with 3D volumetric models (including robotic or automated control using 3D volumetric models). Methods of diagnosing one or more conditions (e.g., dental conditions) using a 3D volumetric model, and particularly using 3D volumetric models over time are also described.

A method of displaying images from a three-dimensional (3D) volumetric model of a patient's dental arch, the method comprising: collecting the 3D volumetric model of the patient's dental arch, wherein the 3D volumetric model includes surface color and shade values and near-infrared (near-IR) transparency values for internal structures within the dental arch; selecting, by a user, an orientation of a view of the 3D volumetric model to display; generating a two-dimensional (2D) view into the 3D volumetric using the selected orientation, including the patient's dental arch including a weighted portion of the surface color values and a weighted portion of the near-IR transparency of the internal structures; and displaying the 2D view.

For example, described herein are methods of displaying images from a three-dimensional (3D) volumetric model of a patient's dental arch. The method may include: receiving the 3D volumetric model of the patient's dental arch, wherein the 3D volumetric model includes surface color values and near-infrared (near-IR) transparency values for internal structures within the dental arch; generating a two-dimensional (2D) view through the 3D volumetric model including the patient's dental arch including both surface color values and the near-IR transparency of the internal structures. In any of the methods and apparatuses described herein, a 3D model (including a volumetric 3D model) may be displayed as a voxel view. Thus, the methods described herein may generate one or more voxel views in which each voxel may have a color (or hue) that corresponds to its density and/or translucently. Thus, an of the methods and apparatuses described herein may generate a 3D color map of all or some of the voxels of the 3D model (and display one or more 2D images derived from the 3D color view, such a sections, slices, projections, perspective views, transparent-views in which all or some of the 3D model is rendered transparent, etc.). In some variations, flagged regions (e.g., regions corresponding to one or more irregular regions, and/or regions, e.g., voxels that have changed over time, regions/voxels that should be removed, regions/voxels suspected to be problematic and etc., may be displayed as a 3D and/or 2D view.

Generating the two-dimensional (2D) view through the 3D volumetric may include: including in the 2D view, a weighted portion of the surface color values and a weighted portion of the near-IR transparency of the internal structures. Note that the near-IR transparency may be based on or otherwise calculated from near IR scattering or absorption of the material. The weighted portion of the surface color values may comprise a percentage of the full value of the surface color values, and the weighted portion of the near-IR transparency of the internal structures comprises a percentage of the full value of the near-IR transparency of the internal structures, wherein the percentage of the full value of the surface color values and the percentage of the full value of the near-IR transparency of the internal structures adds up to 100%.

In some variations, the method also includes adjusting, by a user, or in response to user input, the weighted portion of the surface color values and/or the near-IR transparency of the internal structures.

Any of these methods may include the step of scanning the patient's dental arch with an intraoral scanner.

Generating the 2D view may comprise sectioning the 3D volumetric model in a plane through the 3D volumetric model. The user may select a section though the 3D volumetric model to display, and/or an orientation of the 2D view.

For example, a method of displaying images from a three-dimensional (3D) volumetric model of a patient's dental arch may include: receiving the 3D volumetric model of the patient's dental arch, wherein the 3D volumetric model includes surface color values and near-infrared (near-IR) transparency values for internal structures within the dental arch; selecting, by a user or in response to user input, a section though the 3D volumetric model to display; generating a two-dimensional (2D) view through the 3D volumetric using the selected section, including the patient's dental arch, and possibly also including a weighted portion of the surface color values and a weighted portion of the near-IR transparency of the internal structures; and displaying the 2D view.

A method of displaying images from a three-dimensional (3D) volumetric model of a patient's dental arch may include: collecting the 3D volumetric model of the patient's dental arch, wherein the 3D volumetric model includes surface values and near-infrared (near-IR) transparency values for internal structures within the dental arch; generating a two-dimensional (2D) view into the 3D volumetric model including the patient's dental arch including both surface values and the near-IR transparency of the internal structures; and displaying the 2D view.

A method of tracking a region of a patient's dental arch over time may include: receiving a first three-dimensional (3D) volumetric model of the patient's dental arch, wherein the 3D volumetric model includes surface color values and near-infrared (near-IR) transparency values for internal structures within the dental arch; identifying a region within the 3D volumetric model to be marked; flagging the identified region; and displaying one or more images of the 3D volumetric model indicating the marked region.

For example, a method of tracking a region of a patient's dental arch over time, the method comprising: collecting a first three-dimensional (3D) volumetric model of the patient's dental arch, wherein the 3D volumetric model includes surface values and near-infrared (near-IR) transparency values for internal structures within the dental arch; identifying a region of the 3D volumetric model; flagging the identified region; collecting a second 3D volumetric model of the patient's dental arch; and displaying one or more images marking, on the one or more images, a difference between the first 3D volumetric model and the second 3D volumetric model at the flagged region.

Identifying the region may comprise automatically identifying using a processor. For example, automatically identifying may comprise identifying a region having a possible defects including: cracks and caries. Identifying the region having a possible defect may comprise comparing a near-IR transparency value of a region within the 3D model to a threshold value. Automatically identifying may comprise identifying a surface color value outside of a threshold range. Automatically identifying may comprise segmenting the 3D volumetric model to identify enamel regions and identifying regions having enamel thicknesses below a threshold value. Flagging the identified region may comprise automatically flagging the identified regions. Flagging the identified region may comprise manually confirming the identified region for flagging.

Any of these methods may include receiving a second 3D volumetric model of the patient's dental arch and displaying a difference between the first 3D volumetric model and the second 3D volumetric model at the marked region.

Further, any of these methods may include pre-scanning or re-scanning the patient's dental arch wherein the flagged region is scanned at a higher resolution or in other scanning modalities than un-flagged regions.

For example, a method of tracking a region of a patient's dental arch over time may include: receiving a first three-dimensional (3D) volumetric model of the patient's dental arch, wherein the 3D volumetric model includes surface color values and near-infrared (near-IR) transparency values for internal structures within the dental arch; identifying, using an automatic process, a region within the 3D volumetric model to be marked; flagging the identified regions; receiving a second 3D volumetric model of the patient's dental arch; and displaying a difference between the first 3D volumetric model and the second 3D volumetric model at the marked region. In some instances, the second 3D volumetric model of the patient's dental arch may be from a scan of the patient at a subsequent visit to the dental practitioner's office at a later date.

Thus, a method of tracking a region of a patient's dental arch over time may include: collecting a first three-dimensional (3D) volumetric model of the patient's dental arch taken at a first time, wherein the 3D volumetric model includes surface color values and near-infrared (near-IR) transparency values for internal structures within the dental arch; identifying, using an automatic process, a region within the 3D volumetric model to be flagged; flagging the identified regions; collecting a second 3D volumetric model of the patient's dental arch taken at a separate time; and displaying a difference between the first 3D volumetric model and the second 3D volumetric model at the flagged region.

Also described herein are methods of displaying pseudo x-ray images from a three-dimensional (3D) volumetric model of a patient's dental arch. For example, a method may include: receiving the 3D volumetric model of the patient's dental arch, wherein the 3D volumetric model includes near-infrared (near-IR) transparency values for internal structures within the dental arch; generating a two-dimensional (2D) view through the 3D volumetric including the patient's dental arch including the near-IR transparency of the internal structures; mapping the near-IR transparency of the internal structures in the 2D view to a pseudo-X-ray density in which the near-IR transparency values are inverted in value; and displaying the mapped pseudo-X-ray density. Generating the 2D view may comprise sectioning the 3D volumetric model in a plane through the 3D volumetric model. The 3D volumetric model may include surface information.

For example, a method of displaying pseudo x-ray images from a three-dimensional (3D) volumetric model of a patient's dental arch may include: collecting the 3D volumetric model of the patient's dental arch, wherein the 3D volumetric model includes near-infrared (near-IR) transparency values for internal structures within the dental arch; generating a two-dimensional (2D) view into the 3D volumetric model including the patient's dental arch including the near-IR transparency of the internal structures; mapping the near-IR transparency of the internal structures in the 2D view to a pseudo-X-ray density in which the pseudo-X-ray density values in the 2D view are based on the near-IR transparency values that are inverted in value; and displaying the mapped pseudo-X-ray density.

Any of these methods may include identifying a sub-region from the 3D volumetric model prior to generating the 2D view, wherein the 2D view comprises a view of the identified sub-region. The method may also include segmenting the 3D volumetric model into a plurality of teeth, wherein generating the 2D view may comprise a 2D view including just one of the identified teeth.

Mapping the near-IR transparency may include inverting the near-IR transparency values so that enamel within the 2D view is brighter than dentin within the 2D view.

A method of displaying pseudo x-ray images from a three-dimensional (3D) volumetric model of a patient's dental arch may include: receiving the 3D volumetric model of the patient's dental arch, wherein the 3D volumetric model includes surface features and near-infrared (near-IR) transparency values for internal structures within the dental arch in which enamel is more transparent than dentin; generating a two-dimensional (2D) view through the 3D volumetric including the patient's dental arch including the near-IR transparency of the internal structures including dentin and enamel; mapping the near-IR transparency of the internal structures in the 2D view to a pseudo-X-ray density in which the near-IR transparency values are inverted in value so that the enamel is brighter than the dentin; and displaying the mapped pseudo-X-ray density.

For example, a method of displaying pseudo x-ray images from a three-dimensional (3D) volumetric model of a patient's dental arch may include: collecting the 3D volumetric model of the patient's dental arch, wherein the 3D volumetric model includes surface features and near-infrared (near-IR) transparency values for internal structures within the dental arch in which enamel is more transparent than dentin; generating a two-dimensional (2D) view into the 3D volumetric including the patient's dental arch including the near-IR transparency of the internal structures including dentin and enamel; mapping the near-IR transparency of the internal structures in the 2D view to a pseudo-X-ray density in which the near-IR transparency values are inverted in value so that the enamel is brighter than the dentin; and displaying the mapped pseudo-X-ray density.

Also described herein are methods and apparatuses for virtually reviewing (e.g., virtually sectioning, virtually scanning, virtually examining), in real time, a volumetric model of the patient's dental arch(s). These apparatuses may include non-transitory, machine-readable tangible medium storing instructions for causing one or more machines to execute operations for performing any of the methods described herein. In particular, any of these methods and apparatuses may operate on a data set that includes both a 3D model of the patient's dental arch, or in some variations, both of the patient's dental arches. The 3D model may be, but is not limited to, a 3D volumetric model; in some variation the 3D model is a 3D surface model of the arch. This data set may also include a plurality of images of the dental arch, taken from different positions relative to the dental arch, such as different angles between the plane of the image and the dental arch and different sub-regions of the dental arch. Some of these images may be taken from the occlusal surface, some from the gingival side, and some from the lingual side. In some variations the images may be the same (or a subset of) the images used to form the 3D model of the teeth. The data set may include multiple images taken from the same, or nearly the same, region of the dental arch and angle relative to the dental arch. In some variations, the data set may include sets of two or more images (e.g., pairs of images) each taken at approximately the same region of the dental arch and at the same angle relative to the dental arch but using different imaging techniques (e.g., different imaging techniques, such as visible light, IR/near-IR, florescence, X-ray, ultrasound, etc.).

For example, a method may include: displaying a three-dimensional (3D) model of a patient's dental arch; displaying a viewing window over at least a portion of the 3D model of the patient's dental arch; allowing a user to change a relative position between the viewing window and the 3D model of the patient's dental arch; and continuously, as the user changes the relative positions between the viewing window and the 3D model of the patient's dental arch: identifying, from both the 3D model of the patient's dental arch and a plurality of images of a patient's dental arch taken from different angles and positions relative to the patient's dental arch, an image taken at an angle and position that approximates a relative angle and position between the viewing window relative and the 3D model of the patient's dental arch; and displaying the identified image taken at the angle and position that approximates the angle and position between the viewing window relative to the 3D model of the patient's dental arch.

Any of the methods described herein, a data set may include the 3D model of the patient's dental arch and a plurality of images of a patient's dental arch taken from different angles and positions relative to the patient's dental arch. A data set may also or alternatively includes metadata associated with each (or each set) of the figures indicating the angle and/or region of the dental arch at which the image was taken. Additional metadata may be included (e.g., indicating a distance from the dental arch, indicating exposure time, indicating that the image is an average of other images, a quality metric for the image, etc.).

For example, described herein are methods for displaying a 3D model (e.g., surface 3D model) of the patient's teeth and/or volumetric model of the patient's teeth) that a user can virtually scan in greater detail by moving a viewing window over the 3D model of the dental arch. For example, described herein are methods including: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between a plane of the viewing window and the patient's dental arch, and a portion of the dental arch adjacent to the viewing window; and continuously, as the user changes the relative positions between the viewing window and the 3D model of the patient's dental arch: identifying, from both the 3D model of the patient's dental arch and a plurality of images of a patient's dental arch (e.g., in some variations from a data set comprising both the 3D model of the patient's dental arch and a plurality of images of a patient's dental arch), wherein each image is taken from a different angle and position relative to the patient's dental arch, an image taken at an angle and position that approximates the relative angle and position between the viewing window relative and the 3D model of the patient's dental arch; and displaying the identified image taken at the angle and position that approximates the angle and position of the viewing window relative to the displayed 3D model of the patient's dental arch.

For example, a method may include: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the patient's dental arch relative and a plane of the viewing window, and a portion of the dental arch adjacent to the viewing window; and continuously, as the user changes the relative position between the viewing window and the 3D model of the patient's dental arch: identifying, from both the 3D model of the patient's dental arch and a plurality of pairs of images of a patient's dental arch (e.g., optionally from a data set comprising both the 3D model of the patient's dental arch and a plurality of images of a patient's dental arch), wherein each pair of the plurality of pairs includes a first imaging wavelength and a second imaging wavelength each taken at the same angle and position relative to the patient's dental arch, a pair of images taken at an angle and position that approximate the angle and position of the viewing window relative to the displayed 3D model of the patient's dental arch; and displaying at least one of the identified pair of images taken at the angle and position that approximate the angle and position of the viewing window relative to the displayed 3D model of the patient's dental arch.

The methods and apparatuses described herein can be used with a 3D model that is a surface model or any representation of the patient's dental arch(s). It may be, but does not have to be, a 3D volumetric model of the patient's teeth, e.g., constructed from images (e.g., the plurality of images of a patient's dental arch taken from different angles and positions relative to the patient's dental arch). The model may be representative of the patient's actual dentition, abstracted from the patient's dentition, or generic.

As described herein, a method may include: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, both the 3D model of the patient's dental arch and a plurality of near-IR images of a patient's dental arch (e.g., from a data set comprising both the 3D model of the patient's dental arch and a plurality of images of a patient's dental arch), wherein each near-IR image is taken from a different angle and position relative to the patient's dental arch, a near-IR image taken at an angle and position that approximates the relative angle and position between the viewing window relative and the 3D model of the patient's dental arch; and displaying the identified near-IR image taken at the angle and position that approximates the angle and position of the viewing window relative to the displayed 3D model of the patient's dental arch.

In any of these examples, the images may be images taken with a penetrating modality, such as with a near-IR. For example, described herein are methods including: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, from a data set comprising both the 3D model of the patient's dental arch and a plurality of near-IR images of a patient's dental arch, wherein each near-IR image is taken from a different angle and position relative to the patient's dental arch, a near-IR image taken at an angle and position that approximates the relative angle and position between the viewing window relative and the 3D model of the patient's dental arch; and displaying the identified near-IR image taken at the angle and position that approximates the angle and position of the viewing window relative to the displayed 3D model of the patient's dental arch.

Any of these methods may also include identifying and displaying multiple images taken at the same angle and position relative to the dental arch. For example, the images may be both a visible light image and a penetrative image (such as an IR/near-IR image, etc.). For example, described herein are: methods comprising: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the patient's dental arch relative and a plane of the viewing window, and a portion of the dental arch adjacent to the viewing window; and continuously, as the user changes the relative position between the viewing window and the 3D model of the patient's dental arch: identifying, from a data set comprising both the 3D model of the patient's dental arch and a plurality of pairs of images of a patient's dental arch, wherein each pair of the plurality of pairs includes a first imaging wavelength and a second imaging wavelength each taken at the same angle and position relative to the patient's dental arch, a pair of images taken at an angle and position that approximate the angle and position of the viewing window relative to the displayed 3D model of the patient's dental arch; and displaying the identified pair of images taken at the angle and position that approximate the angle and position of the viewing window relative to the displayed 3D model of the patient's dental arch.

In any of these methods, identifying may comprise determining a plurality images that approximate the relative angle and position between the viewing window relative and the 3D model of the patient's dental arch and averaging the plurality to form the identified image. For example, there may be multiple images in the data set taken at approximately (e.g., within +/−0.1%, 0.5%, 1%, 2%, 3%, 4%, 5%, 7%, 10%, 15%, 20%, etc.) of the same angle and approximately (e.g., within +/−0.1%, 0.5%, 1%, 2%, 3%, 4%, 5%, 7%, 10%, 15%, 20%, etc.) of the same region of the dental arch; these similar images may be combined to form an average image that may be better than the individual images.

In general, identifying one or more images taken at an angle and position that approximates the relative angle and position between the viewing window relative and the 3D model of the patient's dental arch may be identifying within an acceptable spatial range. For example, an image that was taken at between +/−a few degrees of the same angle (e.g., +/−0.1 degree, 0.2 degree, 0.3 degrees, 0.4 degrees, 0.5 degrees, 0.6 degrees, 1 degree, 1.2 degrees, 1.5 degrees, 1.7 degrees, 1.8 degrees, 2 degrees, 2.2 degrees, 2.5 degrees, 3 degrees, 3.2 degrees, 3.5 degrees, 4 degrees, 5 degrees, etc.) as the plane of the viewing widow and within +/−a range of distance of the dental arch region over which the viewing window is positioned (e.g., +/−0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.5 mm, 1.7 mm, 2.0 mm, 2.2 mm, 2.5 mm, etc.).

Any of these methods may include receiving, in a processor, the data set. The data set may be received directly from an intraoral scanner, and/or stored and retrieved. In some variations the data set may be transmitted and received by the processor, in some variations the processor may read the data set from a memory (e.g., a data store) connected to the processor.

In general, any of these methods may include displaying the viewing window over a portion of the 3D model of the patient's dental arch. The viewing window may be any shape or size, such as a circle, oval, triangle, rectangle, or other polygon. For example, the viewing window may be a loop through which the portion of the 3D model of the patient's dental arch may be viewed. The viewing angle may allow the dental arch to be visualized through at least a portion of the viewing window. The viewing window may be smaller than the dental arch. In some variations the viewing window may be made larger or smaller by the user.

Typically these methods may include displaying via a user interface. For example, the user interface may display on a screen or screens the dental arch 3D model, the viewing window, and/or the image(s) corresponding to the view thorough the viewing window of the dental arch. The user may (e.g., by manipulating the user interface, e.g., via a control such as a mouse, keyboard, touchscreen, etc.) move the viewing window and dental arch independently. This movement, and the image(s) determined to correspond to the image though the viewing window of the region and angle of the viewing window relative to the dental arch, may be displayed in real time, as the user moves the viewing window and/or dental arch relative to each other.

For example, allowing the user to change the relative position between the viewing window and the 3D model of the patient's dental arch may include separately controlling the angle and/or rotation of the 3D model of a patient's dental arch and the portion of the dental arch adjacent to the viewing window. In some variations, allowing the user to change the relative position between the viewing window and the 3D model of the patient's dental arch may comprise allowing the user to move the viewing window over the 3D model of the dental arch.

As mentioned, any of the images identified to as taken from an angle and position corresponding to the angle and position of the viewing window as it is moved over and/or around the dental arch (or as the dental arch is moved relative to the viewing window) may be any one or more modalities. Thus, for example, identifying an image that approximates the relative angle and position between the viewing window relative and the 3D model of the patient's dental arch may include identifying one of: a visible light image, an infrared image, and a florescent image.

Displaying the identified image(s) that approximates the angle and position of the viewing window relative to the displayed 3D model may comprise displaying the identified image in a window adjacent or overlapping with the display of the 3D model of the patient's dental arch. For example, the images may be displayed on a screen alongside the 3D model of the dental arch; a the user moves the dental arch and/or imaging window, the image(s) may be shown in one or more windows changing in real time or near real-time to reflect the relative position of the 3D model of the dental arch and the viewing window.

Also described herein are non-transitory, machine-readable tangible medium storing instructions for causing one or more machines to execute operations for performing any of the methods described herein, including virtually reviewing a patient's dental arch. For example, a non-transitory, machine-readable tangible medium may store instructions for causing one or more machines to execute operations for virtually reviewing a patient's dental arch including: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, from a data set comprising both the 3D model of the patient's dental arch and a plurality of images of a patient's dental arch, wherein each image is taken from a different angle and position relative to the patient's dental arch, an image taken at an angle and position that approximates the relative angle and position between the viewing window relative and the 3D model of the patient's dental arch; and displaying the identified image taken at the angle and position that approximates the angle and position of the viewing window relative to the displayed 3D model of the patient's dental arch.

For example, a non-transitory, machine-readable tangible medium storing instructions for causing one or more machines to execute operations for virtually reviewing a patient's dental arch, comprising: displaying a three-dimensional (3D) model of a patient's dental arch; displaying a viewing window over a portion of the 3D model of the patient's dental arch; allowing a user to change a relative position between the viewing window and the 3D model of the patient's dental arch, including one or more of: an angle between the viewing window and the patient's dental arch, and a portion of the dental arch adjacent to the viewing window; and continuously, as the user changes the relative positions between the viewing window and the 3D model of the patient's dental arch: identifying, from a data set comprising both the 3D model of the patient's dental arch and a plurality of images of a patient's dental arch, wherein each image is taken from a different angle and position relative to the patient's dental arch, an image taken at an angle and position that approximates the relative angle and position between the viewing window relative and the 3D model of the patient's dental arch; and displaying the identified image taken at the angle and position that approximates the angle and position of the viewing window relative to the displayed 3D model of the patient's dental arch.

Also described herein are intraoral scanning systems that are configured to perform the methods described herein. For example, an intraoral scanning system may include a hand-held wand having at least one image sensor and a light source configured to emit light at a spectral range within near-infrared (near-IR) range of wavelengths; a display output (e.g., a visual output such as a monitor, screen, virtual reality interface/augmented reality interface, etc.); a user input device (e.g., any control for receiving and transmitting user input, such as, but not limited to: a keyboard, button, joystick, touchscreen, etc. The display output and the user input device may be the same touchscreen); and one or more processors operably connected to the hand-held wand, display and user input device, the one or more processors configured to: display a three-dimensional (3D) model of a patient's dental arch on the display output; display a viewing window over a portion of the 3D model of the patient's dental arch on the display output; change a relative position between the viewing window and the 3D model of the patient's dental arch based on input from the user input device; identify, from both the 3D model of the patient's dental arch and a plurality of images of the patient's dental arch taken from different angles and positions relative to the patient's dental arch, a near-infrared (near-IR) image taken at an angle and position that approximates a relative angle and position between the viewing window relative and the 3D model of the patient's dental arch; and display the identified near-IR image taken at the angle and position that approximates the angle and position between the viewing window relative to the 3D model of the patient's dental arch.

The one or more processors of the intraoral scanning system may be configured to receive the plurality of images of the patient's dental arch taken from different angles and positions relative to the patient's dental arch. For example, the images may be taken by the image sensor(s) on the hand-held wand and transmitted to the one or more processors and/or stored in a memory that is accessed by the one or more processors. The system may also include a controller coordinating the activity of the one or more processors, the wand, and the display output (and user input device). The controller may display the images and/or a 3D model constructed from the images as a user operates the hand-held want to take images at different locations and/or angles relative to the patient's dental arch(es).

The one or more processors may be configured to continuously identify the near-IR image and display the identified near-IR image as the user changes the relative positions between the viewing window and the 3D model of the patient's dental arch. Thus, as the user (using the user input) adjusts the position of the viewing window (e.g., loop) relative to the 3D model of the patient's dental arch on the display output (or, equivalently, adjusts the position of the 3D model of the dental arch on the display output relative to the viewing window), the one or more processors may determine and display a near-IR image of the patient's teeth that most closely approximates the relative positions between the viewing window and the 3D model of the patient's dental arch.

The near-IR image is either one of the images taken by the hand-held wand or an average of the images taken by the hand-held wand. Any of the apparatuses (e.g., intraoral scanning systems) described herein may also determine and/or store the positions and/or orientation of the hand-held wand as it is being operated, and this information may be stored with the image(s) taken from this position. For example, the hand-held wand may include one or more accelerometers. For example, the one or more processors may be configured to identify the near-IR image taken at an angle and position that approximates a relative angle and position between the viewing window relative and the 3D model of the patient's dental arch by determining a plurality images that approximate the relative angle and position between the viewing window relative and the 3D model of the patient's dental arch and averaging the plurality to form the identified near-IR image.

As mentioned, the one or more processors may be configured to change, on the display output, the relative position between the viewing window and the 3D model of the patient's dental arch based on input from the user input device. Specifically, the one or more processor may be configured to change, based on user input into user input device, one or more of: an angle between a plane of the viewing window and the patient's dental arch, and a portion of the dental arch adjacent to the viewing window (e.g., in some variations, visible through the viewing window). As discussed above, the viewing window may be a loop (e.g., circular, oval, square, etc.) through which the 3D model is visible). Thus, the one or more processors may be configured to display the viewing window over a portion of the 3D model of the patient's dental arch comprises displaying as a loop through which the portion of the 3D model of the patient's dental arch may be viewed. The viewing window may be moved and positioned over (including changing which side of the dental arch (buccal, occlusal, lingual, or between these, including moving in x, y, z and/or in rotation, e.g., pitch, roll, yaw) the viewing window is positioned over and/or the 3D model of the patient's teeth may be moved (e.g., rotating in pitch, yaw, roll, moving in x, y, z, etc.). Thus, the one or more processors may be configured to change the relative position between the viewing window and the 3D model of the patient's dental arch based on input from the user input device by changing one or more of: the angle of the 3D model of a patient's dental arch relative to the viewing window (which is equivalent to the angle of the viewing window relative to the 3D model of the patient's dental arch), the rotation of the 3D model of a patient's dental arch relative to the viewing window (which is equivalent to the rotation of the viewing window relative to the 3D model of a patient's dental arch), and the portion of the dental arch adjacent to the viewing window (e.g., the portion of the 3D model visible through the viewing window). For example, the one or more processors may be configured to change the relative position between the viewing window and the 3D model of the patient's dental arch based on input from the user input device by changing the position of the viewing window over the 3D model of the dental arch.

The one or more processors may be configured to identify from both the 3D model of the patient's dental arch and the plurality of images of the patient's dental arch taken from different angles and positions relative to the patient's dental arch, a second image that approximates the relative angle and position between the viewing window relative and the 3D model of the patient's dental arch that is one or more of: a visible light image and a florescent image; and wherein the one or more processors is configured to display the second image concurrently with the near-IR image.

Also described herein are methods of automatically, semi-automatically/semi-manually or manually identifying and grading features by coordinating across multiple imaging modalities. For example, a dental diagnostic method may include: identifying a dental feature in a first record, the first record comprising a plurality of images of a patient's dental arch taken first imaging modality; correlating the first record with a model of the patient's dental arch; identifying, using the model of the patient's dental arch, a region of the dental arch corresponding to the dental feature in one or more different records, wherein each record of the one or more different records is taken with a different imaging modality than the first imaging modality and wherein each of the one or more different records is correlated with the model of the patient's dental arch; determining a confidence score for the dental feature based on the identified regions corresponding to the dental feature in the one or more different records; and displaying the dental feature when the confidence score for the dental feature is above a threshold.

A dental diagnostic method may include: identifying a dental feature in a first record, the first record comprising a plurality of images of a patient's dental arch taken first imaging modality; correlating the first record with a three-dimensional (3D) volumetric model of the patient's dental arch; flagging the dental feature on the 3D volumetric model; identifying, using the model of the patient's dental arch, a region of the dental arch corresponding to the dental feature in one or more different records, wherein each record of the one or more different records is taken with a different imaging modality than the first imaging modality and wherein each of the one or more different records is correlated with the model of the patient's dental arch; determining or adjusting a confidence score for the dental feature based on the identified regions corresponding to the dental feature in the one or more different records; and displaying the dental feature and an indicator of the confidence score for the dental feature when the confidence score for the dental feature is above a threshold.

In any of these methods (or systems for performing them) the dental feature may comprise one or more of: cracks, gum recess, tartar, enamel thickness, pits, caries, pits, fissures, evidence of grinding, and interproximal voids.

Displaying may comprise displaying the dental feature and an indicator of the confidence score for the dental feature.

Correlating the first record with the model of the patient's dental arch may comprise correlating the first record with a three-dimensional (3D) volumetric model of the patient's dental arch. Any of these methods (or systems for performing them) may include flagging the dental feature on the model of the patient's dental arch, and/or collecting the dental feature, including the location of the dental feature, and one or more of: the type of dental feature and a confidence score for the dental feature.

Determining the confidence score may comprise adjusting the confidence score for the dental feature based on the identified regions corresponding to the dental feature in the one or more different records.

In any of these methods or systems, identifying the dental feature may comprise automatically identifying the dental feature.

For example, a dental diagnostic method may include: identifying one or more actionable dental features from one or more records of a plurality of records, wherein each record comprises a plurality of images of a patient's dental arch each taken using an imaging modality, further wherein each record of the plurality of records is taken at a different imaging modality; mapping the actionable dental feature to a corresponding region of the one or more records; recording the one or more actionable dental features, including recording a location of the actionable dental feature; adjusting or determining a confidence score for the one or more actionable dental features based on the corresponding region of the one or more records; and displaying the one or more actionable dental features when the confidence score of the one or more actionable dental features is above a threshold. As mentioned above, the one or more actionable feature comprises one or more of: cracks, gum recess, tartar, enamel thickness, pits, caries, pits, fissures, evidence of grinding, and interproximal voids.

Displaying may comprise displaying the one or more actionable dental features and an indicator of the confidence score for the dental feature. Mapping the actionable dental feature to the corresponding region of the one or more records may comprise correlating the first record with a three-dimensional (3D) volumetric model of the patient's dental arch. Recording the one or more actionable dental features may comprise marking the dental feature on the 3D volumetric model of the patient's dental arch. Identifying the dental feature may comprise automatically identifying the dental feature.

Also described herein are systems for performing any of the methods described herein. For example, a system may include: one or more processors; and a memory coupled to the one or more processors, the memory configured to store computer-program instructions, that, when executed by the one or more processors, perform a computer-implemented method comprising: identifying a dental feature in a first record, the first record comprising a plurality of images of a patient's dental arch taken first imaging modality; correlating the first record with a model of the patient's dental arch; identifying, using the model of the patient's dental arch, a region of the dental arch corresponding to the dental feature in one or more different records, wherein each record of the one or more different records is taken with a different imaging modality than the first imaging modality and wherein each of the one or more different records is correlated with the model of the patient's dental arch; determining a confidence score for the dental feature based on the identified regions corresponding to the dental feature in the one or more different records; and displaying the dental feature when the confidence score for the dental feature is above a threshold.

Also described herein are methods and apparatuses (e.g., systems) for tracking one or more regions (e.g., tagged or flagged regions) across different imaging modalities and/or over time. For example, a method of tracking a dental feature across different imaging modalities may include: collecting a first three-dimensional (3D) volumetric model of the patient's dental arch, wherein the 3D volumetric model of the patient's dental arch includes surface values and internal structures within the dental arch; identifying a region of the patient's dental arch from a first record of a plurality of records, wherein each record comprises a plurality of images of a patient's dental arch each taken using an imaging modality, further wherein each record of the plurality of records is taken at a different imaging modality; flagging the identified region in a corresponding region of the 3D volumetric model of the patient's dental arch; correlating the flagged region with each of records of the plurality of records by correlating the 3D volumetric model of the patient's dental arch with each of the records of the plurality of records; and saving, displaying and/or transmitting images including the region of the patient's dental arch. The region of the patient's dental arch may comprise a dental feature comprises one or more of: cracks, gum recess, tartar, enamel thickness, pits, caries, pits, fissures, evidence of grinding, and interproximal voids.

Saving, displaying and/or transmitting may comprise displaying the regions of the patient's dental arch. Any of these methods may include flagging the dental feature on the 3D volumetric model. Identifying the region of the patient's dental arch may comprise automatically identifying the region of the patient's dental arch.

A system for tracking one or more regions (e.g., tagged or flagged regions) across different imaging modalities and/or over time may include: one or more processors; a memory coupled to the one or more processors, the memory configured to store computer-program instructions, that, when executed by the one or more processors, perform a computer-implemented method comprising: collecting a first three-dimensional (3D) volumetric model of the patient's dental arch, wherein the 3D volumetric model of the patient's dental arch includes surface values and internal structures within the dental arch; identifying a region of the patient's dental arch from a first record of a plurality of records, wherein each record comprises a plurality of images of a patient's dental arch each taken using an imaging modality, further wherein each record of the plurality of records is taken at a different imaging modality; flagging the identified region in a corresponding region of the 3D volumetric model of the patient's dental arch; correlating the flagged region with each of records of the plurality of records by correlating the 3D volumetric model of the patient's dental arch with each of the records of the plurality of records; and saving, displaying and/or transmitting images including the region of the patient's dental arch.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 illustrates one method of generating internal structure (or pseudo x-ray) images from a volumetric data.

In FIG. 5A, virtual section is pseudo-colored to show enamel; in FIG. 5B, the virtual section is pseudo-colored to show dentin.

FIG. 8A is an example of a display tracking gingival recession over time in using a 3D volumetric model as described herein. FIG. 8B shows an enlarged view of region B in FIG. 8A showing the later time.

FIG. 9A show an example of a 3D volumetric model of a patient's upper jaw (showing teeth and gingiva), from a top view. FIG. 9B shows the same 3D volumetric model, showing the internal features, including the more transparent enamel and the less transparent dentin. The 3D volumetric model may be manipulated to show more or less of the surface and/or internal structures. FIGS. 9C-9G illustrate progressively more transparent views or a region ("C") of the 3D volumetric model of FIG. 9A. FIG. 9C show a 2D image extracted from a region of the 3D volumetric model showing just the outer surface of the teeth (e.g., 100% of the color/outer surface image, 0% near-IR/internal volume). FIG. 9D shows the same region as FIG. 9C, combining the outer surface (color) image and the internal (near-IR based) image (e.g., 75% of the color/outer surface image, 25% near-IR/internal volume). FIG. 9E shows the same region as FIG. 9C, combining the outer surface (color) image and the internal (near-IR based) image (e.g., 50% of the color/outer surface image, 50% near-IR/internal volume). FIG. 9F shows the same region as FIG. 9C, combining the outer surface (color) image and the internal (near-IR based) image (e.g., 25% of the color/outer surface image, 75% near-IR/internal volume). FIG. 9G shows the same region as FIG. 9C showing just the internal (near IR based) image of the teeth (e.g., 0% of the color/outer surface image, 1000% near-IR/internal volume).

FIGS. 11A-11C illustrate another example of a method of displaying 3D volumetric image information by mixing it with surface (non-penetrative) information. FIG. 11A shows a visible light image of a region of a patient's dental arch taken with a scanner that is also configured to take penetrative (near-IR) scans). FIG. 11B show a volumetric model of the reconstructed 3D volumetric model of a patient's tooth showing internal dentin and enamel. Features not visible on the surface scan are apparent in the volumetric scan, including a caries and a bubbled region within the enamel. FIG. 11C shows a hybrid image in which the 3D volumetric image has been combined with the surface scan, showing both surface and internal structures, including the carries and the bubbled region.

In FIG. 14B the image window show a light image of the corresponding region of the dental arch.

In FIG. 14C the image window show a near-IR image of the corresponding region of the dental arch.

DETAILED DESCRIPTION

Figures 1A, 1B:
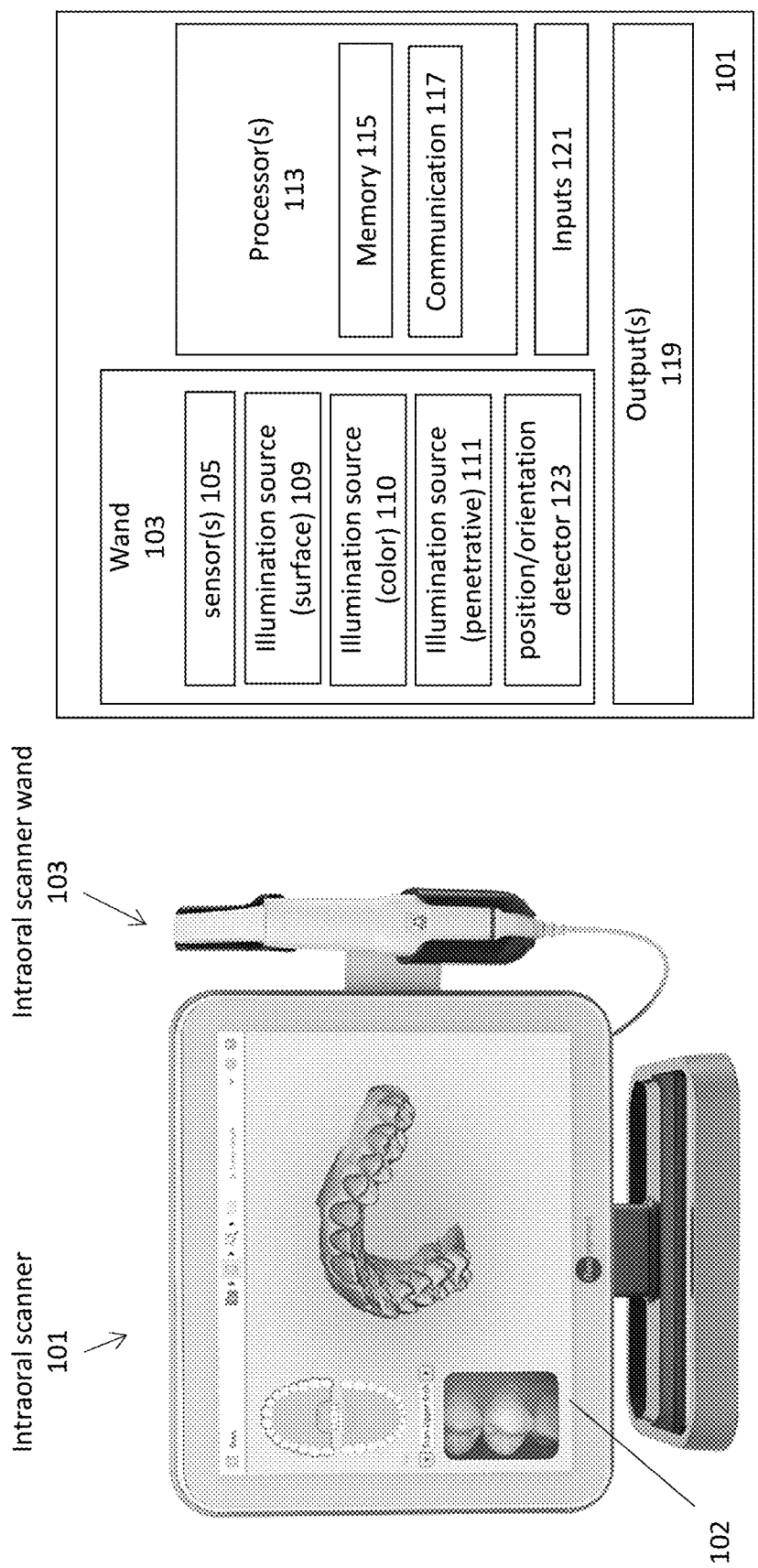
FIG. 1A illustrates one example of a 3D (color) intraoral scanner that may be adapted for used as described herein to generate a model of subject's teeth having both surface and internal features.
FIG. 1B schematically illustrates an example of an intraoral scanner configured to generate a model of subject's teeth having both surface and internal features.

Described herein are methods and apparatuses (e.g., devices and systems) that apply scans of both external and/or internal structures of teeth. These methods and apparatuses may generate and/or manipulate a model of a subject's oral cavity (e.g., teeth, jaw, palate, gingiva, etc.) that may include both surface topography and internal features (e.g., dentin, dental filling materials (including bases and linings), cracks and/or caries). Apparatuses for performing both surface and penetrative scanning of the teeth may include intraoral scanners for scanning into or around a subject's oral cavity and that are equipped with a light source or light sources that can illuminate in two or more spectral ranges: a surface-feature illuminating spectral range (e.g., visible light) and a penetrative spectral range (e.g. IR range, and particularly "near-IR," including but not limited to 850 nm). The scanning apparatus may also include one or more sensors for detecting the emitted light and one or more processors for controlling operation of the scanning and for analyzing the received light from both the first spectral range and the second spectral range to generate a model of the subject's teeth including the surface of the teeth and features within the teeth, including within the enamel (and/or enamel-like restorations) and dentin. The generated mode may be a 3D volumetric model or a panoramic image.

As used herein, a volumetric model may include a virtual representation of an object in three dimensions in which internal regions (structures, etc.) are arranged within the volume in three physical dimensions in proportion and relative relation to the other internal and surface features of the object which is being modeled. For example, a volumetric representation of a tooth may include the outer surface as well as internal structures within the tooth (beneath the tooth surface) proportionately arranged relative to the tooth, so that a section through the volumetric model would substantially correspond to a section through the tooth, showing position and size of internal structures; a volumetric model may be section from any (e.g., arbitrary) direction and correspond to equivalent sections through the object being modeled. A volumetric model may be electronic or physical. A physical volumetric model may be formed, e.g., by 3D printing, or the like. The volumetric models described herein may extend into the volume completely (e.g., through the entire volume, e.g., the volume of the teeth) or partially (e.g., into the volume being modeled for some minimum depth, e.g., 2 mm, 3 mm, 4 mm, 5 mm, 6 mm, 7 mm, 8 mm, 9 mm, 10 mm, 12 mm, etc.).

The methods described herein typically include methods for generating a model of a subject's teeth typically generating a 3D model or rendering of the teeth that include both surface and internal features. Non-ionizing methods of imaging and/or detecting internal structures may be used, such as taking images using a penetrating wavelength to view structures within the teeth by illuminating them using one or more penetrative spectral ranges (wavelengths), including trans-illumination (e.g., illuminating from one side and capturing light from the opposite side after passing through the object), and/or small-angle penetration imaging (e.g., reflective imaging, capturing light that has been reflected/scattered from internal structures when illuminating with a penetrating wavelength). In particular, multiple penetration images may be taken from the same relative position. Although traditional penetration imaging techniques (e.g., trans-illumination) may be used, in which the angle between the light emitter illumination direction and the detector (e.g., camera) view angle is 90 degrees or 180 degrees, also described herein are methods and apparatuses in which the angle is much smaller (e.g., between 0 degrees and 25 degrees, between 0 degrees and 20 degrees, between 0 degrees and 15 degrees, between 0 degrees and 10 degrees, etc.). Smaller angles (e.g., 0-15°) may be particularly beneficial because the illumination (light source) and sensing (detector(s), e.g., camera(s), etc.) may be closer to each other, and may provide a scanning wand for the intraoral scanner that can be more easily positioned and moved around a subject's teeth. These small-angle penetration images and imaging techniques may also be referred to herein as reflective illumination and/or imaging, or as reflective/scattering imaging. In general penetrating imaging may refer to any appropriate type of penetrating imaging unless otherwise specified, including trans-illumination, small-angle penetration imaging, etc. However, small angles may also result in direct reflection from the surface of the object (e.g., teeth), which may obscure internal structures.

The methods and apparatuses described here are particularly effective in combining a 3D surface model of the tooth or teeth with the imaged internal features such as lesions (caries, cracks, etc.) that may be detected by the use of penetration imaging by using an intraoral scanner that is adapted for separate but concurrent (or nearly-concurrent) detection of both the surface and internal features. Combining surface scanning and the penetration imaging may be performed by alternating or switching between these different modalities in a manner that allows the use of the same coordinate system for the two. Alternatively, both surface and penetrative scanning may be simultaneously viewed, for example, by selectively filtering the wavelengths imaged to separate the IR (near-IR) light from the visible light. The 3D surface data may therefore provide important reference and angle information for the internal structures, and may allow the interpretation and analysis of the penetrating images that may otherwise be difficult or impossible to interpret.

The penetrative scans described herein may be collected from, for example, an intraoral scanner such as the one illustrated in FIGS. 1A-1B for generating a three-dimensional (3D) model of a subject's intraoral region (e.g., tooth or teeth, gums, jaw, etc.) which may include internal features of the teeth and may also include a model of the surface, and methods of using such scanners. Although in many instances surface scanning (including color scans) may be helpful and useful, the penetrative (IR) scanning may, in some of the variations described herein, be sufficient.

In FIG. 1A the exemplary intraoral scanner 101 may be configured or adapted to generate 3D models having both surface and internal features, or just internal (penetrative) scans. As shown schematically in FIG. 1B, an exemplary intraoral scanner may include a handle or wand 103 that can be hand-held by an operator (e.g., dentist, dental hygienist, technician, etc.) and moved over a subject's tooth or teeth to scan both surface and internal structures. The wand may include one or more sensors 105 (e.g., cameras such as CMOS, CCDs, detectors, etc.) and one or more light sources 109, 110, 111. In FIG. 1B, three light sources are shown: a first light source 109 configured to emit light in a first spectral range for detection of surface features (e.g., visible light, monochromatic visible light, etc.; this light does not have to be visible light), a second color light source (e.g., white light between 400-700 nm, e.g., approximately 400-600 nm), and a third light source 111 configured to emit light in a second spectral range for detection of internal features within the tooth (e.g., by trans-illumination, small-angle penetration imaging, laser florescence, etc., which may generically be referred to as penetration imaging, e.g., in the near-IR). Although separate illumination sources are shown in FIG. 1B, in some variations a selectable light source may be used. The light source may be any appropriate light source, including LED, fiber optic, etc. The wand 103 may include one or more controls (buttons, switching, dials, touchscreens, etc.) to aid in control (e.g., turning the wand on/of, etc.); alternatively or additionally, one or more controls, not shown, may be present on other parts of the intraoral scanner, such as a foot petal, keyboard, console, touchscreen, etc.

In general, any appropriate light source may be used, in particular, light sources matched to the mode being detected. For example, any of these apparatuses may include a visible light source or other (including non-visible) light source for surface detection (e.g., at or around 680 nm, or other appropriate wavelengths). A color light source, typically a visible light source (e.g., "white light" source of light) for color imaging may also be included. In addition a penetrating light source for penetration imaging (e.g., infrared, such as specifically near infrared light source) may be included as well.

The intraoral scanner 101 may also include one or more processors, including linked processors or remote processors, for both controlling the wand 103 operation, including coordinating the scanning and in reviewing and processing the scanning and generation of the 3D model including surface and internal features. As shown in FIG. 1B the one or more processors 113 may include or may be coupled with a memory 115 for storing scanned data (surface data, internal feature data, etc.). Communications circuitry 117, including wireless or wired communications circuitry may also be included for communicating with components of the system (including the wand) or external components, including external processors. For example the system may be configured to send and receive scans or 3D models. One or more additional outputs 119 may also be included for outputting or presenting information, including display screens, printers, etc. As mentioned, inputs 121 (buttons, touchscreens, etc.) may be included and the apparatus may allow or request user input for controlling scanning and other operations.

Figure 2:
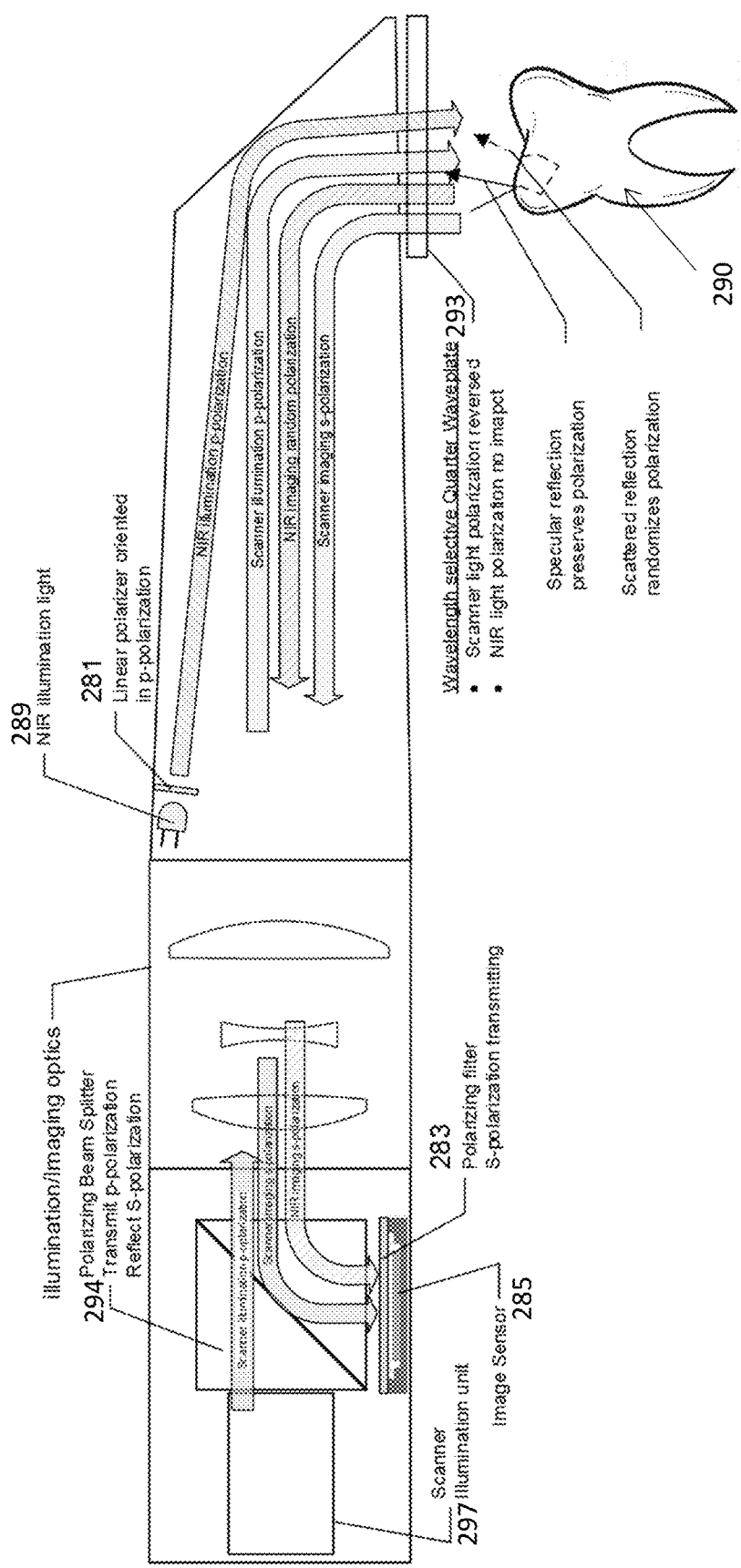
FIG. 2 shows a schematic of an intraoral scanner configured to do both surface scanning (e.g., visible light, non-penetrative) and penetrative scanning using a near infra-red (IR) wavelength. The scanner includes a polarizer and filters to block near-IR light reflected off the surface of the tooth while still collecting near-IR light reflected from internal structures.

FIG. 2 illustrates one example of a scanner that may be used. The scanner shown may be used as part of a system such as the system shown in FIGS. 1A-1B. For example, FIG. 2 shows a schematic of intraoral scanner configured to do both surface scanning (e.g., visible light, non-penetrative) and penetrative scanning using a near infra-red (NIR) wavelength (at 850 nm in this example). In FIG. 2, the scanner includes a near-IR illumination light 289 and a first polarizer 281 and a second polarizer 283 in front of the image sensor 285 to block near-IR light reflected off the surface of the tooth 290 (P-polarization light) while still collecting near-IR light scattered from internal tooth structures/regions (S-polarization light). The NIR light illuminates the tooth in P-polarization, and specular light reflected from the surface of the tooth, e.g., the enamel, is reflected with specular reflection hence its P-polarization state is conserved. Near-IR light penetrating the internal tooth features, such as the dentin, is scattered resulting in random polarization (S and P). The wavelength selective quarter waveplate 293 does not modify the polarization of the near-IR light (e.g., it leaves the polarization state of the near-IR light being delivered unchanged) but changes the polarization of the returning scan light from P to S such that only surface reflection are captured in the scan wavelength. The returning near-IR light, having a mixture of S and P polarizations, is first filtered through the polarization beam splitter (PBS) 294 and polarizing filter 283 such that only the S-polarization is transmitted to the image sensor. Thus only the near-IR S-polarization light, coming from the tooth internal structures, is captured by the image sensor while specular light, having the original p-polarization, is blocked. Other intraoral scanner configurations with or without polarization filters such as those shown in FIG. 2 may be used as part of the probe.

In FIG. 2, the surface scan may be performed by illuminating the surface (using the scanner illumination unit 297), illuminating in p-polarization, and the polarization may be reversed by the wavelength-selective quarter waveplate 293 (transmitting S-polarization light to the image sensor).

A variety of penetrative scanning techniques (penetration imaging) may be used or incorporated into the apparatuses described herein for performing scans that to detect internal structures using a penetrative wavelength or a spectral range of penetrative wavelengths, including, but not limited, to trans-illumination and small-angle penetration imaging, both of which detect the passage of penetrative wavelengths of light from or through the tissue (e.g., from or through a tooth or teeth). Thus, these apparatuses and techniques may be used to scan intraoral components such as a tooth or one or more teeth, gingiva, palate, etc. and used to generate a model of the scanned area. These models may be generated in real time or after scanning. These models may be referred to as 3D volumetric models of the teeth, but may include other regions of the jaw, including the palate, gingiva and teeth. Although the methods and apparatuses described herein typically relate to 3D volumetric models, the techniques and methods described herein may also be used in some instance with 3D surface models. The surface model information is typically part of the 3D volumetric model.

Figure 3:
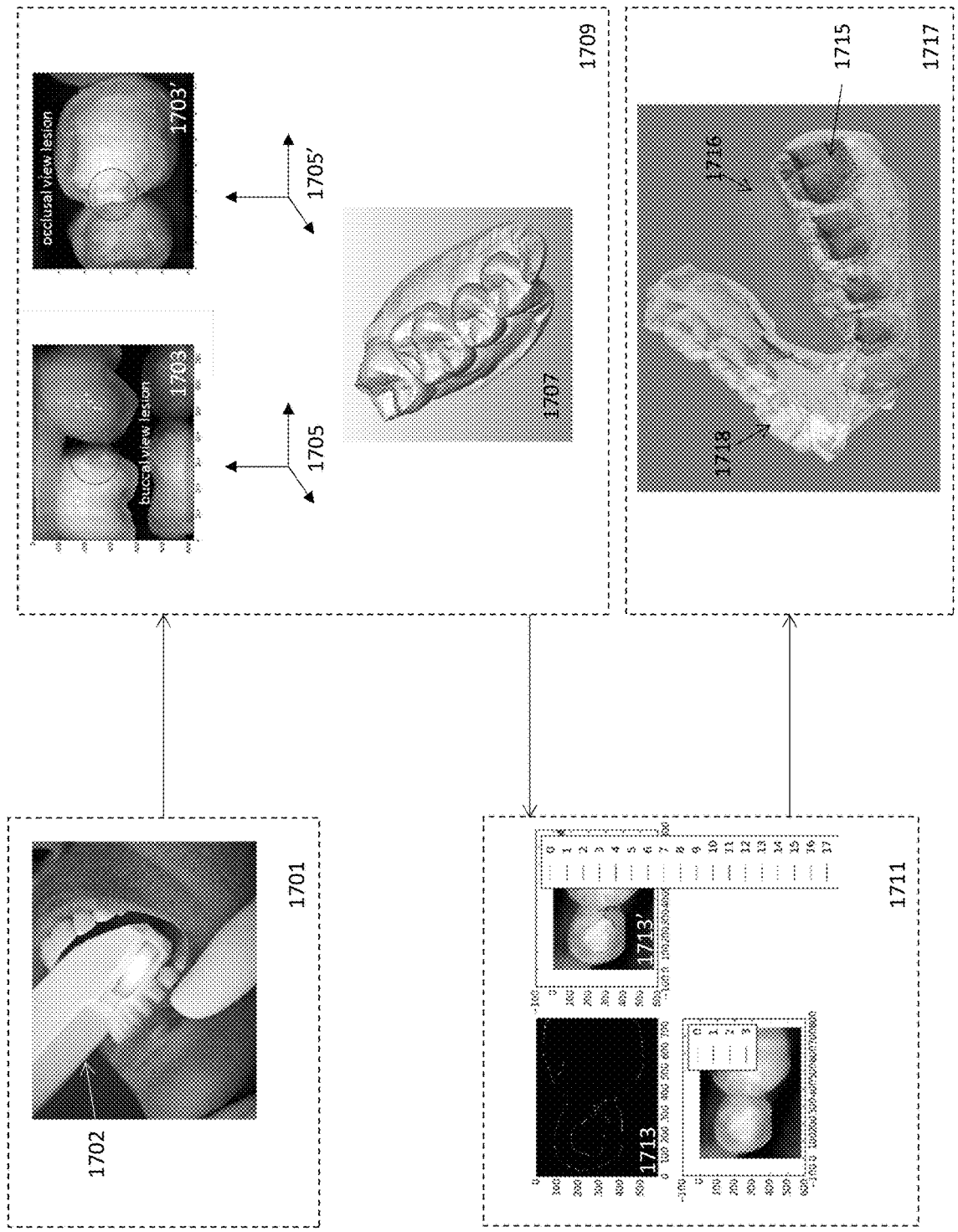
FIG. 3 is an example of a method of scanning teeth with an intraoral scanner to identify internal structures using a penetrative wavelength (e.g., IR and/or near-IR).

FIG. 3 illustrates an example of a data flow for scanning teeth with an intraoral scanner to build a 3D model including internal structures. In FIG. 3, the exemplary method shown may include three parts. First, the teeth may be scanned with an intraoral scanner 1701 (or any other scanner) configured to provide penetrative scans into the teeth using an optical (e.g., IR, near IR, etc.) wavelength or range of wavelengths. Any of these scanners may also concurrently scan to determine a surface features (e.g., via one or more non-penetrative wavelengths), color, etc., as described above. During scanning, a plurality of penetrative scans 1703, 1703' may be taken, and the position of the sensor (e.g., camera) 1705, 1705' (e.g., x,y,z position and/or pitch, roll, yaw angles) may be determined and/or recorded for each penetrative image. In some variations, the surface of the teeth may also and concurrently be imaged, and a 3D surface model of the teeth 1707 determined, as described above. In this example, the patient's teeth may be scanned, for example, with an intraoral 3D scanner 1702 that is capable of imaging the inner teeth structure using, for example, near infra-red imaging. The location and orientation of the camera may be determined, in part, from the 3D scanning data and/or the 3D teeth surface model 1707.

Thereafter, the penetrative images may be segmented 1711. In this example, segmentation may be done in one of two ways. On the inner teeth structure images, the images may be segmented using contour finding 1713, 1713'. Machine learning methods may be applied to further automate this process. Alternatively or additionally, near images (where their camera position is close) may be used to decide on close features, and also project features from the 3D model back to the images in order to locate correctly segments like enamel. The method may also include projecting pixels from the inner teeth images back to the teeth and calculating a density map of inner teeth reflection coefficient. Enclosing surfaces of different segments may be found or estimated by using iso-surfaces or thresholds of the density map and/or by machine learning methods. In addition, segmenting the images and projecting the segments back to a model (such as the 3D surface model, e.g., projecting back to the world), may be used to find a segment by the intersection of the segment projections and the teeth surface.

The results may be displayed 1717, transmitted and/or stored. For example, the results may be displayed by the scanning system during the intraoral scanning procedure. The results may be shown by images with enclosing contours for different segments, a 3D density map, etc. In the example shown in FIG. 3 a density map 1715, representing the dentin beneath the enamel on the outer surface, is shown. This image may be color coded to show different segments. In this example, internal segments (structures) are shown within the 3D surface model (which is shown transparent); not all teeth have been scanned with penetrative images, thus, only some are shown. Alternative views, sections, slices, projections or the like may be provided. In FIG. 3, the example image includes artifacts that are present outside of the teeth 1716; these may be removed or trimmed, based on the surface model 1718.

A segment may mark each pixel on the image. Internal structures, such as dentin, enamel, cracks, lesions, etc. may be automatically determined by segmentation, and may be identified manually or automatically (e.g., based on machine learning of the 3D structure, etc.). Segments may be displayed separately or together (e.g., in different colors, densities, etc.) with or without the surface model (e.g., the 3D surface model).

Thus, in FIG. 3, the patient is initially scanned with a 3D scanner capable of both surface scanning and penetrative scanning (e.g., near IR imaging), and the orientation and/or position of the camera is known (based on the position and/or orientation of the wand and/or the surface scans). This position and orientation may be relative to the tooth surface. The method and apparatus may therefore have an estimate of the camera position (where it is located, e.g., x,y,z position of the camera, and its rotational position).

In general, penetrative images (e.g., near IR or IR images) may be segmented automatically.

User Interface and Display of Volumetric Information

The collection and analysis of volumetric data from the intraoral cavity may identify features and information from teeth that were previously difficult or impossible to identify from non-volumetric scanning. However, it may be difficult or non-intuitive for a dental practitioner (and/or patient) to analyze three-dimensional volumetric information. Described herein are methods and apparatuses for viewing and interpreting 3D, volumetric data of a patient's oral cavity.

Figure 9B:
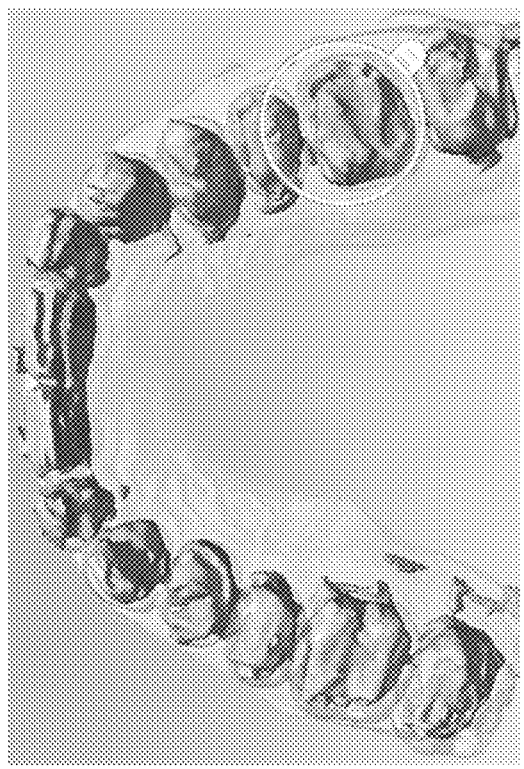
FIGS. 9A-9G illustrate one method of displaying volumetric information from a patient's teeth.
Figure 9A:
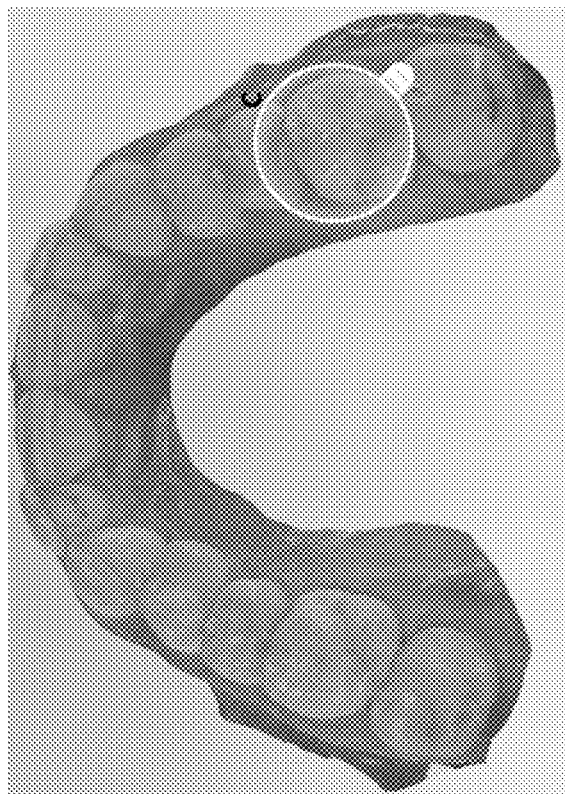
Figures 9F, 9G:
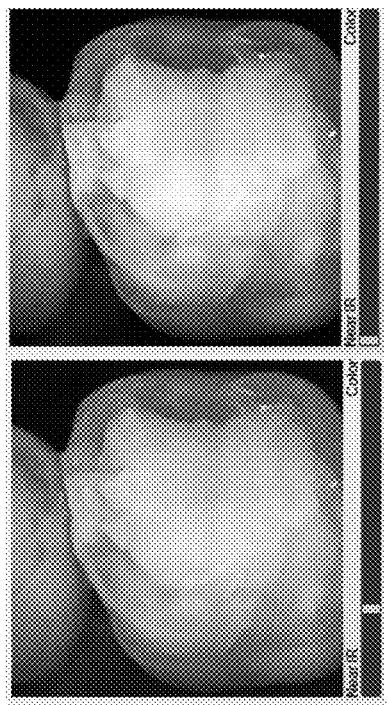

For example, FIGS. 9A-9G illustrate one example of a method for displaying 3D volumetric data. FIG. 9A shows a surface model (which may be a surface model portion of a volumetric model) from a top view of an upper arch, in which external features are visible (e.g., surface features). This view is similar to the surface scan view which may be in color (e.g., taken by visible light). Internal structures, which are present within the model beneath the external surface of the scan, are not readily visible in FIG. 9A. FIG. 9B, the internal structures are shown based on their relative transparency to near-IR light. In FIG. 9B, the enamel is more transparent (and is shown as more transparent) than the dentin, which is shown as less transparent. FIGS. 9B-9F illustrate a transition between the surface view of FIG. 9A and the penetrative, internal 3D view of FIG. 9B for a sub region (circled region "C") shown. For example, a user display may be provided in which the relative surface vs. internal views may be altered to provide a sense of internal structures within the dental arch relative to surface structures. For example, an animated view cycling through image such as FIGS. 9C-9G may be provided. Alternatively, the user may slide a slider 903 toggling between the surface and internal views. The transition between these two views (which may be made from any angle, may help the user and/or patient to see beneath the surface of the teeth, to visually assess the rich internal data. The 3D volumetric model may be manipulated to show any view, including cross-sectional views, showing internal structures and/or surface features. In FIG. 9A-9G the top view is shown. FIGS. 9C-9G illustrate progressively more transparent views or a region ("C") of the 3D volumetric model of FIG. 9A in which progressively large percentages (from 0% to 100%) of the internal view of FIG. 9B is shown for region C, while progressively less of the surface view (from 100% to 0%) is shown.

Figure 9E:
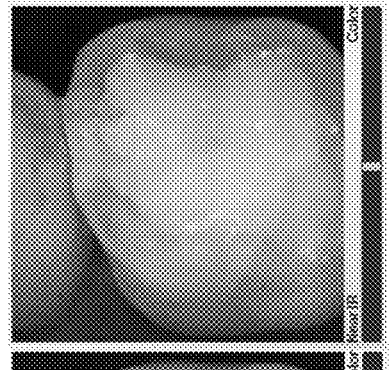
Figures 9C, 9D:
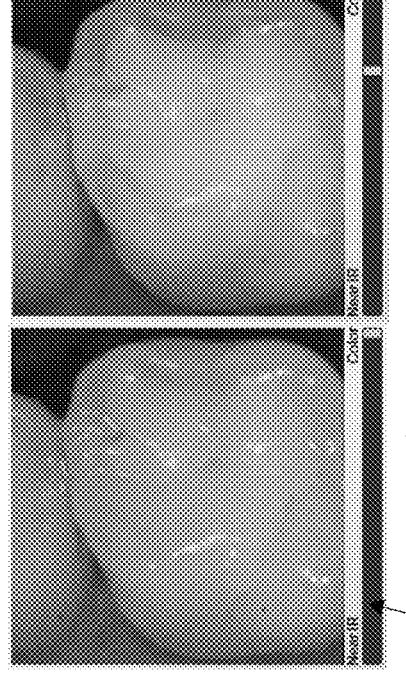

FIGS. 11A-11C illustrate another example, showing a hybrid image that (like FIG. 9E combines and mixes both surface image scanning (e.g., a visible light scan, as shown in FIG. 11A) with a volumetric model taken using a penetrative (e.g., near-IR) wavelength, as shown in FIG. 11B. Features that are present in the tooth enamel and dentin are visible in the volumetric reconstruction (image shown in FIG. 11B) that are not apparent in the image (which may also be a reconstruction) of just the surface shown in FIG. 11A. For example, in FIG. 11B, a carries region 1103 is apparent, which is not visible in FIG. 11A. Similarly a bubbled region of the enamel 1105 is visible in FIG. 11B but is not visible in FIG. 11A. FIG. 11C shows a hybrid image of the 3D volumetric model and surface model (surface image), in which both of these structures, the carries and the bubbled region, are visible.

In general, described herein are methods and apparatuses for simplifying and displaying volumetric data from a patient's oral cavity (e.g., teeth, gingiva, palate, etc.) in a manner that may be easily understood by a user (e.g., a dental practitioner) and/or a patient. Also described herein are methods of displaying volumetric data taken from a patient's oral cavity in a manner that may be familiar for a user and/or patient to understand. In a first example, the data may be presented as one or a series of x-ray type images, similar from what would be produced by dental x-rays. FIG. 4 illustrates one method of generating x-ray (or pseudo x-ray) images from a volumetric data set taken as described above, e.g., using penetrative light (e.g., near-IR) wavelength(s).

As shown in FIG. 4, a method of displaying 3D volumetric images of a patient's oral cavity may include receiving the 3D volumetric data 401, e.g., from a scan as described above, either directly or from a stored digital scan, etc. In some variations, individual teeth or groups of teeth may be identified from the volumetric data 403. The teeth may be identified automatically (e.g., by a segmenting the volume, by machine learning, etc.) or manually. Alternatively, the entire volume may be used. Pseudo-x-ray images may then be generated from the volume or sub-sets of the volume corresponding to individual teeth 405. For example, an image of the volume may be taken from the 'front' of the tooth or teeth, in which the transparency of the enamel (and/or enamel-like restorations), dentin and other features are kept from the volumetric data. This volumetric data may be based on the absorption coefficients of the material within the oral cavity for the penetrating wavelength of light used. Thus, a projection through the volumetric data may be generated for a fixed direction from the volumetric data to get an image similar to an X-ray, but, in some variations, inverted and showing the density of the dentin (highly absorbing) as "darker" than the density of the enamel (less absorbing and therefore more transparent); caries may also show up as more absorbing (darker) regions. The image may therefore be inverted to resemble an x-ray image in which more dense regions are lighter (e.g., brighter). These pseudo x-ray images may be generated from the same positions as standard dental x-rays and presented to the user. For example, a panel of pseudo x-ray images may be generated from the volumetric model for each of the patient's teeth. Although the penetration of the wavelength of the light (e.g., near IR light) may not be as deep as with traditional x-rays, images generated in this manner may provide a comparable proxy for an x-ray, particularly in the crown and mid-tooth regions above the gingiva.

Other simplified or modified displays may be provided to the user, or customized for display by the user to the patient. For example, in some variations images of the teeth may be generated from the volumetric data in which the image is simplified by pseudo coloring the volumetric data to highlight certain regions. For example, regions that have been previously marked or flagged (as will be described in greater detail, below) may be colored in red, while the enamel may be shown as a more natural white or slightly off-white color. In some variations, enamel-like materials (e.g., from fillings, etc.) may be represented separately and/or marked by a color, pattern, etc.

In some variations, the methods and/or apparatuses may display the teeth in sections through the dental arch. Similarly the individual teeth or groups of teeth may be shown separately and/or labeled (e.g., by standard naming/numbering convention). This may be shown in addition or instead of other displays. In some variations, the teeth and/or internal structures may be pseudo-colored or projecting on to a color image may be used.

Figure 5A:
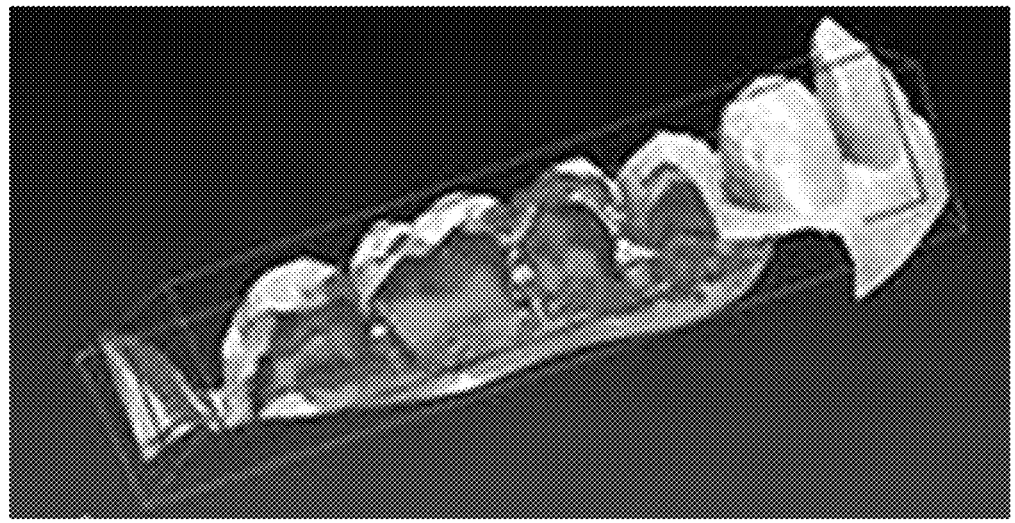
FIGS. 5A and 5B illustrate virtual sections from a volumetric model of the teeth. These virtual sections may be annotated, colored/pseudo-colored, or textured, to show internal features or properties of the teeth.
Figure 5B:
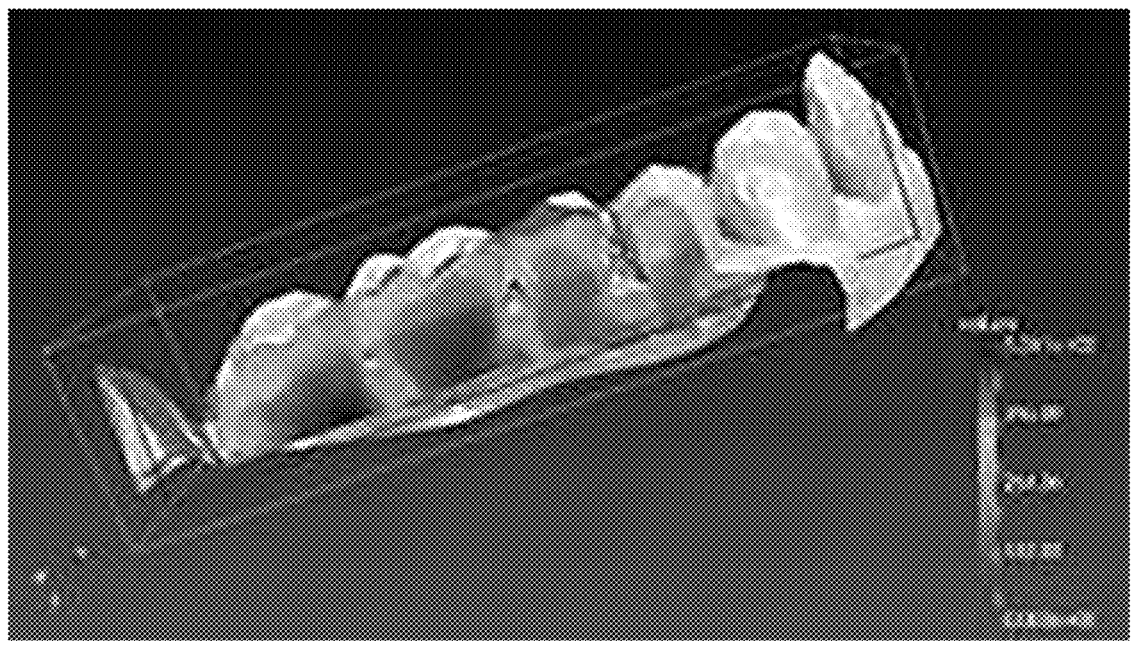

For example, FIGS. 5A and 5B illustrate virtual sections taken through a volumetric model of a patient's teeth generated from an intraoral scan that included near-IR information, and described above. In FIG. 5A, the cross-sectional view may be generated automatically or manually, e.g., by the user, to display regions of interest within teeth, including enamel. The cross-section may show both density sectioning and/or surface sectioning. These images may be pseudo-colored to show different regions, including outer surfaces, enamel, dentin, etc. Internal structures, e.g., within the enamel and/or dentin, may reflect the effect of the near-IR light within the teeth, such as the absorption and/or reflection of light at one or more near-IR/visible wavelengths within the teeth. In FIG. 5B, the section is pseudo-colored with a heat map to show internal features, and a key may be provided, as shown. In any of these variations, 2D projections of the teeth may be generated from the volumetric information, showing one or more features on the tooth and/or teeth. As will be described in greater detail below, additional features, including lesions (e.g., caries/cavities, cracks, wearing, plaque build-up, etc.) may be displayed as well, and may be indicated by color, texture, etc. While illustrated as sections of the 3D volumetric model, other embodiments may display the 2D section by itself to provide a cross-sectional view of the tooth/teeth similar to a view provided by 2D x-ray images.

Any of the methods and apparatuses for performing them described herein may include displaying one or more (or a continuous) sections through a 3D model of the patient's dental arch, and preferably a 3D volumetric model. For example, a method of displaying images from a three-dimensional (3D) volumetric model of a patient's dental arch may include: collecting the 3D volumetric model of the patient's dental arch, wherein the 3D volumetric model includes near-infrared (near-IR) transparency values for internal structures within the dental arch; generating a two-dimensional (2D) view into the 3D volumetric model including the patient's dental arch including the near-IR transparency of the internal structures; and displaying the 2D view. In any of these methods, the method may optionally (but not necessarily) include scanning the patient's dental arch with an intraoral scanner.

Generating the 2D view may comprises sectioning the 3D volumetric model in a plane through the 3D volumetric model. The user may select the plane's location and/or orientation, and my do this in a continuous manner. For example, any of these methods may include selecting, by a user, a section though the 3D volumetric model to display, wherein selecting comprises continuously selecting sections through the 3D volumetric model as the user scans through the 3D model and continuously displaying the 2D views corresponding to each section. Generating the 2D view may comprises selecting, by a user, an orientation of the 2D view.

In any of these methods, the surface may be included. For example, as described and illustrated above, a method of displaying images from a three-dimensional (3D) volumetric model of a patient's dental arch may include: collecting the 3D volumetric model of the patient's dental arch, wherein the 3D volumetric model includes surface values and near-infrared (near-IR) transparency values for internal structures within the dental arch; generating a two-dimensional (2D) view into the 3D volumetric model including the patient's dental arch including both surface values and the near-IR transparency of the internal structures; and displaying the 2D view. The surface values may comprise surface color values. The surface relative to the internal (volumetric) structures may be weighted. For example, generating the two-dimensional (2D) view through the 3D volumetric may also include including in the 2D view a weighted portion of the surface values and a weighted portion of the near-IR transparency of the internal structures. The weighted portion of the surface values may include a percentage of the full value of the surface values, and the weighted portion of the near-IR transparency of the internal structures comprises a percentage of the full value of the near-IR transparency of the internal structures, wherein the percentage of the full value of the surface values and the percentage of the full value of the near-IR transparency of the internal structures adds up to 100%. For example, the user may adjust the weighted portion of one or more of the surface values and the near-IR transparency of the internal structures.

For example, a method of displaying images from a three-dimensional (3D) volumetric model of a patient's dental arch may include: collecting the 3D volumetric model of the patient's dental arch, wherein the 3D volumetric model includes surface color values and near-infrared (near-IR) transparency values for internal structures within the dental arch; selecting, by a user, an orientation of a view of the 3D volumetric model to display; generating a two-dimensional (2D) view into the 3D volumetric using the selected orientation, including the patient's dental arch including a weighted portion of the surface color values and a weighted portion of the near-IR transparency of the internal structures; and displaying the 2D view.

In addition to displaying qualitative images of the teeth, the methods and apparatuses described herein may quantify, and may provide quantitative information about internal and/or external features. For example, volumetric measurements of one or more lesions may be provided (selectably or automatically) including dimensions (peak or mean length, depth, width, etc.), volume, etc. This may be performed by manually or automatically segmenting the volumetric model to define the regions of interest, including either or both tooth features (enamel, dentin, etc.) and/or irregularities (e.g., caries, cracks, etc.). Any appropriate segmentation technique may be used, such as but not limited to: mesh segmentation (mesh decomposition), polyhedral segmentation, skeletonization, etc. Once the volume has been segmented, these regions may be separately or collectively displayed and/or measured. As will be described below, they may also be marked/flagged and used for further analysis, display and modification of the scanning methods and systems.

In some variations of the user interfaces described herein, a summary report may be generated or created and displayed for the user and/or patient from the volumetric data. For example, summary data may be projected onto a model of the patient's teeth. The model may also be simplified, so that the enamel is opaque, but marked or selected internal features (including automatically selected internal features) are shown in red or some other contrasting color (and/or flashing, blinking, etc.) within the tooth. For example, caries may be shown in this manner. The summary report may be automatically entered into a patient chart.

Any of the images, including the volumetric images, may be animated. For example, virtual sections through the patient's teeth, showing a scanning or traveling cross-section through the patient's dentition may be shown, in some cases with a 3D model showing one or more cutting axes through the volume. The user interface may allow the user to section in one or more planes, showing both external and internal features based on the volumetric scan.

In general, the apparatuses described herein may generate separate view for the user (e.g., physician, dentist, orthodontist, etc.) than the patient. The user may be provided with a 'clinical view' that may include information not present on a separate 'patient view.' The clinical view may be more technical, and may in some cases be closer to the raw images from the volumetric data. The user may select which layers of information to include in the patient view, which may then be presented to the user during or after the scanning or review of the dental scanning. Patient educational materials may be appended to the patient view.

For example, in some variations, the user display of volumetric data may include an overlay of the volumetric data in which pseudo coloring of the 3D components within the volumetric data is shown. As will be discussed in more detail below, in any of these displays/images marked or highlight regions may be shown to call attention to potential problem regions (e.g., caries, thin enamel, cracks, etc.). Two-dimensional (2D) color data and 3D near-IR data (e.g., surface and volumetric regions) may be shown, including transitions between the two.

In general, the volumetric information may be annotated (e.g., marked, labeled, etc.) either automatically, manually, or semi-automatically, and this annotation may be displayed. Furthermore, annotations may be used both to annotate future additional scans, and to modify how future scans of the same patient are taken and displayed. An annotation may be, for example, a marker or flag on a region of interest. Regions of interest may correspond to specific regions in which one or more features (cracks, caries, thinning of enamel, buildup of plaque or calculus, etc.) have been observed. Alternatively or additionally, regions of interest may be regions in which there is a change over time, e.g., from one scan to another scan.

As mentioned above any of these methods may include placing one or more markers on the volumetric model of the patient's teeth. Markers (e.g., flags, pins, etc.) may be manually placed by the user, or may be automatically placed by the apparatus, or may be semi-automatically placed (e.g., suggested by the system, configured by the user, etc.). This is described in greater detail below.

Markers may be used to focus attention and/or processing by the system on one or more specific regions of the volumetric model for display, and/or for later follow-up (e.g., in future scans). Markers may modify the manner in which the later scans are taken, e.g., taking future scans of marked regions with greater detail (e.g., higher resolution, different wavelengths, greater scanning frequency or reputations, etc.). Marked regions may be displayed over time to show changes in the marked regions.

For example, a user can mark a digital representation of the patient's teeth (or the patient's actual teeth) with a marker (e.g., a pin, flag, etc.) which can be annotated (e.g., can have notes associated with it). This marker may then be used to track over time between different scans. Later scans can be marked in the corresponding location, the later scan can be modified based on the marked regions. These marked regions may be scanned in greater detail, and analytics may be automatically performed and/or displayed, measuring and/or indicating a change compared to one or more earlier scans. Thus any of the systems described herein may track one or more marked regions from previous scans and give feedback during and/or after a new scan, providing additional detail. This can be done for both surface and/or volumetric information, particularly on the properties of the enamel, and/or by comparison to the enamel, the outer surface of the teeth/tooth, and/or the dentin.

For example, one or more annotation markers from an earlier scan may modify a subsequent scanning of the same patient. Before scanning, the user may enter an identifier of the patient being scanned (alternatively the system may automatically identify the patient based on a database of earlier scans). The system may automatically annotate the new scan based on the prior scan annotations.

In some variations the later scans may be automatically annotated by the system by identifying differences between the prior scan(s) and the current scan. For example, regions showing a change above a threshold compared to the earlier scan may be flagged and presented to the user. The annotation may be done without user oversight (fully automatic) or may be done with some user oversight, for example, by flagging it and indicating to the user why it was flagged, then allowing the user to keep, modify or reject the marking. Reasons for automatically marking the teeth may include a change in the enamel thickness, a change in the surface smoothness, a change in the relative ratio of enamel vs. dentin in a tooth, a change in the position of the tooth (e.g., occlusion), etc. It may also include a change in structures external to the natural tooth, such as increase or decrease in plaque or calculus buildup, or changes to the gingival structures surrounding the tooth, Thus, if the system detects one or more of these conditions, it may automatically flag the relevant region in the volumetric model.

Later scans may be dynamically modified by the flags from earlier scans or by a detection of a change in a region (even unmarked regions) compared to earlier scans. For example, the scanning parameters may be modified to scan at higher resolution (e.g., changing the scan dwell time, requiring the user to scan this region multiple times, etc.), changing the wavelength used for the scanning, etc.

Figure 6:
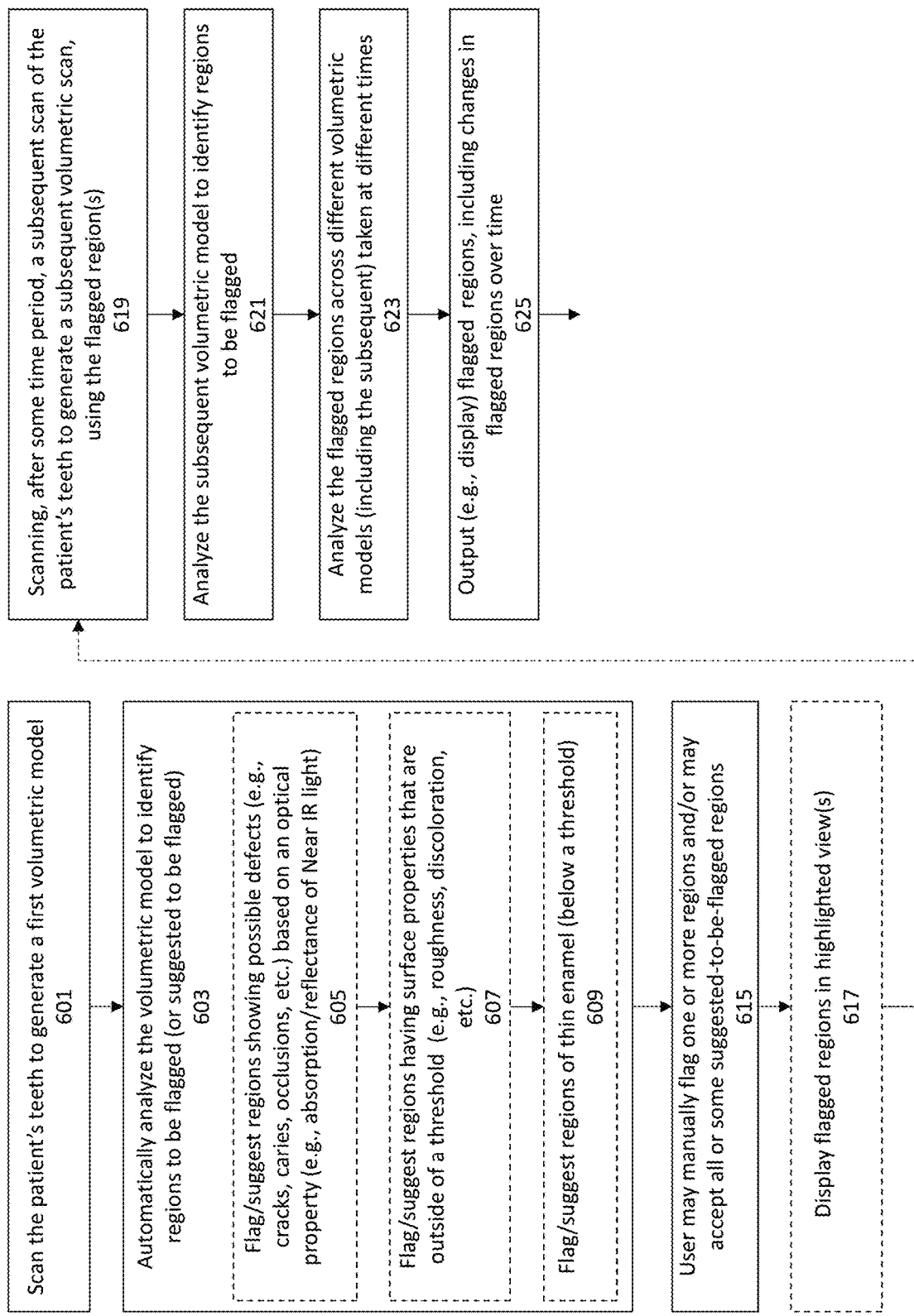
FIG. 6 illustrates one method of marking (e.g., flagging) a volumetric model of a patient's teeth, and/or using the marked regions.

For example, FIG. 6 illustrates a method of automatically selecting a region for marking and/or using the selected regions. A first volumetric model of the patient's teeth is generated from a scan of the patient's teeth 601. The volumetric model may be generated using any appropriate method, including those described above and discussed in U.S. patent application Ser. No. 15/662,234, filed Jul. 27, 2017, titled "INTRAORAL SCANNER WITH DENTAL DIAGNOSTICS CAPABILITIES", incorporated by reference in its entirety. The first volumetric model may be stored (digitally stored) as part of the patient's dental record. The first volumetric model may concurrently or subsequently (immediately or some time thereafter) be analyzed (e.g., by an apparatus, including an apparatus having a processor that is configured to operate as described herein) to identify any regions that should be flagged 603. This analysis may therefore be performed automatically, and may examine one or more properties of the patient's teeth from the scan. Automatic (or semi-automatic, etc., automatic but with manual assistance to verify/confirm) may be performed by a microprocessor, including systems that have been trained (e.g., by machine learning) to identify regions of irregularities on the outside and/or internal volume of the teeth. For example, the apparatus may examine the digital model to identify possible defects in the patient's teeth such as (but not limited to): cracks, caries, voids, changes in bite relationship, malocclusions, etc. This may include identifying regions in which there is an optical (e.g., near-IR) contrast near the surface of the tooth indicating a possible crack, caries, occlusion, etc. 605. Regions that are less transparent (e.g., more absorptive) in the near-IR wavelengths than the rest of the enamel, that are closer to the surface (generally or within specific near-IR wavelengths), may correspond to defects. Alternatively or additionally, surface properties of the teeth may be examined and flagged if they are outside of a threshold 607. For example, regions of the surface of the teeth in which the tooth surface is rough (e.g., has a smoothness that is below a set threshold, where smoothness may be determined from the outer surface of the enamel) may be flagged. Other surface properties may also be analyzed and used to determine if the region should be marked or presented to the user to confirm marking, including discoloration (based on a color or white-light/surface scan), gingival position (relative to the outer surface of the tooth), etc. The distribution and size of the patient's enamel may also be examined 609. The enamel thickness may be determined from the optical properties (e.g., comparing absorption/reflectance properties). Regions of putative enamel that are below a threshold thickness, or having a ratio of thickness to tooth dimension (e.g., diameter, width, etc.) below a threshold may be marked or presented to the user to confirm marking.

In some variations, during and/or after automatically analyzing the volumetric model, the use may also manually flag one or more regions of the volumetric model of the patient's teeth 615. If the automatic analysis of the volumetric model automatically flags the identified volumetric model the user's manually added regions may be added. In some variations, the user may be prompted to flag the regions identified and suggested by the automatic analysis. These regions may be marked and an indication of the reason(s) for their being identified may be provided (e.g., irregular enamel, potential crack, potential caries, potential thinning of the enamel, etc.). In general, the inner boundary (the boundary within the volume of the tooth, for example) may be defined in any of the methods and apparatuses described herein. For example, in variations in which a region of the enamel is thinning, the methods and apparatuses described herein may be used to the entire layer (e.g., layer of enamel, region of the inner structure of the tooth) may be identified and used for qualitative and/or quantitative information.

In some variations the method flagged regions may then be displayed on a digital model of the patient's teeth 617. The display may emphasize the flagged regions, e.g., by providing a color, animation (e.g., flashing), icon (e.g., arrow, flag, etc.), or the like, including combinations of these. The display may also show enlarged views of any of these. The user may modify the display, e.g., rotating, sectioning, enlarging, etc., the flagged region. Alternatively or additionally, the flagged regions may be enlarged on the display by default. An index or key of the flagged regions may be provided, and may be displayed and/or stored with the digital volumetric model of the patient's teeth.

In some variations, as shown to the right of FIG. 6, the method may include using the flagged regions to modify the future scans, as mentioned above. For example, the method may include scanning ("rescanning") using the flagged regions, after some interim time period of between a first time (e.g., about one day, one week, one month, 2 months, 3 months, 4 months, 5 months, 6 months, 7 months, 8 months, 9 months, 10 months, 11 months, 1 year, 1.2 years, 1.5 years, 2 years, etc.) and a second time (e.g., about one month, 2 months, 3 months, 4 months, 5 months, 6 months, 7 months, 8 months, 9 months, 10 months, 11 months, 1 year, 1.5 years, 2 years, 3 years, 4 years, 5 years, 6 years, 7 years, 8 years, 9 years, 10 years, 11 years, 12 years, 13 years, 14 years, 15 years or more, etc.), or longer than the second time period. The flagged regions may be used to modify the scan by increasing the resolution of the scanned regions during the scan, e.g., by increasing the scan rate, increasing the dwell time in this region, scanning the region in additional wavelengths, scanning this region multiple times, etc. The scanning apparatus may inform the user to adjust the scanning (e.g., moving the wand of an intraoral scanner more slowly in these regions, moving the scanner back over these regions multiple times, etc.) and/or it may automatically adjust the scanning parameters during operation. The scanning apparatus may therefore receive the key or index of flagged regions and/or a marked (flagged) version of the patient's earlier intraoral scan(s). Prior to scanning the scanning apparatus, the user may indicate the identity of the patient being scanned, and this may be used to look up the earlier scan(s). Alternatively or additionally, the apparatus may identify the patient based on the current scan to identify (or confirm the identity) of the patient, to verify or recall the earlier annotated (flagged) scan. Alternatively, the second or subsequent scans may be taken without using the earlier flagged regions.

Following the subsequent (e.g., second, later or follow-up scan or scans), the method or apparatus configured to perform the method may then compare the flagged regions from the subsequent scan with the corresponding regions from the earlier scan(s) 621. In addition, the volumetric model from the subsequent scan may automatically analyzed to identify any regions of the new (subsequent) scan that can/should be marked/flagged (e.g., repeating the earlier automatic or semi-automatic analysis steps 603-615) 621. Newly identified regions from the subsequent scan may be compared to the previously un-flagged corresponding regions in the earlier volumetric model(s).

The flagged regions may be analyzed over time 623. Specific sub-regions from the volumetric model including the flagged regions may be generated for display and analysis. The results may be output 625. For example, these regions may be displayed to the user along with descriptive, analytic information about the scanned region. These regions may also be marked to shows changes over time. The data may be displayed in an animation, for example, showing changes over time. In some variations, the images may be displayed as a time-lapse image (video, loop, etc.), showing changes. Time-lapse images may show the change in the internal and/or external structure over time. Sections (pseudo-sections generated from the volumetric model(s)) may be used to show changes. Color, texture, patterns, and any other highlighting visualization technique may be used. Alternatively or additionally to the display of the flagged regions, these regions (and any accompanying analysis) may be output in other appropriate ways, including digitally outputting (e.g., the patient's dental record), printing a description of the flagged region(s), etc.

Any of the methods of tracking a region of a patient's dental arch described herein may include tracking over time and/or across different imaging modalities (e.g., records) as described in greater detail below. Further, any of these methods may be automated and/or may include automated agents, for example, for identifying one or more regions of interest (e.g., features, defects, including actionable dental features), including for scoring them and/or automating identification, scoring and/or display of such regions. Any of these methods may also include any of the display methods or agents (e.g., for displaying sections, displaying internal structures, for displaying virtual x-rays, for displaying across imaging modalities, etc.).

For example, a method of tracking a region of a patient's dental arch over time may include: collecting a first three-dimensional (3D) volumetric model of the patient's dental arch, wherein the 3D volumetric model includes surface values and near-infrared (near-IR) transparency values for internal structures within the dental arch; identifying a region of the 3D volumetric model; flagging the identified region; collecting a second 3D volumetric model of the patient's dental arch; and displaying one or more images marking, on the one or more images, a difference between the first 3D volumetric model and the second 3D volumetric model at the flagged region.

Any of these methods may also include tracking and/or comparing across different records (e.g., different imaging modalities), so that identifying comprises identifying a region of the patient's dental arch from a first record of a plurality of records, wherein each record comprises a plurality of images of a patient's dental arch each taken using an imaging modality, further wherein each record of the plurality of records is taken at a different imaging modality, further wherein flagging comprises flagging the identified region in a corresponding region of the 3D volumetric model of the patient's dental arch. The method and apparatuses for performing them may also include correlating the flagged region with each of records of the plurality of records by correlating the 3D volumetric model of the patient's dental arch with each of the records of the plurality of records. In some variations the correlation may be used to weight or grade the identified region to determine if it corresponds to a region of interest (e.g., a feature, a defect, including actionable dental features, etc.). For example, the region of the patient's dental arch may comprises a dental feature comprises one or more of: cracks, gum recess, tartar, enamel thickness, pits, caries, pits, fissures, evidence of grinding, and interproximal voids. Identifying the region may comprise comparing a near-IR transparency value of a region within the 3D model to a threshold value.

Where surface values are used, the surface values may comprise surface color values. These methods may be used with stored data and/or with data collected in real time (e.g., thus the method may optionally but not necessarily collect a three-dimensional (3D) volumetric model by scanning the patient's dental arch to generate the 3D volumetric model.

Identifying the region may comprise comprises automatically identifying using a processor. For example, automatically identifying may comprise identifying a surface color value outside of a threshold range. Automatically identifying may comprise segmenting the 3D volumetric model to identify enamel regions and identifying regions having enamel thicknesses below a threshold value.

Flagging the identified region may comprise automatically flagging the identified regions or manually confirming the identified region for flagging.

In any of these method in which regions are flagged, the method may include re-scanning the patient's dental arch wherein the flagged region is scanned at a higher resolution than un-flagged regions.

A method of tracking a region of a patient's dental arch over time may include: collecting a first three-dimensional (3D) volumetric model of the patient's dental arch taken at a first time, wherein the 3D volumetric model includes surface color values and near-infrared (near-IR) transparency values for internal structures within the dental arch; identifying, using an automatic process, a region within the 3D volumetric model to be flagged from a first record of a plurality of records, wherein each record comprises a plurality of images of a patient's dental arch each taken using an imaging modality, further wherein each record of the plurality of records is taken at a different imaging modality; flagging the identified regions; correlating the flagged region with each of the records of the plurality of records by correlating the 3D volumetric model of the patient's dental arch with each of the records of the plurality of records; collecting a second 3D volumetric model of the patient's dental arch taken at a separate time; and displaying a difference between the first 3D volumetric model and the second 3D volumetric model at the flagged region.

Similarly, as summarized and described above, a method of tracking a dental feature across different imaging modalities, the method comprising: collecting a first three-dimensional (3D) volumetric model of the patient's dental arch, wherein the 3D volumetric model of the patient's dental arch includes surface values and internal structures within the dental arch; identifying a region of the patient's dental arch from a first record of a plurality of records, wherein each record comprises a plurality of images of a patient's dental arch each taken using an imaging modality, further wherein each record of the plurality of records is taken at a different imaging modality; flagging the identified region in a corresponding region of the 3D volumetric model of the patient's dental arch; correlating the flagged region with each of the records of the plurality of records by correlating the 3D volumetric model of the patient's dental arch with each of the records of the plurality of records; and saving, displaying and/or transmitting images including the region of the patient's dental arch. Any of these methods may include tracking over time as well, e.g., by comparing the same region(s) to 3D volumetric models at different times.

Figure 10A:
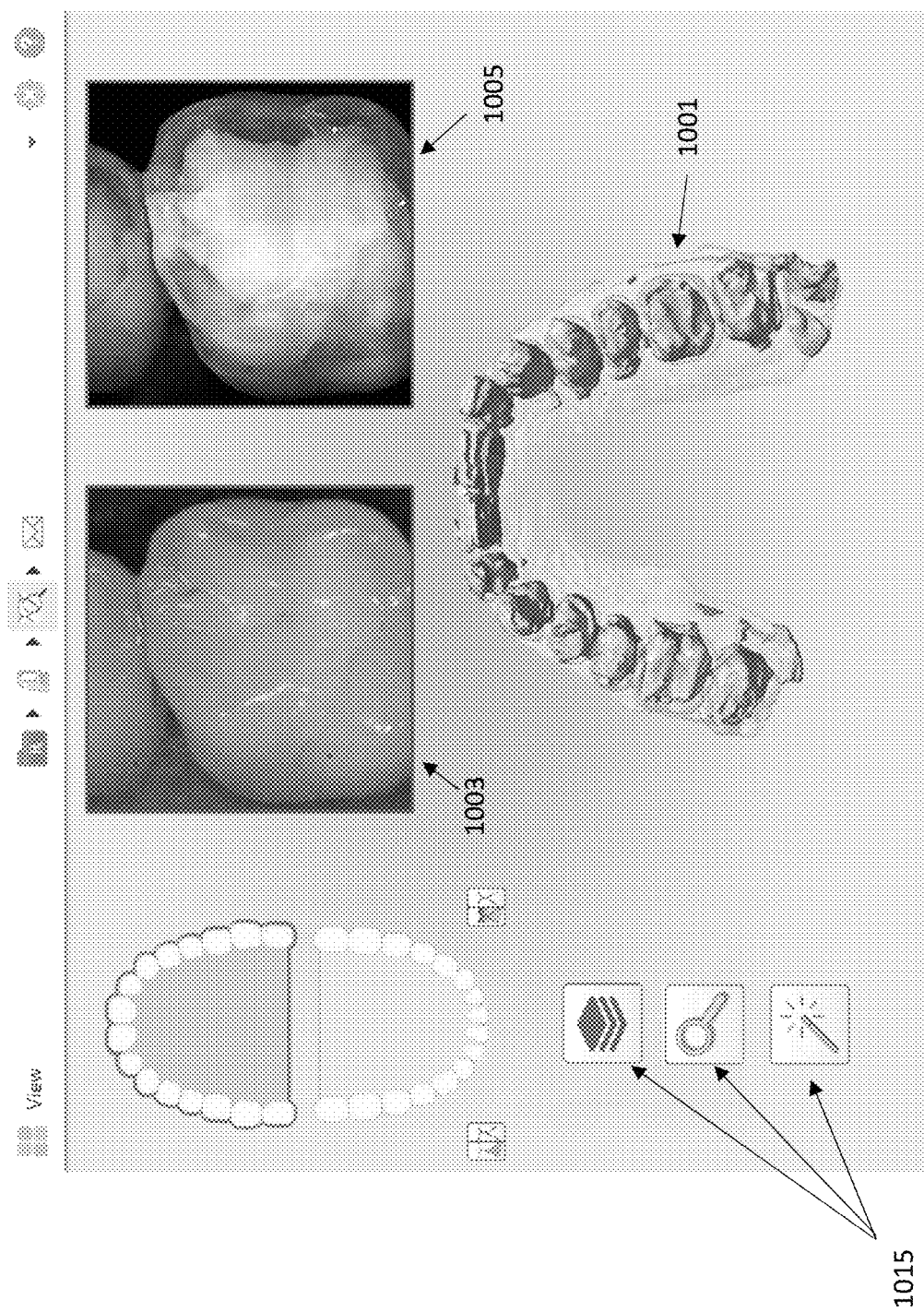
FIG. 10A illustrates an example of a user interface for analysis and/or display of a 3D volumetric model of a patient's teeth, showing a top view of the upper arch, tools that may be used to manipulate the view(s), and two enlarged views showing the outer surface of an enlarged region of the tooth (on the left) and the same view showing internal features of the tooth (showing dentin and enamel within the tooth).
Figure 10B:
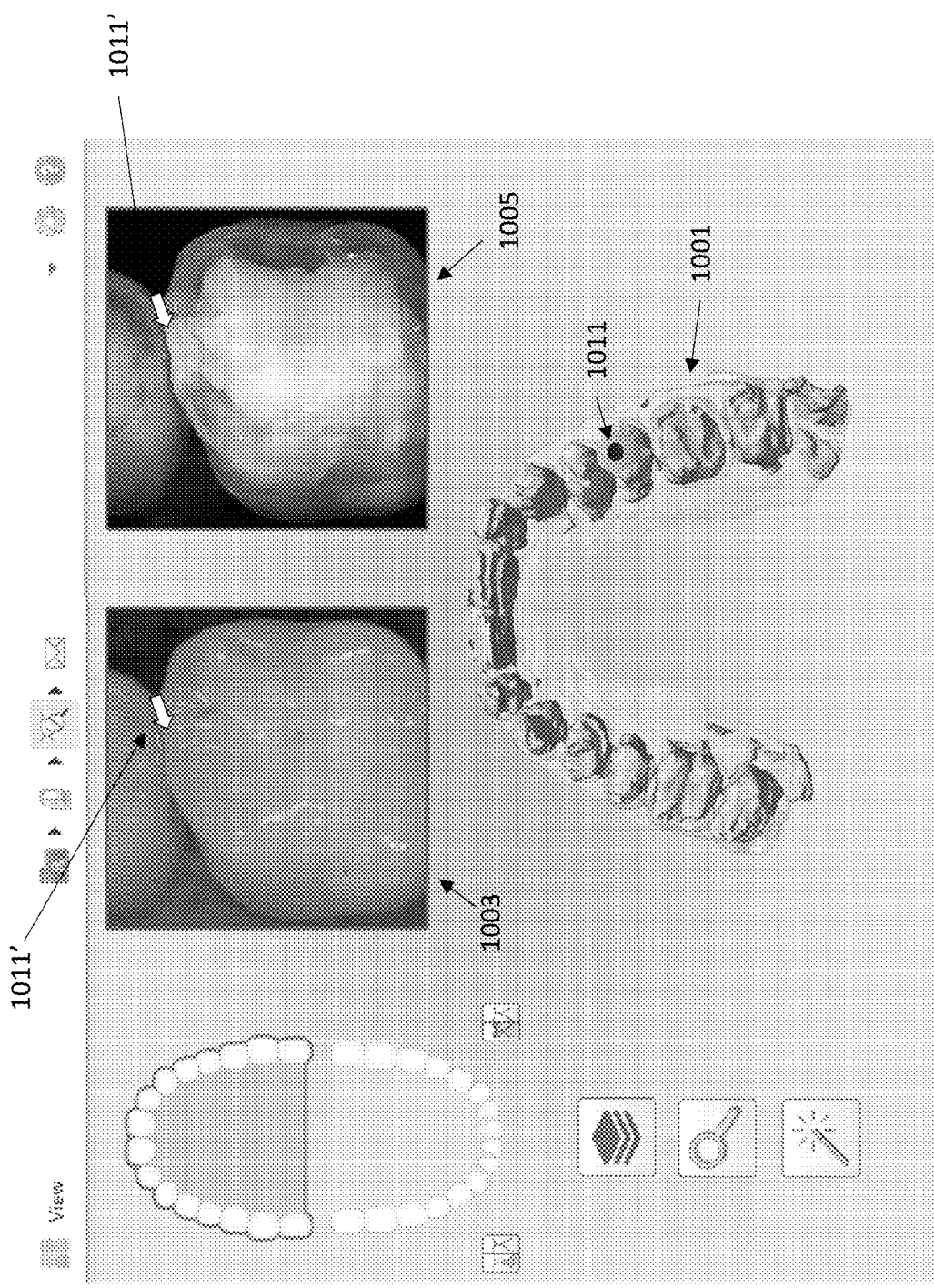
FIG. 10B show the user interface of FIG. 10A in which a region of the teeth has been marked/flagged as described herein.

FIGS. 10A and 10B illustrate a user interface showing marking of a region of interest from a 3D volumetric scan of a patient's oral cavity. In FIG. 10A, the user interface includes an image of the internal features 1001 (e.g., based on the near-IR absorption of the teeth), similar to FIG. 9B, discussed above. This view may be manipulated by user controls 1015, including sectioning tools, rotation, moving tools, etc. In FIG. 10A, two upper windows show a surface view 1003 and a volumetric (internal) view 1005 corresponding to the same region. This region may be selected. FIG. 10B shows the same features of FIG. 10A, but with a region marked or flagged 1011. As discussed above, the identification of the region to be flagged may be automatic or manual, or semi-automatic (e.g., confirmed by the user), and may be chosen to select a region for later monitoring. In FIG. 10B, the region may correspond, for example, to possible caries.

Monitoring of one or more internal regions of the teeth over time using the volumetric models of the patient's teeth taken with the devices described herein may be particularly helpful for predicting dental problems, including caries, cracks, tooth loss, gum recession, and the like. In particular, these methods and apparatuses may help the user (e.g., dentist, dental technician, orthodontist, etc.) inform and educate a patient so that the patient may take recommended treatments prior to developing more serious problems. There is a need for effective ways to show changes in teeth over time and to provide patients with information necessary to act early to prevent more complicated and potentially painful problems from developing. Many patients are otherwise reticent to undergo preventive procedures, particularly when there is not currently any associated pain or discomfort. For example, pre-cavitated caries are difficult to identify with current imaging techniques, and it may be particularly difficult to convince a patient to treat even when identified, since they typically present without pain. However, early stage treatment may be critical to avoiding more complicated and dangerous procedures later.

Dental caries are one type of problem that may be identified with the methods and apparatuses described herein. As shown and discussed above, caries may be identified from 3D volumetric models (such as those described herein) that penetrate into teeth using light (e.g., near-IR), one type of non-ionizing radiation. In the 3D volumetric models generated as described herein, e.g., using a near-IR light, typically in combination with a surface scanning (e.g., white light), the absorption coefficients of the internal regions of the teeth may indicate distinctions between dentin and enamel, and may reveal internal structures and flaws, including cracks, caries and the like. For example, regions of enamel that are less transparent than expected in the near-IR wavelengths may (e.g., having different IR optical properties), and particularly those that appear to extend to the surface of the tooth in the volumetric model may be identified manually or automatically as cavities or caries. Other irregularities in the enamel and/or dentin (e.g., based on the internal features of the teeth from the volumetric model) may be identified and may be characteristic of a problem in the teeth. Thus, the techniques described herein may be used for prognosis of dental issues such as caries.

As mentioned, any of the apparatuses and methods described herein may include improved methods for displaying of internal tooth features using the one or more volumetric models of a patient's teeth. For example, the methods and apparatuses described herein may be used to generate an estimate of enamel thickness for one or more of the patient's teeth. These estimates may be visually displayed, showing the outer surface of the teeth or a particular tooth, and may also show internal structures, including in sectional views or 3D internal views showing, e.g., the enamel, including the thickness of the enamel. This information may be used clinically to determine the need for, to help design and to help apply dental prosthetics, including veneers, crowns, and the like. Any of the methods and apparatuses described herein may be used, for example, to help prepare design a dental implant for a particular tooth or teeth.

Plaque and Calculus Detection and Visualization

The method and apparatuses described herein may also be used for the detection and visualization (including quantification) of plaque and calculus on the patient's teeth. Any of the intraoral scanners described herein may be used to detect plaque or calculus on the patient's teeth by using florescence imaging in addition to other imaging/scanning modalities including penetrative (e.g., near-IR) imaging. For example, and intraoral scanner may be cycled between different imaging modalities such as between white light and near-IR, including additional modalities such as florescence (e.g., laser florescence, etc.).

The use of fluorescence capabilities (and/or using current ones) by the intraoral scanner may allow detection of plaque and calculus on the surface of the teeth. In combination with 3D modeling using the data from the intraoral scanner, the plaque/calculus conditions can be modeled and visualized on the 3D model of the teeth, including the 3D volumetric modeling of the teeth. Plaque and/or calculus may be detected and may be displayed and highlighted as described above, and may be used before, during or after treatment. For example, a dental technician (e.g., dental hygienist) may use an intraoral scanner to detect and monitor the condition of the patient and the cleaning treatment. Data on plaque and calculus may also be used by any of the apparatuses described herein to determine and provide predictive models that may indicate plaque and calculus (e.g., tartar) generation rate and/or locations.

In some variations, plaque and calculus may be identified at least in part using florescence information. It has been observed that plaque may fluoresce under blue light (e.g., around about 405 nm). Any of the intraoral scanners described herein may include fluorescence information from which information about plaque and calculus may be used, and incorporated into a 3D model of the patient's teeth. For example, plaque and/or calculus may be visually displayed as a color and/or texture on the 3D model of the patient's teeth.

For example, a fluorescence signal can be obtained from an intraoral scanner using a dichroic filter having a large aperture amplification of fluorescence signal. This amplification may emphasize the fluorescence, thus enabling the detection, visualization and segmentation of plaque and calculus regions using RGB illumination, sensor and image. Alternatively or additionally, the apparatus may include a florescence source (e.g., an LED emitting at 405 nm) and corresponding filter(s) for detection of plaque and/or calculus. This may be integrated in the intraoral scanner, or added (e.g., as a sleeve, accessory, etc.) to be used with the scanner.

Alternatively or additionally, in some variations, depending on the wavelength of near-IR light used, the plaque and calculus may have a different absorption/reflection than enamel. This may allow the calculus and/or plaque to be differentiated from the enamel in the volumetric model. Further, the volumetric model may be used to detect material on the teeth, including calculus and plaque based on the surface smoothness and geometry. In variations in which calculus and/or plaque are not transparent to the near-IR frequencies used, the apparatus may differentiate calculus and/or plaque from the enamel using the volumetric model. Thus, the calculus and/or plaque may be segmented and differentiated from enamel.

The use of an intra-oral scanner to detect plaque and/or calculus may provide quantitative information and digital modeling. This may allow monitoring and comparison of plaque/calculus over time based on registration to 3D model, including real-time registration and/or display.

The acquisition of both fluorescence image and 3D scan on the same time and same position of the intraoral scanner (e.g., the scanning wand) allows for very accurate registration of the plaque/calculus regions and the 3D model. The concurrent scanning is described in greater detail, for example, in U.S. patent application Ser. No. 15/662,234, filed Jul. 27, 2017, and titled "INTRAORAL SCANNER WITH DENTAL DIAGNOSTICS CAPABILITIES". The accurate registration between different scanning modalities, such a white/visible light, penetrative (near-IR) light and/or florescence, may enable the apparatuses to define the borders of the calculus and/or plaque and may permit the apparatus to determine the volume/thickness in high resolution, allowing for both measuring the precise current situation and comparison/tracking relative to previous scans.

The methods and apparatuses described herein may take RGB images of the teeth at the same/similar time with taking 3D scans of the teeth. These scans may then be used to build the 3D model of the teeth/jaw, which may include the volumetric information (3D volumetric model). For example, RGB images may show emphasized signal of fluorescent surfaces, specifically plaque and calculus regions, due to specific characteristic of color and brightness of such surfaces, as mentioned. For example, the image of the outer surface (and in some cases the volumetric model) of the teeth may show regions having optical properties (florescence, brightness, color, etc.) indicative of calculus and/or plaque. In some variations, this emphasized signal may result from the spectral illumination that creates no reflection in visible light, but creates a significant fluorescence signal from plaque and calculus. For example, typical RGB illumination (using a common RGB sensor), may be modified to provide amplification of the fluorescence signal (e.g., in near-IR regions) on the outer surface of the teeth. This amplification can be achieved by, as a non-limiting example, a large aperture that enables IR signals to pass, and small aperture that enables the regular RGB (visible) spectrum to pass. This combination may produce color images with extra emphasis on fluorescent surfaces. Such fluorescence may manifest in characteristic colors and brightness of the desired regions indicating calculus and/or plaque on the teeth.

In any of the method and apparatuses described in which RGB images may be take that include florescence signals (e.g., at a wavelength in which plaque or calculus fluoresces), segmentation of the fluorescent regions may be performed on the image. For example, using the camera positions during acquisition of RGB and 3D scans (e.g., from the intraoral scanner), the fluorescent region may be registered with the 3D model (including the volumetric and/or just surface model) of the patient's teeth. This may result in a definition of relevant plaque and calculus regions on the final 3D model, which may further allow for definition of these regions, such as the borders of the calculus on the teeth, as well as 3D surface & thickness of the plaque.

As already discussed above, regions on the 3D model may be compared with previous/future scans of the same patient, which may show the development of calculus over time, and the effect of the calculus on the patient's teeth. The apparatus may automatically or semi-automatically mark (e.g., flag) these regions for monitoring. Thus, the size and shape of calculus for each tooth may be monitored. Alternatively or additionally, the thickness/depth of calculus may be compared with previous scans. Any of this information may be provided quantitatively and/or qualitatively, as discussed above. The thickness/depth of calculus may be compared with previous scans of clean teeth (including one or more earlier scans following cleaning by a dental professional). This may provide an estimate of the thickness of the calculus in later scans. As mentioned, measurements of the changes in the plaque, and particularly the calculus over time may be made, and this data may be used to monitor plaque and calculus progression on the patient's teeth, and may provide well as visualization of the development.

In general, the monitoring and visualization of the patient's teeth using the methods and apparatuses described herein may be used as part of a dental and/or orthodontic treatment planning. As already mentioned above, monitoring of calculus and plaque may be used to treatments including teeth cleaning. Scans may be performed prior to cleaning, during cleaning and/or after cleaning to provide guidance to the dental practitioner as to what regions to emphasize, focus on, or return to. Other treatments (coatings, caps, etc.) may be proposed based on the progression of plaque and/or calculus over time. Further, monitoring of any other feature or region of interest, including, e.g., caries, cracks, etc., as described above, may also provide treatment planning information. As discussed above, information about cracks and/or caries may be used to suggest treatments including restorations before potential issues develop further. In some variations, a digital model (e.g., surface and/or volumetric model) of the teeth may be modified using the volumetric information, and the modified model(s) used to design an orthodontic appliance or treatment plan. For example, a user may digitally remove plaque and/or calculus from a volumetric scan taken prior or during a treatment. The modified scan may be used to guide treatment, including further cleaning of the teeth, as necessary and to form or modify an appliance, so that the appliance (e.g., a dental aligner) may fit better.

Combination with Dental Tools

The intraoral scanners and volumetric modeling described herein may be used and/or combined with other dental tools (drills, probes, etc.). The combined tool may provide numerous advantages.

For example, described herein are drills that may be used in conjunction or combined with the intraoral scanners, and the use of 3D volumetric models. In some variations, a dental drill and an intraoral scanner may be combined; e.g., incorporating a laser drill or laser-accelerated water drill into an intraoral scanner. This combination may allow the dental professional using the tool to directly visualize the tooth as and before it is drilled, providing real-time feedback to the user. In one example, near-IR light may be applied to the probe head of the drill (e.g., laser drill) to provide imaging into the tooth, which will allow direct forward-looking imaging prior and/or during drilling. The enamel and dentin in the direct path of the drill may be imaged. The density information can be used to inform the clinician when they have reached the dentin layer of a tooth or a certain depth inside the dentin, or when diseased regions have been removed. For example, the density information can be used to provide haptic feedback to the operator, since tactile feedback is much more limited when using a dental laser versus a traditional headpiece.

Figure 7:
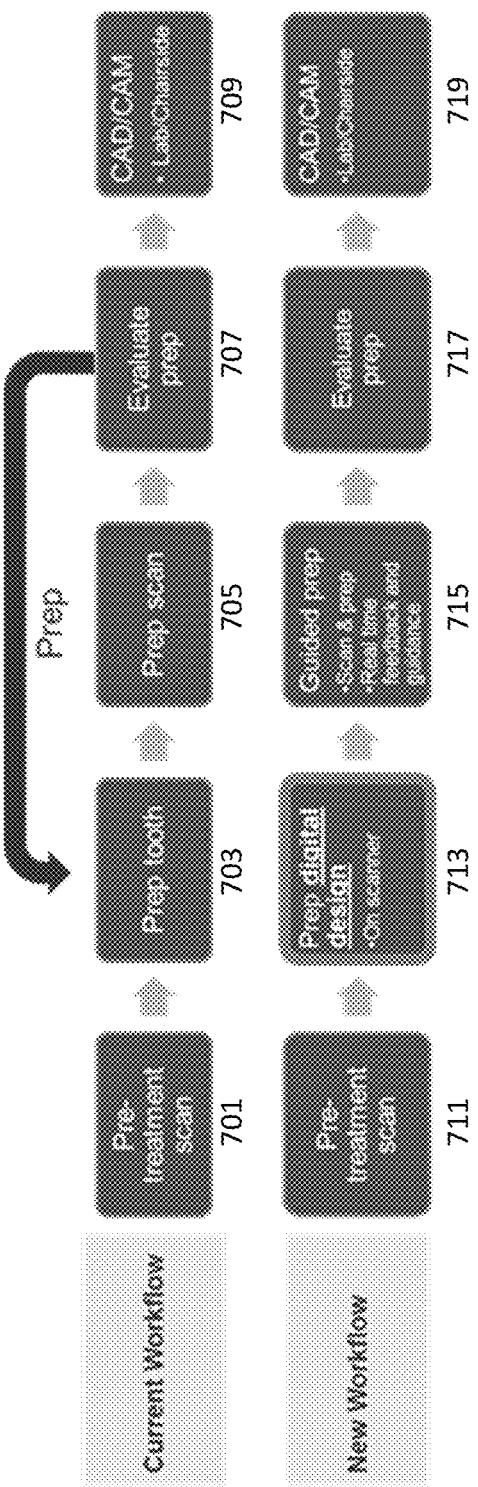
FIG. 7 is a comparison between a typical computer-aided design/computer-aided manufacturing (CAD/CAM) method for dentistry, and a method implementing the 3D volumetric scanning and modeling as described herein.

The methods and apparatuses including intraoral scanners and volumetric modeling as described herein may also be integrated into computer-aided design/computer-aided manufacturing technology for dentistry, as described in FIG. 7. For example, dental implants, such as crowns (e.g., ceramic crowns) may be fabricated for an individual patient using computer-aided design and computer-aided manufacturing (CAD/CAM) apparatuses and procedures. For example, traditionally CAD/CAM laboratory manufacturing ("current workflow" in FIG. 7) may include pre-treatment scanning of the patient's teeth 701 or an impression of the patient's teeth, such as a caries-free scan of the jaws. The teeth may then be prepared for the crown 703, and then re-scanned 705 and evaluated 707. Finally, the crown may be made using CAD/CAM. The software for the CAD/CAM may receive the scanned information from the scanner and may process it for use in forming the design and performing the manufacture. The use of CAD/CAM software may provide restorations comparable to conventional restorations in all aspects, including in aesthetics, however the current methodologies may require repeated steps for evaluating and preparing the tooth, as shown by FIG. 7, and typically require the user to perform these steps manually.

As shown in the "new workflow" on the bottom of FIG. 7, this method may integrate the 3D volumetric modeling described herein to simplify and improve CAD/CAM of a patient's teeth. For example, the preparation may be digitally designed, and this process may be automated (fully or semi-fully, so that the user may approve and/or modify the process). For example, in FIG. 7, the pre-treatment scan 711 may be performed using an intraoral scanner that directly communicates with the CAD/CAM apparatus, or the intraoral scanner may include CAD/CAM capabilities. In this example, the tooth preparation 713 may be fully digitally designed based on the scan performed, and the scanner may guide the preparation of the tooth 715. This may be done in real time with direct feedback and/or guidance from the apparatus, which may integrate the scanner. The scanner may then be used to evaluate the preparation 717, on in some cases this step may be integrated fully into the guided prep step 715, therefore removing the need for the post-prep evaluation. Finally, CAD/CAM may be used to prepare the crown (or other dental appliance) for the correctly prepared tooth 719.

Root Canal

The methods and apparatuses for 3D volumetric modeling of the patient's oral cavity (e.g., 3D volumetric modeling of the teeth) may also be used to modify a root canal procedure. Typically, root canal procedures require numerous x-rays to provide images into the teeth prior to, during, and/or after the procedure. The methods and apparatuses described herein may remove or reduce the requirement for x-rays in the specific example of root canal procedures. Specifically, as described herein, an intraoral scanner including penetrative wavelengths (e.g., near-IR) may be used to examine within a tooth, including within the root of the tooth during the procedure. This may allow identification and localization of the canal. For example, a tooth may be prepared for the root canal by, for example, drilling a hole through the crown into the tooth. The hole may be drilled with the guidance of the volumetric imaging described herein either during or interposed with the drilling. For example, a tooth (e.g., molar) may have an initial hole drilled into it to expose the camber within the tooth. An intraoral scanner including near-IR may be used to image the tooth, including imaging through the hole that has been drilled into the tooth, to visualize into the pulp chamber. The scanner may be oriented, automatically or manually, to image down into the chamber, which may allow visualization of the roots within the chamber. The initial drilling into the teeth may be limited to penetrate the enamel and expose the inner chamber, and visualizing into the chamber so that regions having different optical properties (at any wavelength, including in particular the near-IR wavelengths) may penetrate into the chamber despite calcifications and/or infection, to allow imaging of the roots from within the tooth itself. The nerve chambers of the root may be identified as being more or less dense than the surrounding regions within the dentin and enamel. By removing the roof of the chamber to expose the inner pulp region of the tooth, the intraoral scanner may visualize through the drilled opening to provide additional volumetric information, including the locations, curvature, and trajectory of the tooth root. Detection of hidden canals and accessory canals may be facilitated by this additional visualization information. This information may then be used to guide the therapy.

For example, in some variations, the method may include taking, using an intraoral scanner as described herein, a 3D volumetric model of the patient's teeth either before or after drilling to form an opening into the target tooth (e.g., for which a root canal will be performed). The drilling may be done with or without guidance from an intraoral scanner, as described above. The inner chamber of the tooth may be visualized using the intraoral scanner, e.g., through an opening drilled from the crown of the tooth. The apparatus may then determine the locations of the horns of the pulp chamber for the tooth. Any of the methods described herein may be used in combination with x-ray information. Treatment planning may be performed by the apparatus to determine the shape and/or location of the pulp horns, pulp chamber, and roots to map out a treatment plan for drilling/tissue removal that avoids overthinking or breaching the lateral sides of the tooth. This treatment plan may then be used to guide the user in drilling on the teeth, and/or for automating the drilling. In some variations the drill may be directly guided by imaging, e.g., using the hybrid drill/intraoral scanner described above. Alternatively or additionally, robotic assistance may be provided using the treatment plan. In some variations, the procedure may be performed manually, and the drilling may be done in small increments, with visualization between drilling steps to confirm the treatment path, and avoid over-drilling, as well as confirming that the entire region has been drilled and infected pulp removed. Additional visualization (including using a contrasting agent) may be used.

In general, any of the methods described herein, including the root canal methods described above, may be used with one or more contrasting agents during imaging. For example, contrasting agent may include material applied to the outside of the tooth (or into a hole or opening in the tooth, including holes drilled into the tooth). Contrast agents that absorb or reflect in the near-IR, or other wavelengths use by the intraoral scanner may be used. Preferably contrast agents may be used that are distinguishable at some of the imaged wavelengths, but not all of them, to provide differential imaging. For example, contrast agents may be visualizable under white light, but not near-IR; alternatively, a contrast agent may be visualizable under near-IR but not white light, or under some wavelengths of near-IR but not others for which images are taken. Contrast agents that preferably attach mix or coat with one or more targets within the teeth or oral cavity may be used. For example, a contrast agent that selectively binds to one or more of: bacteria, plaque, calculus, gingiva, pulp, etc., may be used. In use, the contrast agent may be applied to the teeth/oral cavity, rinsed, then visualized (or visualized without rinsing). For example, a contrast agent that absorbs IR light may be used for inclusion as part of, or mixed in with a material forming, e.g., a dental implant (e.g., to fill a cavity, cap a tooth, fill a root canal, etc.,) to create an IR contrasting filler material that may be easily visualized when scanning as described herein.

Also described herein are methods of determining improvements in soft tissue around the teeth using the apparatuses and methods for generating 3D volumetric models of the teeth, as described herein. For example a gum recession may be monitored and/or quantified, and may be observed over time using these methods and apparatuses. In addition to the direct visualization of plaque and/or calculus as described above, the methods and apparatuses described herein may also or alternatively detect the effect on the teeth, including recession of the bone due to plaque and calculus. Diseased regions, may be visualized directly. In some variations a contrast agent may be used to provide additional contrast for the intraoral scanner to detect diseased regions. Scanning of the surface of the gingiva may identify inflamed and/or discolored regions that may be indicative of gum disease. This information may be combined with the 3D volumetric modeling of the teeth, including the location of plaque and/or calculus, as discussed above.

FIGS. 8A and 8B illustrate an example of a monitoring, over time, gum (gingival) recession. In this example, the display may show the 3D model of the teeth and a comparison between the original scan, and a subsequent scan, taken 2-3 years later. In FIG. 8A, the two scans have been aligned and compared, and differences shown by a color indicator, e.g., a heat map. In FIG. 8, darker colors (which may be shown in color, e.g., red) show recession of the gingiva to a greater degree. The circled region B in FIG. 8A is shown in greater detail in FIG. 8B for the later scan. Although FIG. 8 illustrates primarily surface features (e.g., gingiva position), volumetric information may be used to generate this information, e.g., showing changes in gingiva thickness and/or vascularization, enamel thickness, etc.

In addition to guiding the user and/or dental technician based on the scans (e.g., showing plaque, calculus and/or inflammation in particular), these methods and apparatuses may be used by the dental professional to rate, rank or quantify the removal of plaque and/or calculus, either immediately following a treatment, or over time. This may provide a metric against which treatments may be judged. The scan information may also be used to provide information to the patients, including a map or guide for home treatment, including which areas to focus on brushing, flossing, etc. The guide may include one or more images from the 3D volumetric model, for example. Guidance information about what teeth or oral cavity regions to focus home dental care (e.g., brushing) on may be provided to an electronic toothbrush that may also help guide the patient in brushing based on identified regions.

The methods and apparatuses described herein may also be used with patient's already having a dental appliance installed on the teeth, including braces, bridges, and the like. For example, in some variations the patient may include 3D representations of the dental appliance, and may provide information to help design or modify future dental devices (e.g., retainers, aligners, braces, etc.).

In particular, the methods and apparatuses described herein may be use to provide very accurate volumetric and surface information about the patient's teeth that may be useful for treatment planning of any type of dental treatment. In some variations the methods and apparatuses described herein may be useful for treatment planning of an appliance, such as an aligner or retainer, that is optimally worn in close proximity to the patient's teeth. For example, a method and/or apparatus that includes a 3D volumetric scan of the patient's teeth may be used to subtract out or remove from the 3D model of the teeth, any plaque, calculus and/or food debris that might be present at the time of the 3D scan. By digitally subtracting out any plaque, calculus, and/or food debris present, the volumetric information may be used with a virtual representation of an aligner, retainer, night guard, or other device, and the fit improved prior to fabricating, applying or wearing the apparatus.

The gingival tissue surrounding the teeth, being of different density (or different optical absorption/reflection properties) than the enamel, may also be identified and characterized with greater accuracy, so that the junction between the inner contour and the tooth surface can be identified. By doing this, the shape of the tooth surface beneath the gingival tissue can be accurately characterized so that predictive models of tooth movement can have more accurate representations of the teeth as portions of the teeth not initially visible become gradually exposed as the teeth align. In other words, some parts of the teeth may be initially obscured by the gingival tissue, but as the teeth straighten, the gingival tissue migrates, and the previously-covered regions are exposed. By detecting the tooth regions beneath the gingival tissue accurately, the future state of the teeth after the gingiva has migrated can be more accurately modeled.

The methods and apparatuses described herein may also be sued to detect, diagnose, and/or treat disorders of the oral cavity.

For example, the 3D volumetric scanning and modeling methods and apparatuses described herein may be used to detect and/or treat salivary stones (e.g., plugging of the salivary ducts). These glands, which may be located near the molars and under the patient's tongue, may be scanned using the intraoral scanners described herein. These scans may penetrate the soft tissue and may detect the hard, stone-like formations (i.e., sialoliths, salivary-gland stones, or duct stones) that are calcified structures that may form inside a salivary gland or duct and block the flow of saliva into the mouth. The methods and apparatuses described herein may be used to identify these structures and/or may guide and/or confirm removal of these stones.

In addition to or instead of the use of the apparatuses and methods descried herein to identify, diagnose and/or track regions, including pre-cavitation caries, crack, etc., the methods and apparatuses described herein may also or alternatively be used to identify and manipulate regions that have already been modified. For example, fillings, attachments (for attaching an angler, braces, etc.), braces, retainers, etc. and any other structures may be identified within the volumetric model and/or displayed. For example regions of enamel and/or enamel-like restorations may be displayed differently in the volumetric model. These regions will typically have different optical properties, including different scattering/absorption of the near-IR (and in some cases visible light) compared to each other and/or other regions of the oral cavity, including the dentin. Such regions may be manually, automatically or semi-automatically identified, and may be segmented and/or separately manipulated. For example, in some variations these regions (e.g., attachments/cement, etc. for an aligner or other appliance) on the tooth may be identified for removal by the dental practitioner, and the 3D volumetric model or data (images) taken from it may be provided to guide such treatment. They may also or alternatively be digitally subtracted to provide a better fit for a new appliance once removed. A subtracted view may also or alternatively be provided to a patient.

In some variation the internal structural integrity of an artificial dental structure or modification (e.g., dental bond, filling, etc.) may be determined using the volumetric model(s) described herein. For example, a volumetric model may include internal detail of an artificial dental structure, such as the structural detail within a filling, bond, etc., or the interface between the natural tooth (enamel, dentin, etc.), and this information may be presented or shown to the user in detail to allow an assessment (or to allow automatic assessment) of the condition of such artificial dental structures. This may facilitate their removal, repair and/or replacement.

The 3D volumetric models of the teeth (and method and apparatuses for generating them) may also be used as a diagnostic or detection tool for future tooth sensitivity. For example, an abfraction is a form of non-carious tooth tissue loss that typically occurs along the gingival margin. The abfraction lesion may be a mechanical loss of tooth structure that is not caused by tooth decay that may occur in both the dentin and enamel of the tooth. These are believed to be caused by repetitive stress cycles from the patient's occlusion, and exacerbated by aggressive brushing. The 3D volumetric models of the teeth enhanced by density analysis of the enamel and dentin near the gingival line may provide an early indicator of these lesions. For example, an apparatus may examine the volumetric model to identify the initial stages of formation for these crescent-shaped lesions. Multiple 3D volumetric models taken over time may indicate the rate of progression of these lesions. A system may be configured to automatically or manually identify them; as described above, they may be automatically or semi-automatically flagged.

Thus, the apparatus and methods may identify and alter the user that such a "hotspot" leading the future tooth sensitivity may be occurring, and may provide for treatment plans to slow, stop or reverse the progression of the lesion. Tooth sensitivity can result from these small fractures and the exposed dentin. Detection may be triggered by identifying the characteristic crescent shape that develops in the more mature lesions, however earlier detection may be made by identifying regions of thinning in the enamel and/or dentin (e.g., near the gingival line), which may progress over time. The apparatuses and methods may flag and/or assign risk based on the actual thickness and/or the progression of changes in the thickness.

The methods and apparatuses described herein may also be used to detect the development of acid reflux, based in part on characteristic wear patterns, and/or changes (e.g., over time) in the enamel thickness of the patient. For example, acid reflex while a patient sleeps may result in the gradual erosion of the patient's teeth in a characteristic pattern (e.g., from the back of the teeth, on the lingual side. As similar pattern may develop with bulimia. The volumetric models of the patient's teeth taken, e.g., by near-IR, may provide an accurate mapping of the enamel density and thicknesses of all of the patient's teeth. Thus, a method of detecting acid reflux (or bulimia) may include detecting (including detecting over time) characteristic thinning of the enamel of the patient's teeth in the rear, lingual region. The more proximal, lingual region of the teeth may have an unusually thinner (or thinning) enamel thickness, compared to more anterior (forward) regions on the opposite, buccal, side of the patient's teeth.

The methods and apparatuses described herein may also be used to detect thin enamel regions from occlusal wear due to chronic grinding of the patient's teeth and/or predict tooth sensitivity that may result from this grinding. 3D volumetric models of the patient's teeth may show a snapshot of the occlusal thickness of the patient's enamel and the proximity of the dentin to the occlusal surface. Further, multiple scans taken over time may show the loss of enamel in the occlusal surface. This was mentioned above as one indicator that may be automatically, manually or semi-automatically marked or flagged. For example, a flag can be set whenever a region>0.5 $mm^2$ develops within 0.5 mm of dentin, and the regions of the digital model highlighted. This allows any regions which satisfy the flag criteria to be visualized and/or monitored. Given a patient's age and in some variations gender, as well as the changes in the enamel thickness over time, an estimate of the wear rate over time may be provided, along with proximity to dentin regions, and thus an estimate or prediction of the tooth sensitivity or pain may be made. Grinding of teeth may also be an indicator of other issued, including sleep apnea. For example, sleep apnea may also be detected from 3D volumetric models of the patient's teeth, particularly over time. Many patients with sleep apnea grind their teeth (e.g., in a forward and/or side to side motion), which may result in a pattern of erosion of the teeth. Thus, the methods and apparatuses described herein may be used to help diagnose or confirm sleep apnea.

In general, any of the methods and apparatuses described herein may be used with non-human patients. For example, any of the methods and apparatuses described herein may be used as with veterinary patient's (e.g., animals) to determine, for example, the state of the animals teeth, including wear on the teeth.

The methods and apparatuses described herein may also be used to provide an estimate of risk for the patient in developing fractures in the teeth, and/or the development of tooth sensitivity. For example, a the 3D volumetric models of the teeth described herein may be used to identify malocclusions in the teeth and resulting wear and/or cracking of the teeth, based on the mechanical estimates of the tooth thickness and wear pattern. Functional information such as chewing pattern and articulation forces may also be integrated into the assessment. Wear patterns may be identified and shown as 'hotspots' for example on images generated from the 3D representation of the patient's teeth. This may be displayed to the patient as information, including as information warning of potential risks. High risk regions may be identified to the patient along with an explanation of the potential risk.

In general, the methods and apparatuses, and particularly the monitoring and comparison, over time, of 3D volumetric models including information about the internal structures of the teeth (e.g., enamel and dentin distribution within the teeth) may be used to identify, monitor, diagnose, and guide treatment of a variety of disorders in addition to those mentioned above. For example, dentin dysplasia, enamel dysplasia, etc. These methods also allow the identification of multiple different types of enamel within the patient's teeth, including regions having different amounts hydroxyapatite, amelogenins and/or enamelins, or differently organized regions of these, including regions that are homogenous or non-homogeneous, and that may have different optical properties for the near-IR wavelengths used for imaging.

Interactive Display of 3D Model of a Patient's Dental Arch

As already described (and shown in the figures above), the methods and apparatuses described herein may allow a user to virtually scan a patient's dental arch. In particular a 3D model of the patient's dental arch(s), which may be volumetric, surface, or both (or in some variations an abstracted or generic model), may be used in conjunction with images taken, e.g., using an intraoral scanner, from various positions around the dental arch. These images may be images that were used to generate the 3D model of the dental arch. The images may be tagged and/or arranged in the data structure to indicate their corresponding position or region or angle relative to the 3D dental arch model. In some variations, the 3D model and the images taken may be maintained as a data structure, however it is not necessary that the 3D model be included with the images as a single data structure.

Figure 13:
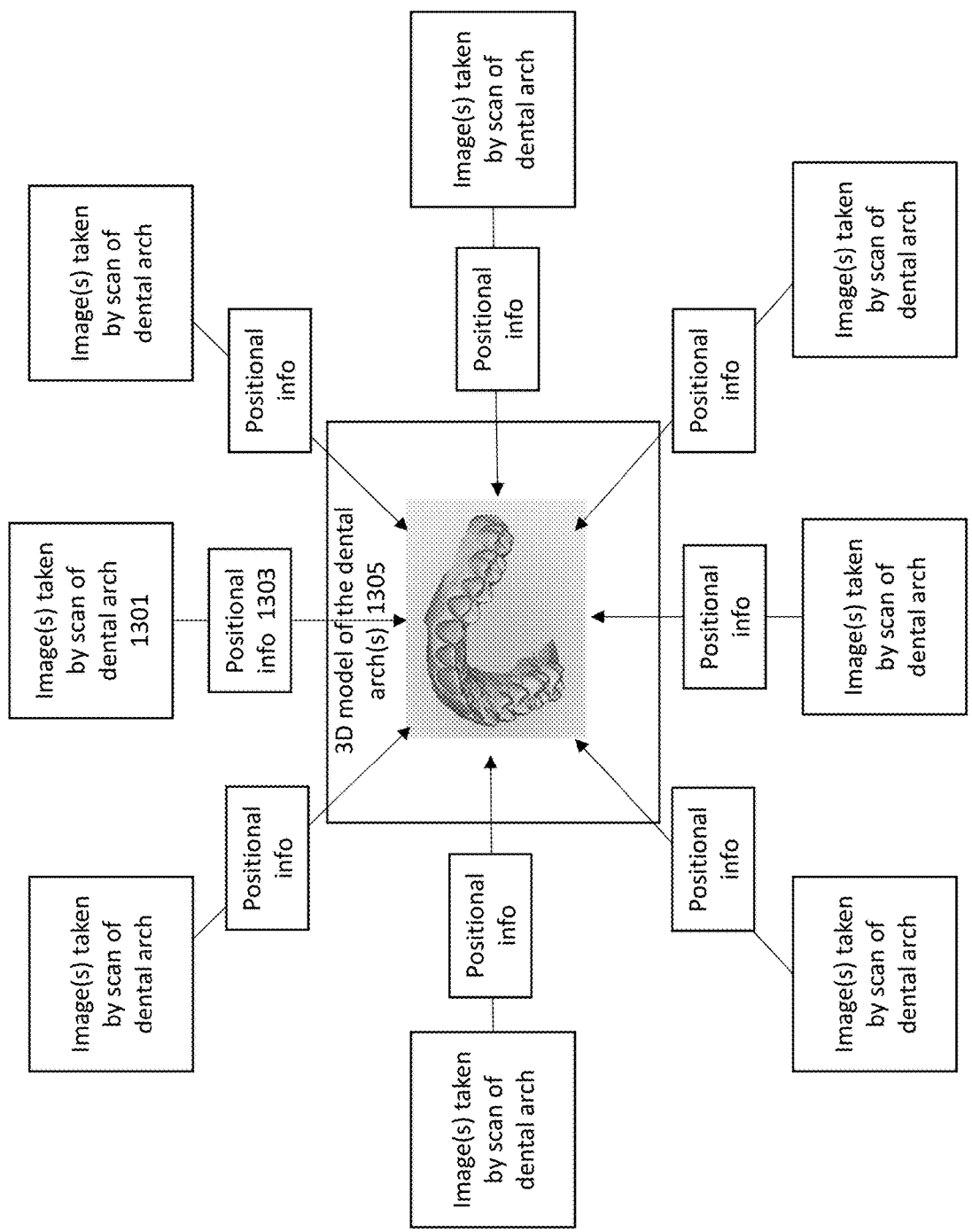
FIG. 13 is a schematic illustration of a data structure including a 3D model of a patient's dental arch(s) and associated 2D images taken (e.g., via intraoral scanner) of the dental arch at a large number of positions around the dental arch.

For example, FIG. 13 is an example of a data structure that includes one or more dental arch models 1305 as well as a plurality (e.g., greater than 50, greater than 100, greater than 200, greater than 500, greater than 750, greater than 1000, greater than 10,000, etc.) of one or more (e.g., sets) of images taken from positions around the patient's dental arch. In some variations both visible light and near-IR (or near-IR and other modalities) images 1301 may be shown and may share positional information. The positional information typically includes the region of the dental arch (e.g., in x, y, z coordinates, such as the coordinate of a center point of the image relative to the dental arch) from which the image was taken, as well as the angle (e.g., roll, pitch and/or yaw, or radial coordinates, etc.) relative to the plane of the dental arch ("positional info" 1301). In some variations the scans may be composites of multiple scans (e.g., averages, blends, etc.) that are combined and stored in the data structure. The 3D model may be formed by virtually "stitching" the scans together to form the 3D model.

The data structure may be stored in a compressed configuration; although it may contain a large amount of data, the compression and organization of the data structure may allow it to be manipulated for display. For example, FIG. 12 illustrates one method of interactively displaying a 3D model of a patient's dental arch using a data structure such as the one schematically shown in FIG. 13.

Figure 12:
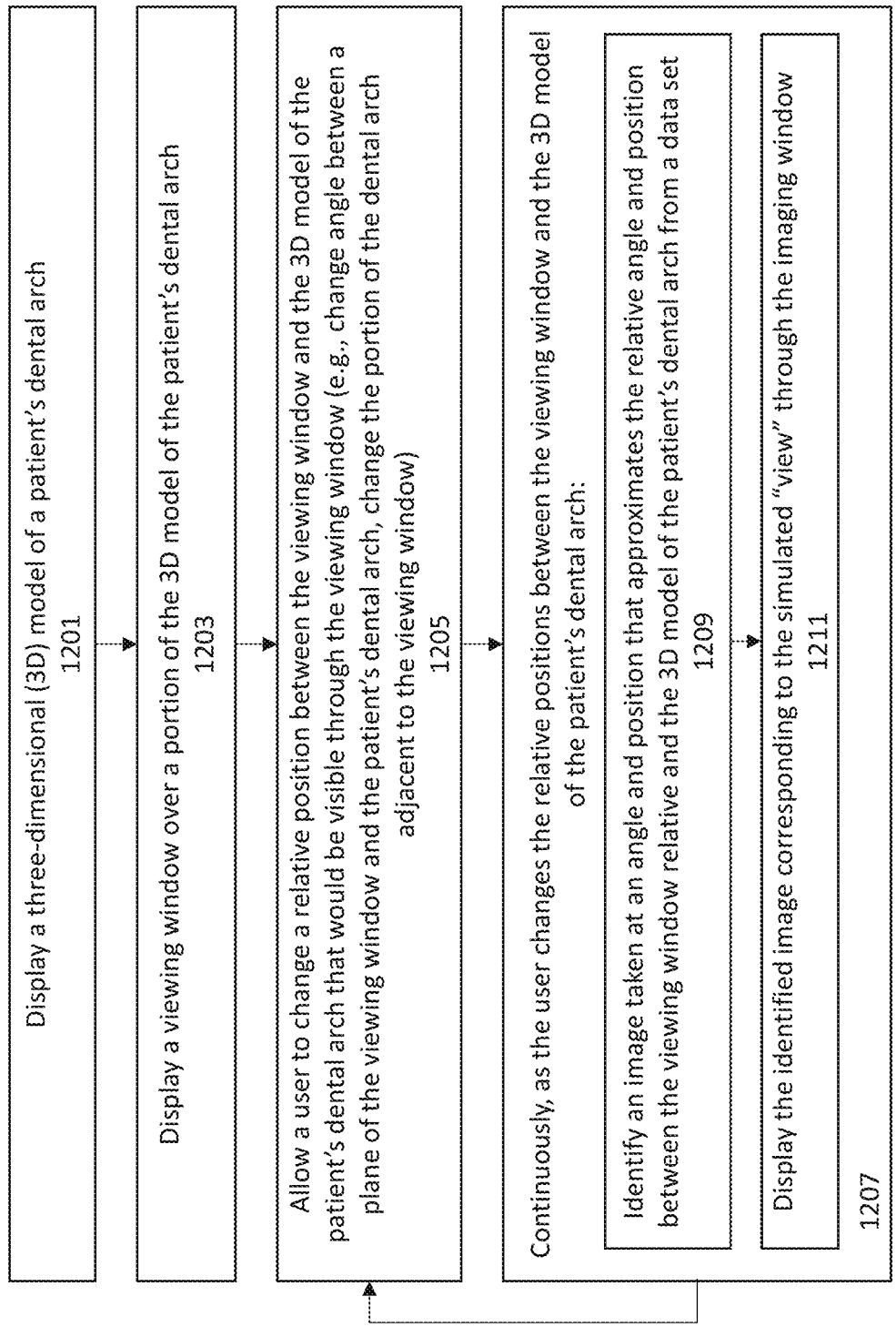
FIG. 12 is an example of a method for allowing a user to virtually scan a patient's dental arch. This method may be performed in real time or near real time.

In FIG. 12, the method includes displaying the 3D model of the patient's dental arch 1201 and displaying on the 3D model a viewing window 1203. The user may then be allowed to continuously move the two (e.g., either or both the viewing window and the 3D model) so that the teeth of the dental arch may be virtually viewed "though" the viewing window in greater detail in a nearby view 1205. The angle of the viewing window as well as the location of the viewing window along the dental arch may be changed by the user, e.g., moving continuously over and/or around the 3D model of the dental arch 1207. As the viewing window/dental arch are moved relative to each other, a corresponding image (or images), such as a near-IR image, taken at a position relative to the dental arch corresponding to the position of the viewing window, may be identified from the data structure/data set (e.g., FIG. 13) 1209. The corresponding image(s) may then be displayed 1211, and this process may be iteratively repeated as the viewing window is moved over and along the 3D dental arch model.

In some variations, the data structure may be configured or arranged topographically or in an indexed topographic manner; thus images of adjacent regions may be linked or ordered in the data structure, simplifying the method.

FIGS. 14A-16C illustrate examples of one variation of a user interface that may allow the user to virtually scan a 3D model of the dental arch, showing corresponding images (e.g., near-IR images) as described in FIG. 12. As mentioned above, the near-IR images may be viewed by the user to identify manually (or in some variations automatically) identify one or more structures/defects and/or actionable dental features, including dental caries, cracks, wear, etc. The display of corresponding 3D dental arch model and visible light images of the same regions may both give perspective and allow for immediate comparison with the patient's teeth, simplifying and powerfully augmenting dental analysis.

Figure 14A:
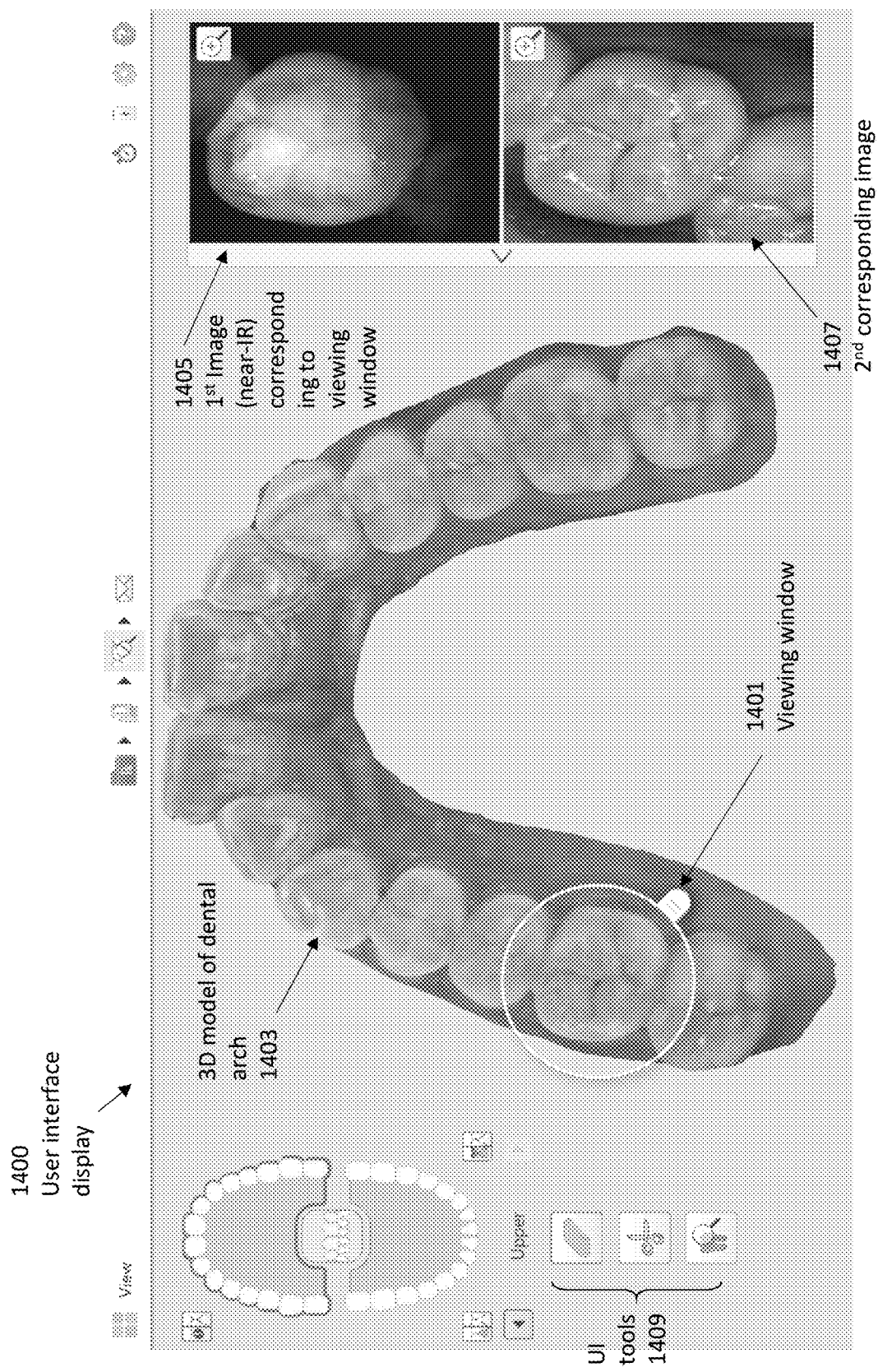
FIG. 14A is an example of a user interface allowing the user to virtually scan over the 3D model of the dental arch, showing corresponding light and near-IR (e.g., external and internal) regions in detail as the user scans over the 3D dental arch; the user may use one or more tools to move the dental arch (e.g., rotate, translate, etc.) and/or the viewing window; the corresponding light and near-IR images may continuously or near-continuously update as the position of the viewing window and dental arch change. A pair of imaging windows are shown adjacent to the view of the 3D model of the dental arch.

For example, in FIG. 14A, the display is shown as a user interface 1400 including a dental arch model 1403 (3D dental arch model) reconstructed form scans of the patient's teeth and stored, along with many or all of these scans, in a data structure. As already mentioned above, it is not necessary, but may be helpful, for the 3D dental arch model to be included in the data structure with the plurality of images. Further, the 3D dental arch model in this example is constructed from the scans of the patient's teeth, however, is should be clear that the 3D dental arch model may be non-representative, and yet may be used to select the 2D views to be displayed, as described herein. A viewing window 1401, shown as a loop or circle, may be moved over or along the 3D model of the dental arch; as the viewing window is moved, each of two image displays 1405, 1407 are updated with images corresponding to the position (both the region of the dental arch and the angle of the dental arch relative to the plane of the viewing window. In FIG. 14A the first (upper) image 1405 is a near-IR image and a corresponding (taken at the same approximate time/location) visible light (e.g., color) image is shown in the bottom image 1407. Alternatively displays are shown in FIGS. 14B and 14C, showing just a single image each; in FIG. 14B an enlarged near-IR display image is shown, while in FIG. 14C a single, enlarged visible light display image of the region corresponding to the imaging window view is shown.

The user interface may also include tools 1409 for manipulating the display (e.g., rotating, moving the dental arch and/or viewing window, modifying, marking, etc., the images and/or 3D model, saving, opening/recalling images, etc.

Figure 15A:
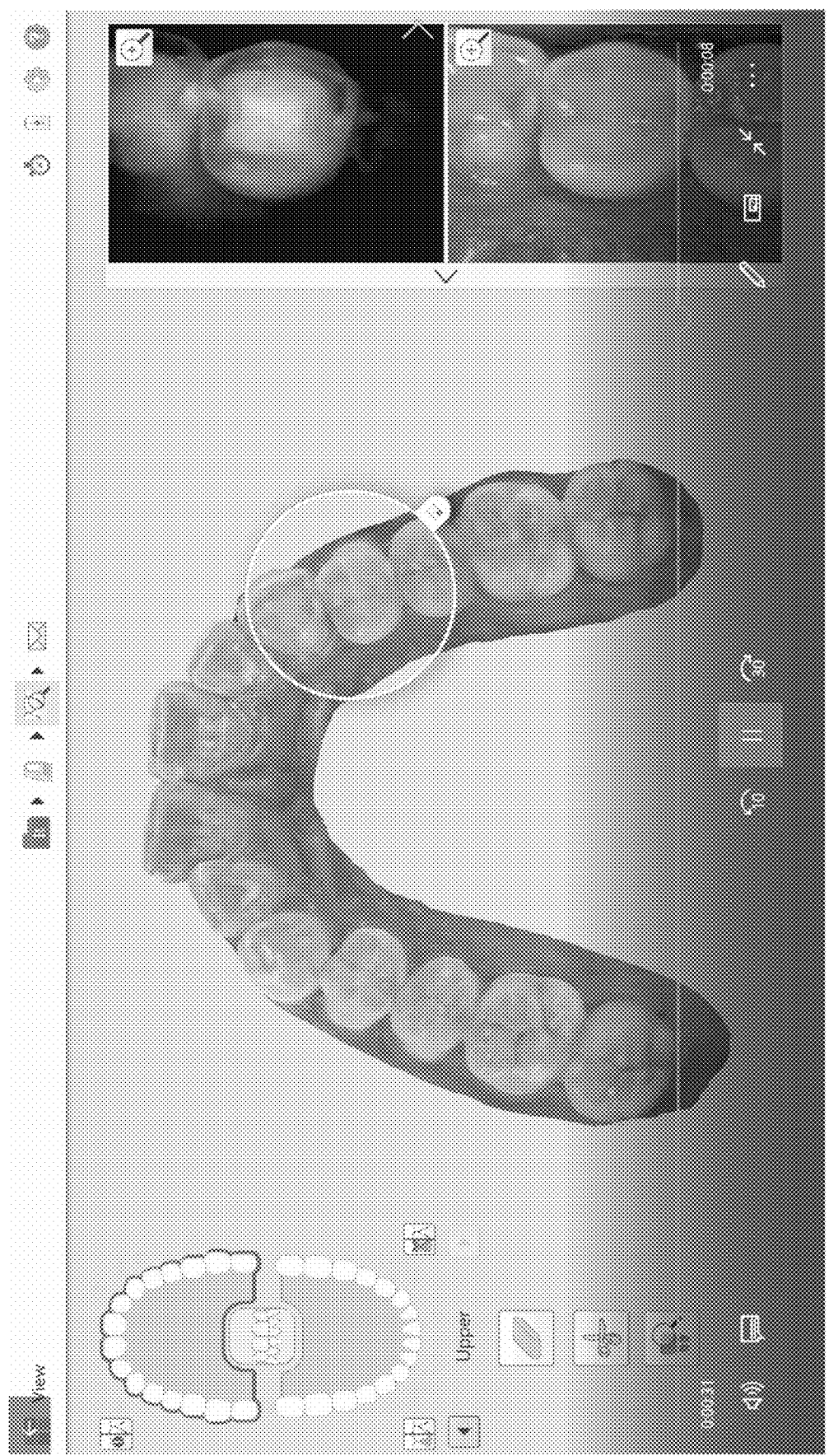
FIG. 15A is similar to FIG. 14A, showing an example of a 3D model of the outer surface of a dental arch, and a viewing window relative to the dental arch. A pair of image display windows are adjacent to the 3D model of the dental arch. The user may move the viewing window over the dental arch (and/or may move the dental arch relative to the viewing window, changing the image(s) shown in the two display windows. The upper display window shows a near-IR image corresponding to the dental arch at the position and angle of the plane of the viewing window; the bottom display window shows a corresponding light image (which may be in color).
Figure 15B:
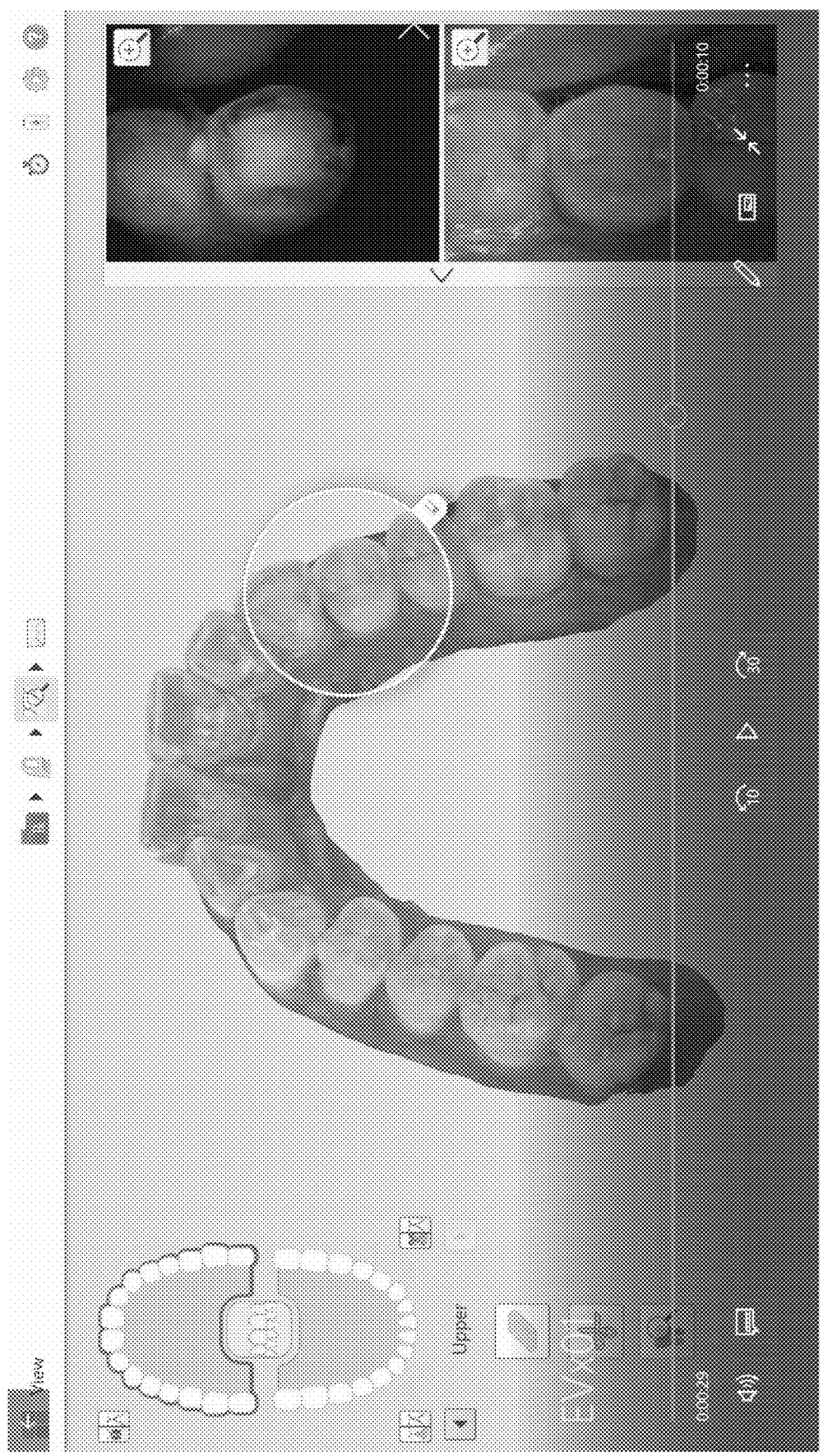
FIG. 15B shows another image of the dental arch shown in FIG. 15A, with the dental arch rotated lingually relative to the viewing window; the corresponding near-IR images (upper right) and visible light (lower right) adjacent to the 3D model of the arch are updated to show the slightly rotated view, allowing the user to virtually scan the dental arch and show both external and internal views in real (or near-real) time.

FIGS. 15A-15B illustrate an example of moving the viewing window over the teeth and changing/updating the corresponding images. FIG. 15A shows the image of the dental arch with corresponding near-IR and light images as "seen" through the viewing window at a middle region of the dental arch. In FIG. 15B the dental arch has been rotated by the user (or alternatively, the viewing window has been rotated relative to the dental arch lingually) so that the viewing window is slightly lingually positioned relative to FIG. 15A; the corresponding views (near IR and visible light) have bene updated in real time to show this change of the relative position of the viewing window.

Figure 14B:
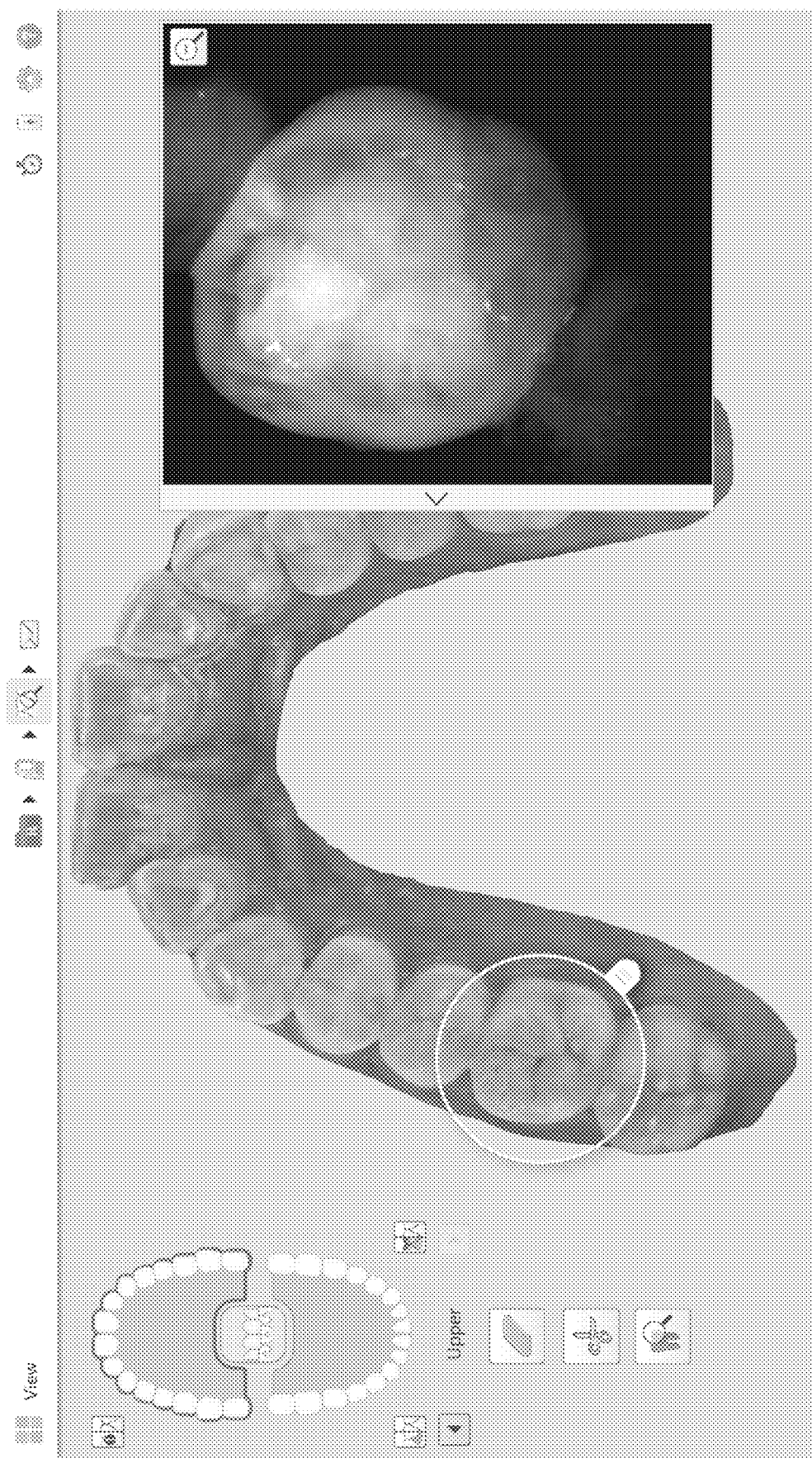
FIG. 14B is an alternative display showing a single large image window over or adjacent to the 3D image of the dental arch.
Figure 14C:
FIG. 14C is an alternative display showing a single large image window over or adjacent to the 3D image of the dental arch.
Figure 16A:
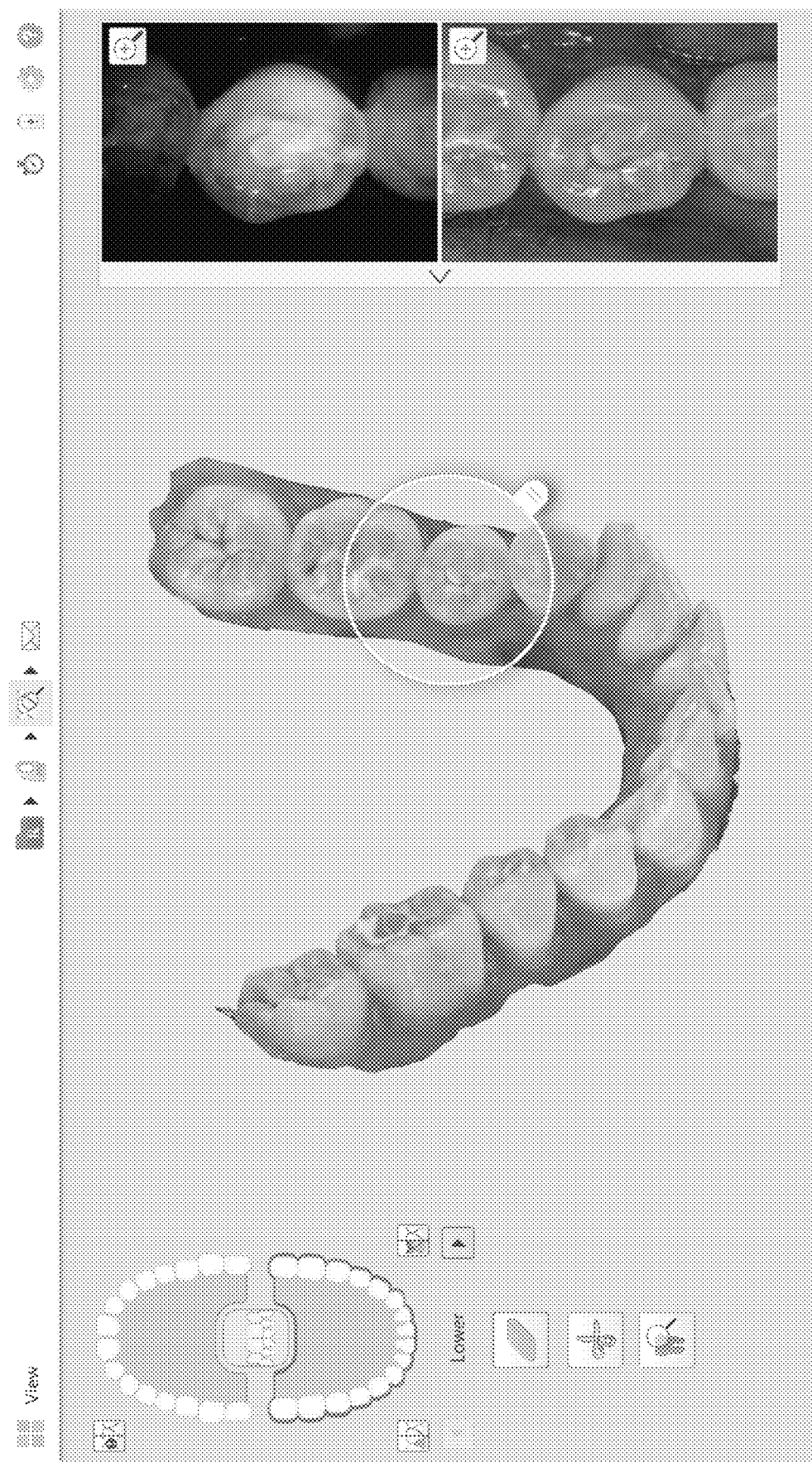
FIG. 16A is another example of a method of showing a 3D model of a dental arch (shown as the lower arch in this example, e.g., by selecting the lower arch display control in the upper left of the user interface) and showing focused views of near-IR and visible light images corresponding to the viewing window region that may be moved over/across, and around (lingual-occlusal-buccal) the model of the patient's arch.
Figure 16B:
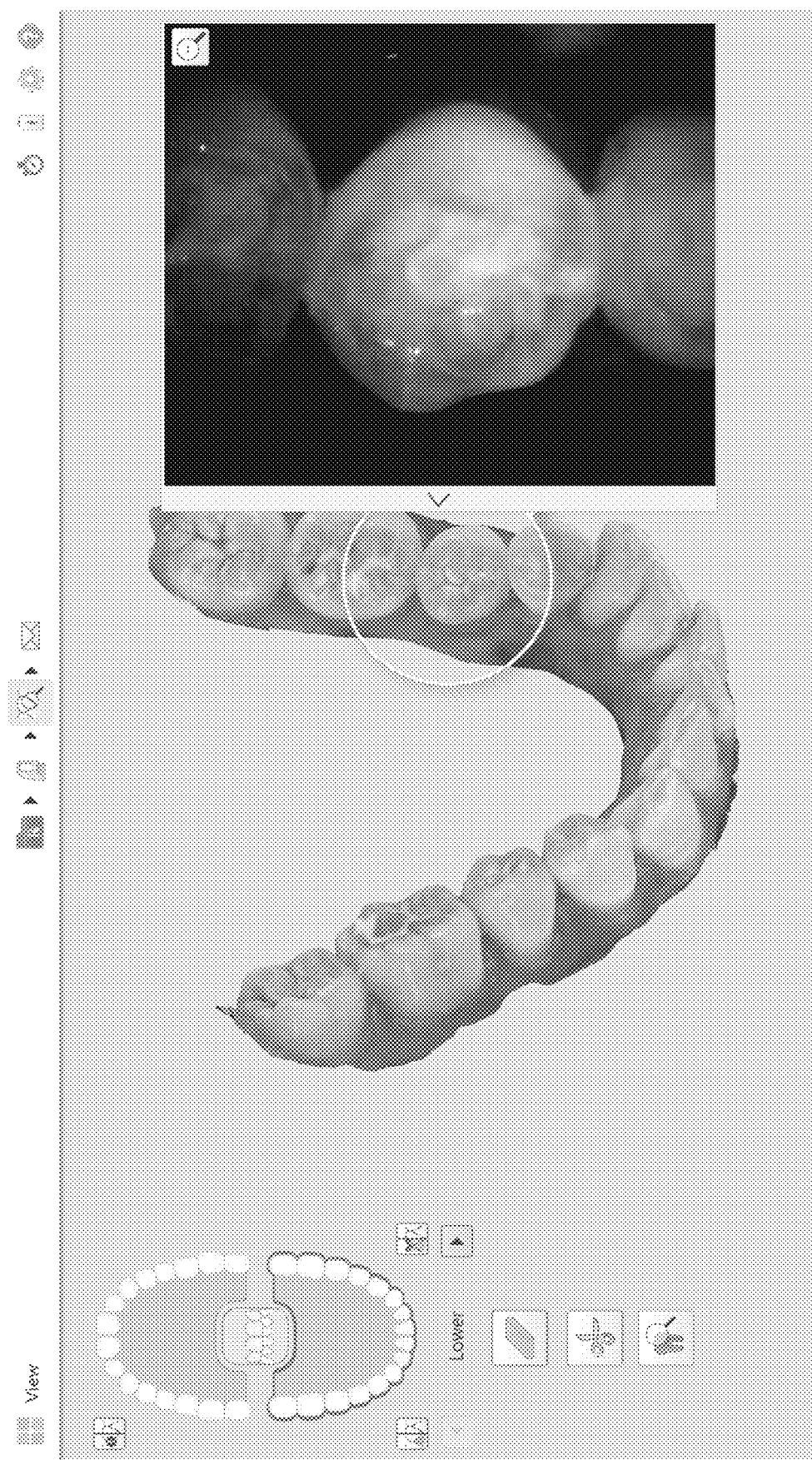
FIG. 16B shows an example of a single window (an enlarged near-IR view into the teeth of the region corresponding to the viewing window loop) similar to FIG. 16A.
Figure 16C:
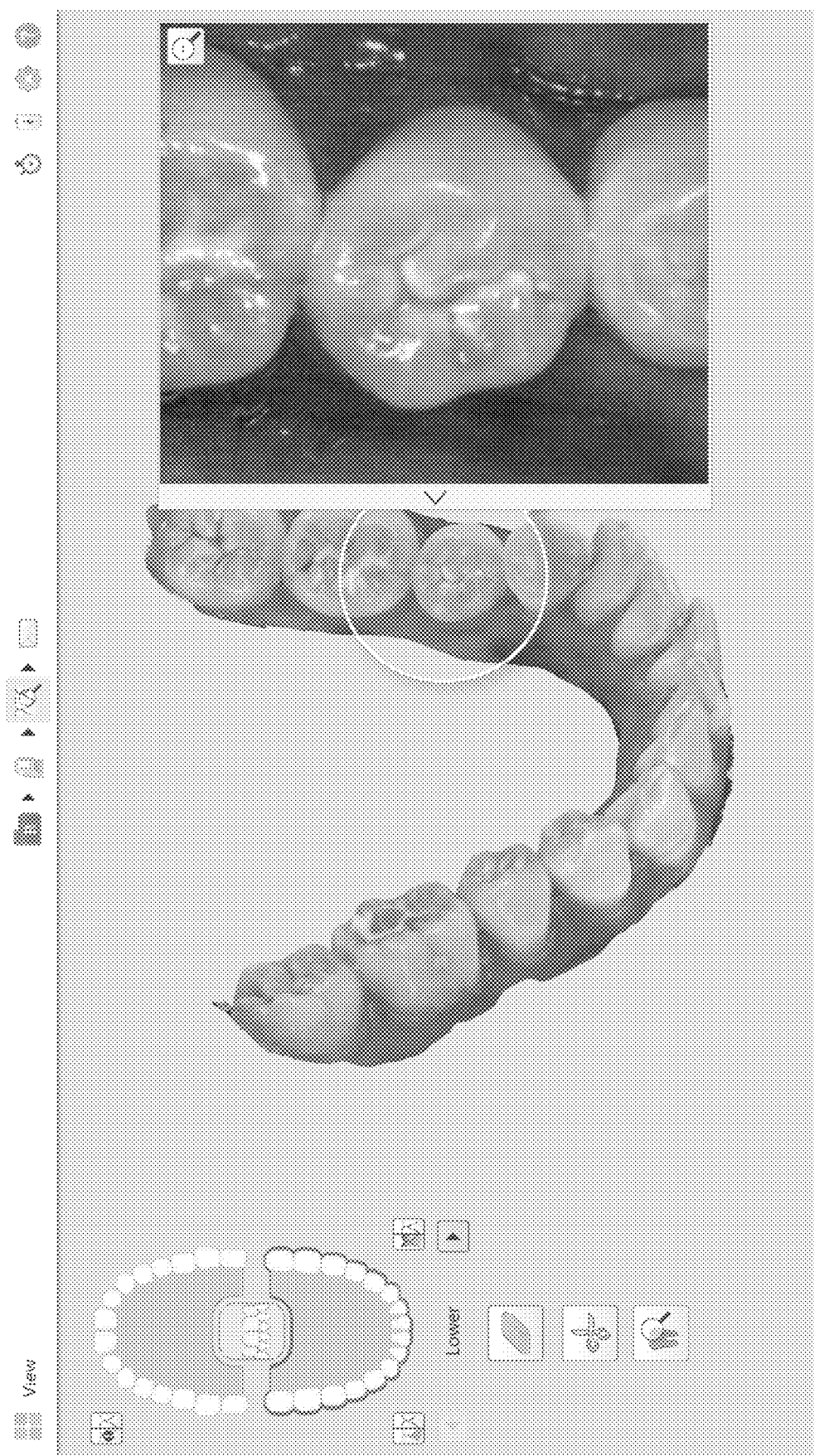
FIG. 16C shows an example of a single window (an enlarged visible light view into the teeth of the region corresponding to the viewing window loop) similar to FIG. 16A.

Similarly, FIGS. 16A-16C shows an example of a 3D model of a patient's lower arch similar to the view shown in FIG. 14A-14C. In use, as the user scans over and along the dental arch by moving the viewing window (and/or the dental arch relative to the viewing window), the display images may change virtually continuously, so that they may update in real or near-real time. The user may identify features in the near-IR image(s), including densities changes in the region of normally IR-transparent enamel, which may indicate carries, cracks, or wearing in the enamel.

The intraoral scanning system shown in FIGS. 1A-1B may be configured as an intraoral scanning system. Returning to FIG. 1A, the intraoral scanning system 101 includes a hand-held wand 103 having at least one image sensor and a light source configured to emit light at a spectral range within near-infrared (near-IR) range of wavelengths, and a display output (screen 102). The screen may be a touchscreen acting as a user input device, or the system may include a separate user input device (e.g., keyboard, touchpad, joystick, mouse, track ball, etc.). As indicated in FIG. 1B, the system may also include one or more processors that are operably connected to the hand-held wand, display and user input device. The one or more processors may include circuitry and/or software and/or firmware configured to: display a three-dimensional (3D) model of a patient's dental arch on the display output; display a viewing window over a portion of the 3D model of the patient's dental arch on the display output; change a relative position between the viewing window and the 3D model of the patient's dental arch based on input from the user input device; identify, from both the 3D model of the patient's dental arch and a plurality of images of the patient's dental arch taken from different angles and positions relative to the patient's dental arch, a near-infrared (near-IR) image taken at an angle and position that approximates a relative angle and position between the viewing window relative and the 3D model of the patient's dental arch; and display the identified near-IR image taken at the angle and position that approximates the angle and position between the viewing window relative to the 3D model of the patient's dental arch (as shown in FIGS. 14A-16C).

Automatic Characterization of Dental Features

Also described herein are methods and apparatuses (e.g., systems, including software) that is configured to use the 3D models, including but not limited to the volumetric 3D models, of all or a portion of a patient's dental arch to automatically or semi-automatically identify, confirm and/or characterize one or more dental feature. In particular, these methods and apparatuses may be configured to identify, confirm, and/or characterize one or more actionable dental features that may benefit from detection and/or treatment. Actionable dental features may include, but are not limited to cracks, gum recess, tartar, hard tissue and soft tissue oral conditions, etc. Enamel thickness may be another actionable dental feature. For example, the methods and apparatuses described herein may automatically map enamel thickness (e.g., apply color map where enamel is lower than x microns thick, where x may be preset and/or user adjustable). Areas of thin enamel are potential areas where caries may exist. Other potential actionable dental features may include discoloration (e.g., discontinuities in color), pits, fissures, evidence of grinding (thinning, including thinning over time), interproximal voids, etc., or any other similar feature that may be indicate or suggestive of where caries are likely to form.

Any of the methods and apparatuses described herein may use multiple different images or sets of images of the patient's teeth taken with different imaging modalities are used to detect, analyze and/or characterize dental features, and particularly actionable dental features. The multiple different images or sets of images of the patient's teeth taken with different imaging modalities may each be referred to as a "record". Each record may be a different imaging modality, such as dental cone beam computed tomography (CBCT) scanning, three dimensional (3D) intra-oral scanning, color scanning (one or more of: 3D color scanning, surface color scanning, etc.), two-dimensional (2D) color scanning, near-IR scanning (including, but not limited to one or more of: volumetric near-IR imaging, trans illumination and/or reflective scanning), X-ray (including, but not limited to: cephalometric analysis x-ray scanning, panoramic x-ray scanning, etc.), etc., and may include text or graphic chart information of the patient.

For example, each record may initially be processed independently. One or more dental features, and in particular, one or more actionable dental features, may be identified by this initial scan. A single record (e.g., a single imaging modality) may be used first to identify the one or more actionable dental features, or all of the records, or a subset of the records may be initially processed to identify the one or more actionable dental features. The initial identification of the one or more actionable dental features may be performed manually or automatically or semi-manually. For example, one or more actionable dental features may be identified automatically; a system as described herein may review the record (including the one or more images of the patient's teeth) to flag or identify regions having a characteristic associated with an actionable dental feature. A system may be trained, using machine learning techniques such as supervised learning techniques (e.g., classification, regression, similarity, etc.), unsupervised learning techniques (e.g., density estimation, cluster analysis, etc.), reinforcement learning (e.g., Markov Decision Process techniques, etc.), representation learning techniques and/or principle component analysis, etc., to identify/flag a region of a particular scan in a specified modality that is associated (even loosely associated with) an actionable dental characteristic. Alternatively or additionally, a user (dental professional, technician, etc.) may manually review one or more records (each in a particular imaging modality) and may flag or identify regions suspected to show an actionable dental characteristic. In a semi-automated configuration the system may initially flag one or more regions from a record that the user may then review and confirm/reject.

As the one or more regions are identified, they may be flagged and/or stored in a collection of potential actionable dental features. The location may be relative to (e.g., the location on) the originating record, or relative to a reference model (such as the 3D volumetric model, as will be described in greater detail below). In some variations the collection (e.g., array, data structure, file, etc.) may also include one or more of the type of potential actionable dental features, the extent of the potential actionable dental features, a grade and/or degree of the potential actionable dental features, the originating record and/or the imaging modality of the originating record, etc. In some variations the data structure may be integrated into the originating record (or a copy thereof) and may modify the image(s) of the originating record, e.g., by include a flag or marker at the location of the identified potential actionable dental features and/or any meta text such as the grade and/or degree, etc. The grade and/or degree may refer to the confidence level or score for the potential actionable dental feature, including the confidence level or score that the identified potential actionable dental features is likely 'real'.

This initial identification process to identify potential actionable dental features may be performed across multiple records, or it may be limited to a subset of the records (e.g., including just to one of the records), as mentioned above. In some variations the process may be iteratively performed.

Once one or more potential actionable dental features is identified, it may be cross-referenced to the other one or more records that use(s) other imaging modalities. Thus, the locations of the one or more potential actionable dental features may be examined in particular detail to determine if the same potential actionable dental feature is apparent on these one or more other record. In some variations the entire additional record(s) may be examined during this confirmation portion of the procedure, and any additional potential actionable dental features from the additional one or more records may be likewise flagged as a potential actionable dental feature and the same region of the dental arch may be examined for these other potential actionable dental features (including returning back to records that have already been reviewed, such as the first or originating record).

Comparison across other records may be guided by translating the locations of the dental features (including but not limited to the potential actionable dental features) between the different records. In particular, it may be helpful to coordinate the individual dental record(s) begin examined to a model of the patient's dental arch, such as any of the 3D models, and in particular, the 3D volumetric models, described above. The 3D model of the dental arch may therefore act as a key to translate the locations of the one or more potential actionable dental features and may allow rapid and efficient comparisons between the different records, e.g., different imaging modalities.

Thus, a correlation between each of the different records and, in particular, a correlation between all or some of the different records and a 3D model (e.g., a 3D volumetric model) of the dental arch may be established either before or after the initial scan for potential actionable dental features. Any method of correlating a records and other records and/or a 3D model of the patient's dental arch (or a portion of the dental arch) may be used. For example, one or more easily recognizable features (e.g., tooth edge, shape, segmentation, etc.) may be used to determine landmarks that may translate between the one or more records and/or the one or more records and the 3D model of the patient's dental arch. In some variations a translational dataset may be created that includes a transformation between the records and/or between each record and a 3D volumetric model of the patient's dental arch. For example, a 3D volumetric model of all or a portion of the dental arch may include transformation information for each of the one or more records allowing transformation of the image(s) of the one or more records, such as an estimate of the distance and/or orientation of the imaging modality relative to the record image(s). This allows both forward and reverse translation of position between each record and the 3D model (e.g. volumetric model).

Thus, a translational dataset may include a 3D model and the translational information of each record, so that a portion or region of a record image (or images) may be projected onto the 3D (translational) model, and the same region then back projected onto a second (or more) record taken with another imaging modality so that the same region may be examined. In some variations the process may begin with the collection of all the records and/or an automatic, manual or semi-automatic registration between all the records. For example, the identification of individual teeth, palate, gingiva, etc. regions, may be used to cross-correlate between the different imaging modalities and/or the 3D model. In one example, a record including x-ray images may be correlated with a 3D volumetric model of the patient's teeth by solving (manually or automatically) for the position and/or orientation of the x-ray camera taking the x-ray images corresponding to the record. The volumetric model may be used to determine and/or confirm the location and/or orientation of imaging source for each record. In some variations the record include explicit (e.g., recorded) information about the position and/or orientation and/or imaging parameters used to take the image(s); alternatively or additionally, this information may be derived. As described above one a pseudo-x-ray image may be generated and compared to an actual x-ray image of the record.

Once a region corresponding to the region of the potential actionable dental feature from another record is identified, the system or method may then determine if the same potential actionable dental features is present in this other record. If present, the score (e.g. confidence score, showing the likelihood that the potential actionable dental features is real) may be adjusted, e.g., increased if the same or a similar potential actionable dental feature is present. Depending on the type of record and the type of potential actionable dental features, the absence of a potential actionable dental features may result in adjusting the confidence score. For example, the absence of surface features that are not typically detectable by X-rays, such as discoloration, plaque, gum recession, etc., may not result in lowering the confidence score of the one or more potential actionable dental features. The more occurrences of finding a potential actionable dental features a corresponding location between different records (therefore in different modalities), the more likely that the potential actionable dental features really exists.

In comparing the corresponding locations of the one or more potential actionable dental features the region may be examined manually, automatically or semi-automatically, similar to the original identification techniques discussed above. For example, a region of an additional record corresponding to the location of a potential actionable dental feature in another record may be examined automatically to identify features correlated with the type of potential actionable dental feature. The system may be trained to recognize the potential actionable dental feature in the imaging modality of the additional record and may provide a score indicating the likelihood that the potential actionable dental feature is present in this location. In some variations a user (e.g., technician, dental professional, etc.) may be presented with an image from the additional record(s) and may manually indicate the likelihood (yes/no, graded scale, numeric scale, etc.) that the potential actionable dental feature is present in the one or more additional records.

The final confidence value determined for each potential actionable dental feature may be used by the system: stored, transmitted and/or displayed. For example the potential actionable dental feature(s) may be presented to a dental practitioner in any appropriate manner, including in a list, on a display, such as on 3D model of the dental arch (including the translational 3D dental model) marked, etc. For example, the system may output a display highlights by color, shape, etc. the location of any or all of the potential actionable dental features that are above a threshold confidence level (so likely to be 'real'); the display may also include one or more views (from the one or more records) of the potential actionable dental feature. The user may set of adjust the threshold confidence level, including on the fly (e.g., making the threshold more or less stringent and showing the addition or removal of potential actionable dental features in response.

Figure 17:
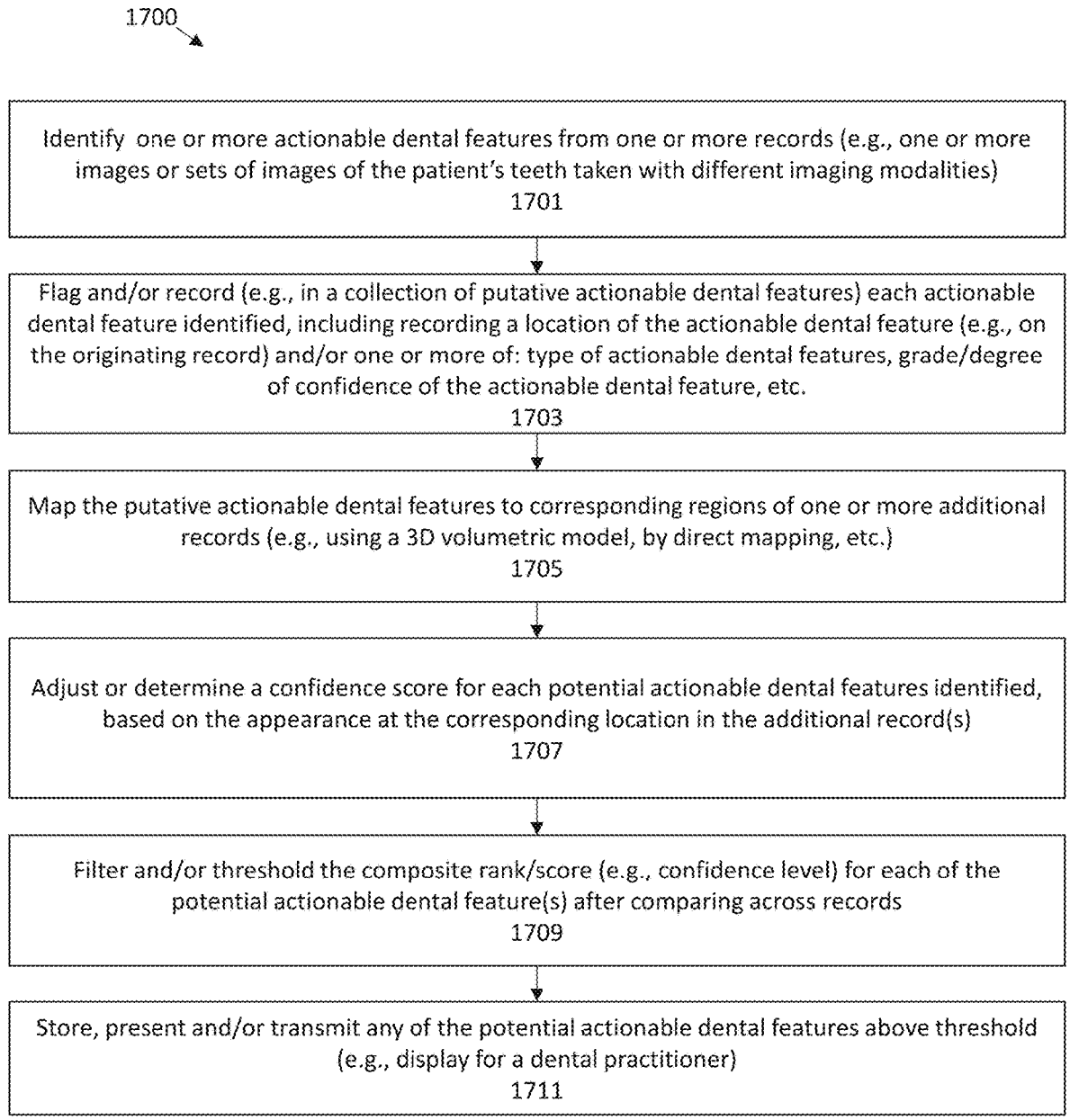
FIG. 17 schematically illustrates one example of a method for automatically or semi-automatically identify, confirm and/or characterize one or more actionable dental features that may benefit from detection and/or treatment.

FIG. 17 illustrates one example of a method 1700 for characterizing dental features across different imaging modalities as just discussed. In FIG. 17, the method (or a system configured to perform it) may identify one or more actionable dental features from one or more records (e.g., one or more images or sets of images of the patient's teeth taken with different imaging modalities) 1701. For example, the one or more actionable dental features may be identified by an agent or engine that is configured to automatically detect one or more actionable dental features. For example, a system performing the method of FIG. 17 may include an actionable dental feature analysis engine, or may include multiple actionable dental feature analysis engines each configured to identify one or more types of actionable dental features or one or more types of imaging modality. The engine (e.g., an actionable dental feature analysis engine) may be part of a computer system. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

Returning to FIG. 17, the one or more actionable dental features may be identified from one or more records manually or semi-manually. For example, an actionable dental feature analysis engine may initially identify one or more actionable dental features that may then be verified or vetted by a user (e.g., dental technician).

Each actionable dental feature identified may then be flagged and/or recorded, e.g., in a collection of potential actionable dental features 1703. For example a collection of potential actionable dental features may be part of a data structure. Adding the potential actionable dental feature(s) to a collection (e.g., data structure) may include recording a location of the actionable dental feature (e.g., on the originating record) and/or one or more of: type of actionable dental features, grade/degree of confidence of the actionable dental feature, etc. As used herein, a data structure (which may be included as part of a datastore) is intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

A data structure may be associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The identified "putative" actionable dental features (e.g., "potential actionable dental features") may be mapped to corresponding physical locations in one or more other records 1705. As discussed above, in some variations this may be done using the 3D volumetric model, which may translate between the various different types of records (having different imaging modalities), including projecting a first record onto the 3D model and then back onto a second region.

Thus, the same corresponding regions in other records may be reviewed to determine if the potential actionable dental feature is present or suggested in the additional record(s). In some variations, the method may simply collect all of the different corresponding regions for storage, transmission and/or presentation to a user (e.g., dental professional), e.g., optionally stopping here and allowing the user to review these flagged region from multiple different imaging modalities (records) in parallel. For example, the potential actionable dental feature may be shown for all corresponding views in a side-by-side (e.g., tiled) or sequential view(s).

Alternatively or additionally, the method and/or system may automatically or semi-automatically adjust a confidence score for each of the potential actionable dental features identified. Thus, the system may determine if the additional records indicate that the potential actionable dental feature is more likely to be present or less likely to be present and may adjust (or determine) the confidence score for each of the potential actionable dental features, based on the appearance at the corresponding location in the additional record(s) 1707.

The adjusted confidence levels may then be used to narrow down the potential actionable dental features. For example, the method or system may then filter and/or apply a threshold based on the adjusted confidence level for each potential actionable dental feature 1709. In some variation the threshold may be fixed (e.g., confidence level of greater than x, where x is a numeric value intermediate between zero confidence and 1 (absolute confidence), e.g., 0.1, 0.2, 0.3, 0.4, 0.5, 0.6, 0.7, 0.8, etc. In some variations the threshold value may be manually adjusted by the user and/or may be based on one or more features of the records, such as a quality metric specific to each of the records, etc.

Potential actionable dental feature having a confidence level that is above the threshold value may then be stored, presented and/or transmitted 1711. For example a user may be presented with a final list and/or display (e.g., using the 3D model) including the flagged potential actionable dental features.

Any of the methods and apparatuses (e.g., systems) described herein may be configured to build a data structure including all or part of the multiple records. For example, a data structure may include a 3D volumetric model and all or some of the associated 2D images that were used to construct it, as described above. In addition, the data structure may include additional records, such as images taken by X-ray (e.g., panoramic), and/or CBCT, etc. Metadata, e.g., information, including textual information, about the patient and/or images may also be included, including optionally patient chart information from the patient's health/dental records. Alternatively or additionally, any identified potential actionable dental features (e.g., findings identified from the records) may also be included. The potential actionable dental features may be used to search/find/mark on the other records.

Typically, when compiling the images (e.g., 2D near-IR images) to build the 3D (e.g., volumetric) model, the 2D images that provided information may be marked to indicate the significance to the 3D model. For example, 2D images may be marked as less relevant or more relevant.

As mentioned above, the collection of potential actionable dental features, including their confidence level based on their presence in multiple records may be included as part of the same data structure including the 3D model, or it may be separate. The 3D model may be directly marked (flagged, coded, etc.) to include the potential actionable dental features. Thus, the data structure may be a compilation of all of the different records. The combined/compiled data structure may be referred to as a marked data structure or an actionable dental feature data structure.

Any of the records, including the near-IR 2D images, may be used/scanned to identify the potential actionable dental features. As described above when a suspicious area is identified, either automatically, semi-automatically/semi-manually, or manually (e.g., by a user), in one of the records, the method or system may then search the corresponding area of the dental arch on all or some of the other records and conclude if there is a finding. In some variations, the method or apparatus may update the images on all or some of the records (and/or in the combined data structure) based on the analysis described herein.

In any of the methods and systems described herein, tooth segmentation may be used on all or some of the records and/or the 3D model to enhance performance and usability. Tooth segmentation may be added prior to volumetric modeling to assist and improve volumetric results and model quality. For example, the volumetric 3D model may uses the information of segmentation to potentially enhance performance as additional surface 3D information is added. The segmentation information may also assist in segmenting enamel-dentin-lesions to improve auto detection and suspicious areas marking (e.g., including but not limited to when using an automatic agent to identify potential actionable dental features). Alternatively or additionally, tooth segmentation may be added to the volumetric modeling post-processing to assist in segmenting enamel-dentin-lesions to improve auto detection and suspicious areas marking. For example, segmentation may also or alternatively help with correlating the structures between different imaging modalities, including registering findings on volumetric with other modalities to provide cross-modality visualization. Tooth segmentation may be used to improve records and cross-modality visualization of clinical findings and annotations In any of the methods and apparatuses described herein the confidence level indicated may be a quantitative and/or qualitative index. For example, a quantitative confidence level "score" may be provided (e.g., using a number between, for example, 0-100, 0 to 1.0, −100 to 100, or scaled to any range of numeric values). Qualitative indexes may include "high, medium high, medium, medium low, low", etc. Both qualitative and quantitative confidence levels may be used. A rating system for the confidence level based on the multiple records as described herein may be impactful for insurance claims and/or patient communication.

In any of the methods and system described herein, the morphology of the dental arch may be used to help identify the likely areas of interest or potential issues. Thus, in general, the 3D model (volumetric model) may be used and/or modified as described herein in order to include the regions of potential actionable dental features. A modified 3D model may act as a map that visually indicates areas of areas for risk assessment; this may be used, for example, to guide treatment of the patient, including to promote use of sealants, orthodontic treatment or night guards, etc. In some variations, the modified 3D model may be used to guide a user when additional scans are needed (e.g., when there is a low number of scans in the risk areas). As used herein, a modified 3D model may include a 3D (e.g., volumetric and/or surface) model that has been marked to indicate the locations and/or type and/or confidence level of potential actionable dental features. Thus, in general, the use of additional data sources to guide users to capture potential areas of interest (e.g., when they appear in records, and particularly in records other than near-IR/NIRI scan) may help confirm findings of potential actionable dental features. As mentioned, the results, including a modified 3D model, may help guide the user in scanning or re-scanning (at a future time) the user's dentition. For example, historical scans can be used as a targeting map while scanning (and to confirm adequate coverage in those areas). One or more derived images/presentations may be used in addition or alternatively. For example, tooth segmentation may be used to generate a tooth chart map (e.g., from the 3D volumetric model) that can be used for follow up and auto import into dental practice management software (DPMS). For example, individual records may be lined to match a specified problem to a tooth map.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of displaying pseudo X-ray images from a three-dimensional (3D) model of a patient's dental arch, the method comprising:
    collecting the 3D model of the patient's dental arch, wherein the 3D model includes near-infrared (near-IR) transparency values of internal structures within the patient's dental arch;
    generating a two-dimensional (2D) view extracted from the 3D model of the patient's dental arch, wherein the 2D view includes the near-IR transparency values of the internal structures from the 3D model;
    mapping the near-IR transparency values of the internal structures in the 2D view to a pseudo X-ray density in which pseudo X-ray density in the 2D view is based on the near-IR transparency values that are inverted in value; and
    displaying the mapped pseudo X-ray density as one or more pseudo X-ray images.

2. The method of claim 1, further comprising identifying individual teeth or groups of teeth from the 3D model.

3. The method of claim 2, wherein the individual teeth or groups of teeth are identified automatically.

4. The method of claim 2, wherein identifying the individual teeth or groups of teeth by segmenting the 3D model using machine learning.

5. The method of claim 1, wherein collecting the 3D model comprises collecting data based on absorption coefficients of material of the patient's dental arch.

6. The method of claim 1, wherein displaying the one or more pseudo X-ray images comprises projecting through the 3D model for a fixed direction.

7. The method of claim 1, wherein displaying the one or more pseudo X-ray images comprises distinguishably presenting dentin, enamel and caries of teeth of the patient's dental arch.

8. The method of claim 7, wherein the dentin and caries are presented as darker than the enamel.

9. The method of claim 1, further comprising applying coloring to certain regions of the patient's dental arch in the one or more pseudo X-ray images.

10. The method of claim 9, wherein marked regions of the patient's dental arch are colored in a first color and unmarked regions are colored in a second color different than the first color.

11. The method of claim 1, further comprising comparing the one or more pseudo X-ray images with one or more actual X-ray images.

12. The method of claim 1, further comprising generating a panel of pseudo X-ray images for each of the patient's teeth.

13. A method of displaying pseudo X-ray images from a three-dimensional (3D) model of a patient's dental arch, the method comprising:
   collecting the 3D model of the patient's dental arch, wherein the 3D model includes surface features and near-infrared (near-IR) transparency values of internal structures within the patient's dental arch in which enamel is more transparent than dentin;
   generating a two-dimensional (2D) view extracted from the 3D model including the patient's dental arch, wherein the 2D view includes the near-IR transparency values of the internal structures including the dentin and the enamel;
   mapping the near-IR transparency values of the internal structures in the 2D view to a pseudo X-ray density in which the near-IR transparency values are inverted in value so that the enamel is brighter than the dentin; and
   displaying the mapped pseudo X-ray density as one or more pseudo X-ray images.

14. The method of claim 13, displaying the one or more pseudo X-ray images comprises presenting certain internal features with one or more annotation, coloring, and texturing.

15. The method of claim 13, displaying the one or more pseudo X-ray images comprises generating a panel of pseudo X-ray images for each of the patient's teeth.

16. The method of claim 13, wherein the near-IR transparency values are inverted in value such that the enamel is brighter than caries in the patient's teeth.

17. The method of claim 13, wherein displaying the one or more pseudo X-ray images comprises projecting through the 3D model for a fixed direction.

18. The method of claim 13, wherein the one or more pseudo X-ray images are generated from a volume or sub-sets of the volume corresponding to individual teeth.

19. The method of claim 13, further comprising identifying individual teeth or groups of teeth from the 3D model.

20. The method of claim 13, wherein collecting the 3D model comprises collecting data based on absorption coefficients of material of the patient's dental arch.

* * * * *